United States Patent
Yamamoto et al.

(10) Patent No.: US 11,472,763 B2
(45) Date of Patent: Oct. 18, 2022

(54) CALIXARENE COMPOUND, CURABLE COMPOSITION, AND CURED PRODUCT

(71) Applicant: DIC Corporation, Tokyo (JP)

(72) Inventors: Shinya Yamamoto, Sakura (JP); Yutaka Kadomoto, Kitaadachi-gun (JP); Masanori Miyamoto, Sakura (JP); Tomoyuki Imada, Ichihara (JP); Hidetomo Kai, Sakura (JP)

(73) Assignee: DIC Corporation, Tokyo (JP)

( * ) Notice: Subject to any disclaimer, the term of this patent is extended or adjusted under 35 U.S.C. 154(b) by 230 days.

(21) Appl. No.: 16/636,048

(22) PCT Filed: Jul. 19, 2018

(86) PCT No.: PCT/JP2018/027063
§ 371 (c)(1),
(2) Date: Feb. 3, 2020

(87) PCT Pub. No.: WO2019/031182
PCT Pub. Date: Feb. 14, 2019

(65) Prior Publication Data
US 2021/0198178 A1     Jul. 1, 2021

(30) Foreign Application Priority Data

Aug. 8, 2017 (JP) .............................. JP2017-153263
May 15, 2018 (JP) .............................. JP2018-093760

(51) Int. Cl.
*C07C 69/732* (2006.01)
*C07C 69/54* (2006.01)
(Continued)

(52) U.S. Cl.
CPC .......... *C07C 69/732* (2013.01); *C07C 59/305* (2013.01); *C07C 69/54* (2013.01);
(Continued)

(58) Field of Classification Search
CPC ..... C07C 69/54; C07C 69/602; C07C 69/732; C07C 59/66; C07C 59/305; C07C 49/83; C07C 2603/92
See application file for complete search history.

(56) References Cited

U.S. PATENT DOCUMENTS

| | | | | |
|---|---|---|---|---|
| 5,840,814 A | * | 11/1998 | Majoros | ................. C07C 69/00 525/138 |
| 2016/0289350 A1 | | 10/2016 | Taylor et al. | |
| 2019/0276421 A1 | | 9/2019 | Yamamoto et al. | |

FOREIGN PATENT DOCUMENTS

| | | |
|---|---|---|
| JP | H09-263560 A | 10/1997 |
| JP | H11-072916 A | 3/1999 |

(Continued)

OTHER PUBLICATIONS

Osipov, M. et al., Synthesis of deep-cavity fluorous calix[4]arenes as molecular recognition scaffolds, Beilstein Journal of Organic Chemistry, vol. 4, No. 36, pp. 1-6 (Year: 2008).*

(Continued)

*Primary Examiner* — Yate' K Cutliff
(74) *Attorney, Agent, or Firm* — Locke Lord LLP; James E. Armstrong, IV; Nicholas J. DiCeglie, Jr.

(57) ABSTRACT

A calixarene compound represented by formula (1) below is provided. The calixarene compound contains, per molecule, at least one —$CH_2OH$ group or phenolic hydroxy group and at least one carbon-carbon unsaturated bond. $R^1$'s are a structural moiety (A), which has a —$CH_2OH$ group; a structural moiety (B), which has a carbon-carbon unsaturated bond; a structural moiety (C), which has a —$CH_2OH$ group and a carbon-carbon unsaturated bond; a monovalent organic group (D), which is different from (A), (B), and (C); or a hydrogen atom (E). $R^2$'s are (A), (B), (C), (D), or (E) provided that not all $R^2$'s are (E). $R^3$'s are one of a hydrogen (Continued)

atom, an aliphatic hydrocarbon group, and an aryl group, n is 2 to 10. * is a point of attachment to an aromatic ring. A curable composition including the calixarene compound is provided. A cured product of the curable composition is provided

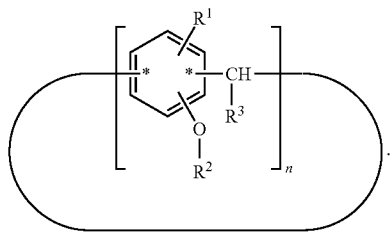

(1)

8 Claims, 4 Drawing Sheets

(51) Int. Cl.
*C07C 69/602* (2006.01)
*C08F 2/48* (2006.01)
*C07C 59/305* (2006.01)

(52) U.S. Cl.
CPC .............. *C07C 69/602* (2013.01); *C08F 2/48* (2013.01); *C07C 2603/92* (2017.05)

(56) References Cited

FOREIGN PATENT DOCUMENTS

| JP | 2002-003563 | A | 1/2002 | |
| JP | 2002-069140 | A | 3/2002 | |
| JP | 2012-102035 | * | 5/2012 | ............. C07C 41/16 |
| JP | 2016-538389 | A | 12/2016 | |
| WO | 2018/101057 | A1 | 6/2018 | |

OTHER PUBLICATIONS

JP 2012102035, Tachibana, S., et al., Manufacture of ethoxylated calixarenes by addition polymerization of ethylene carbonate to calixarenes, English translation 9 pages (Year: 2015).*
Zhi-Tang Huang et al., "Selective Esterification of Calix[4]arenes," Synthetic Communications, 24(1), 1994, pp. 11-22 and information sheets, (cited in the ISR).
Monirtabatabai et al., "New calix[4]arenedimethacrylate derivatives for dental composites," Polym. Int, 61, 2012, pp. 407-412. (cited in the ISR).
Muzaffar Iqbal et al., "Calixarenes 21. The conformations and structures of the products of aroylation of the calix [4]arene", Tetrahedron, vol. 43, No. 21, 1987, pp. 4917-4930. (cited in the ISR).
International Search Report dated Oct. 16, 2018, issued for PCT/JP2018/027063.

* cited by examiner

[Fig. 1]
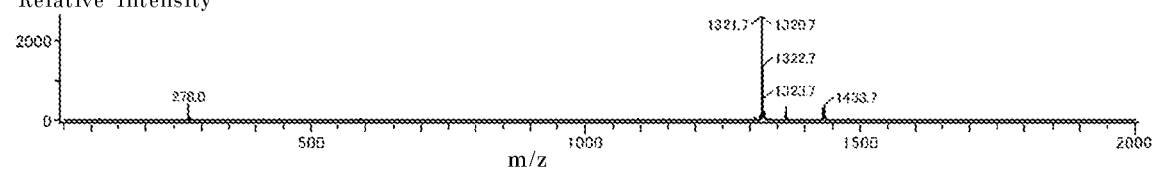
[Fig. 2]
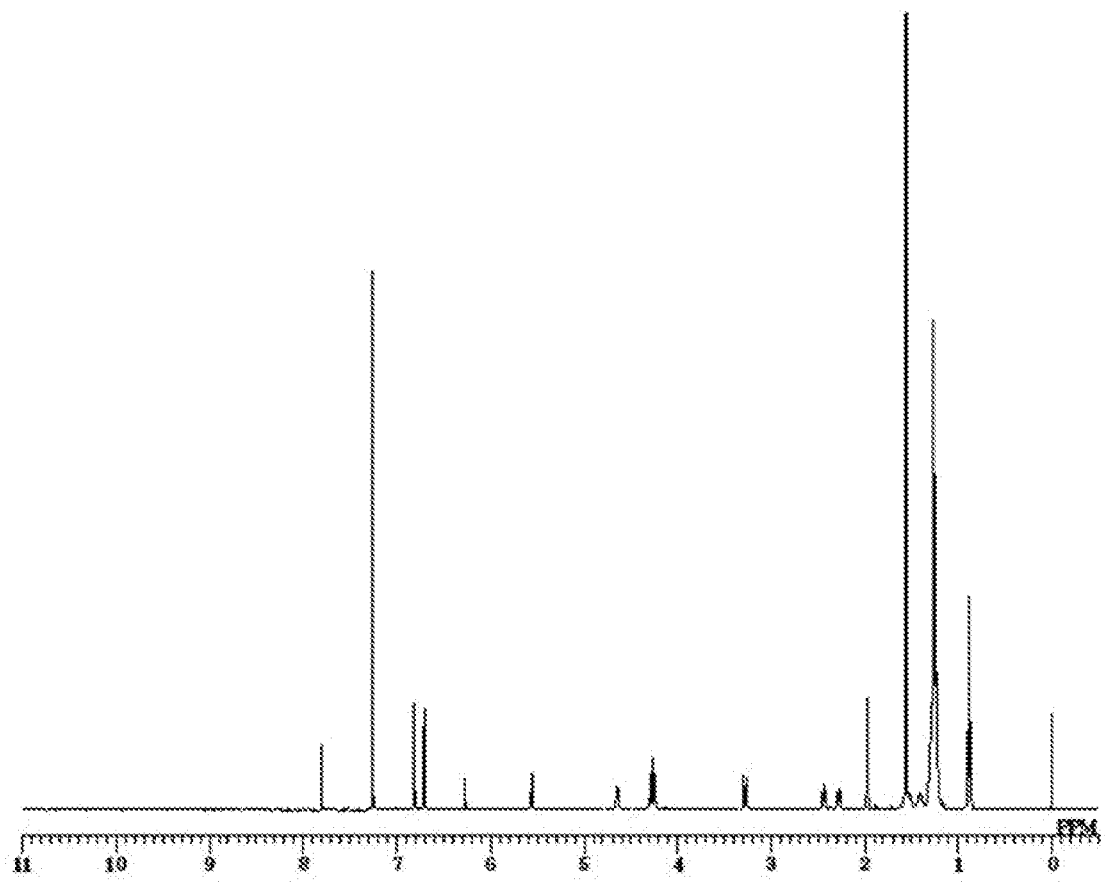

[Fig. 3]
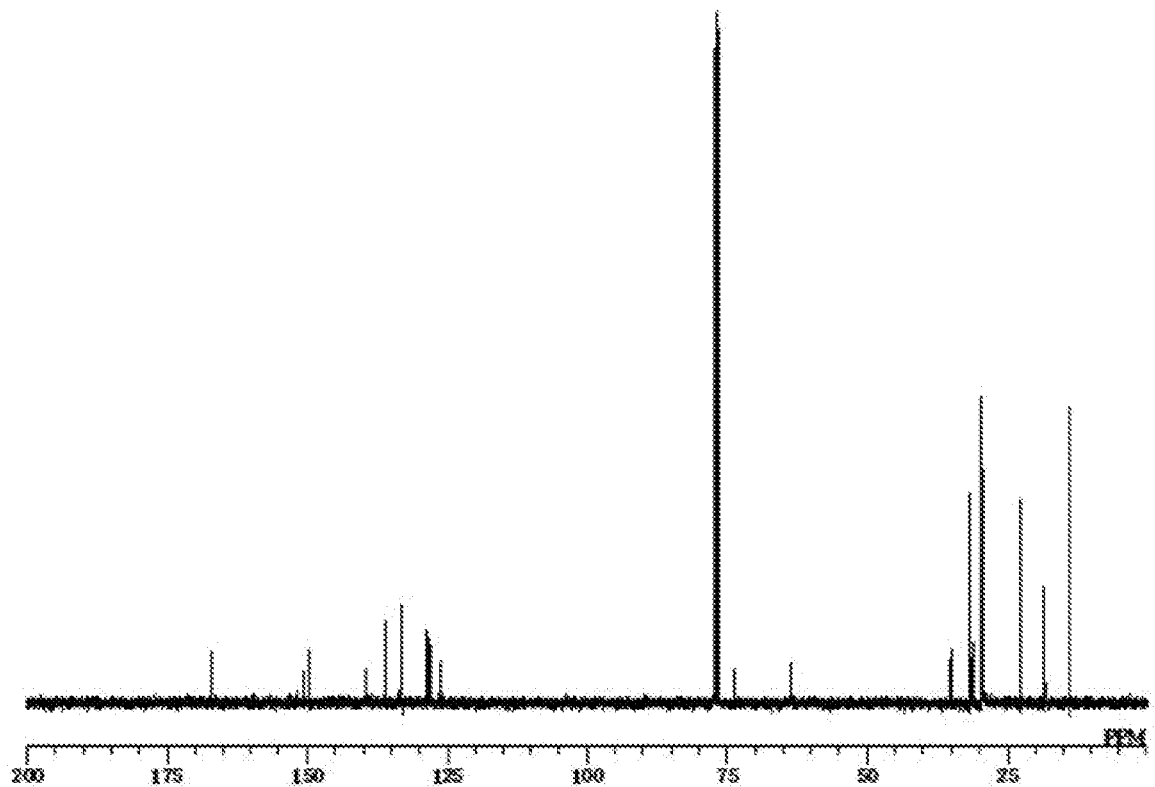
[Fig. 4]
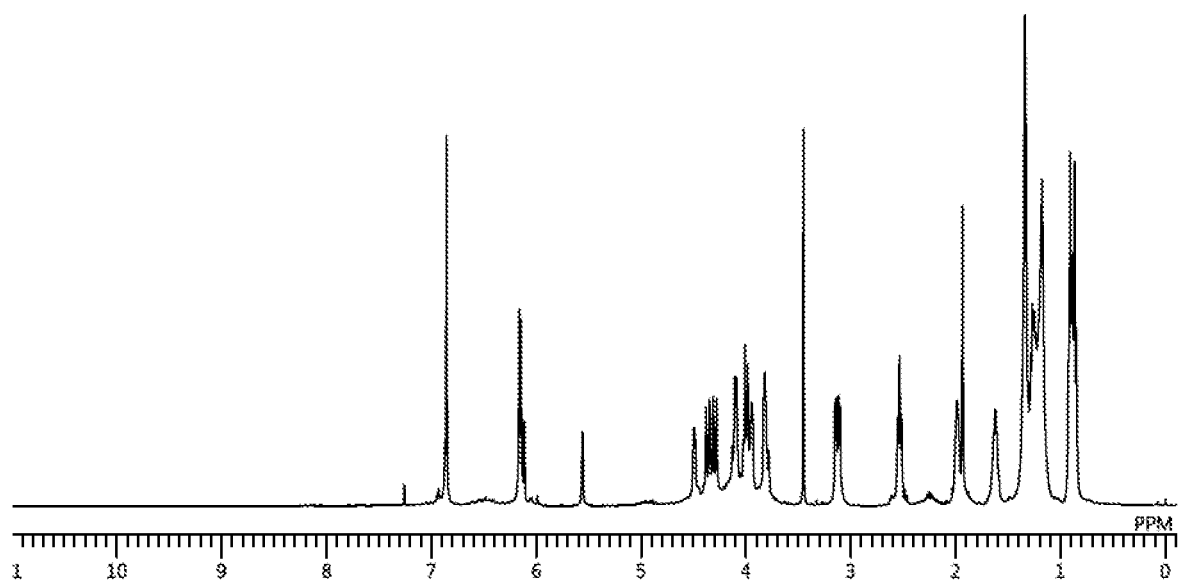

[Fig. 5]
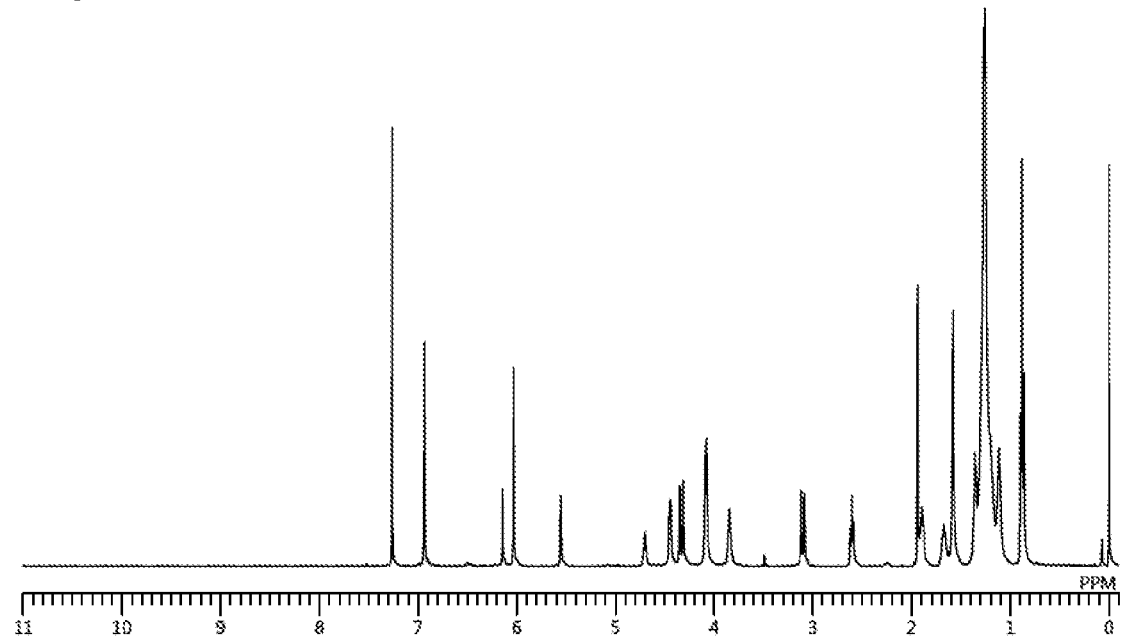
[Fig. 6]
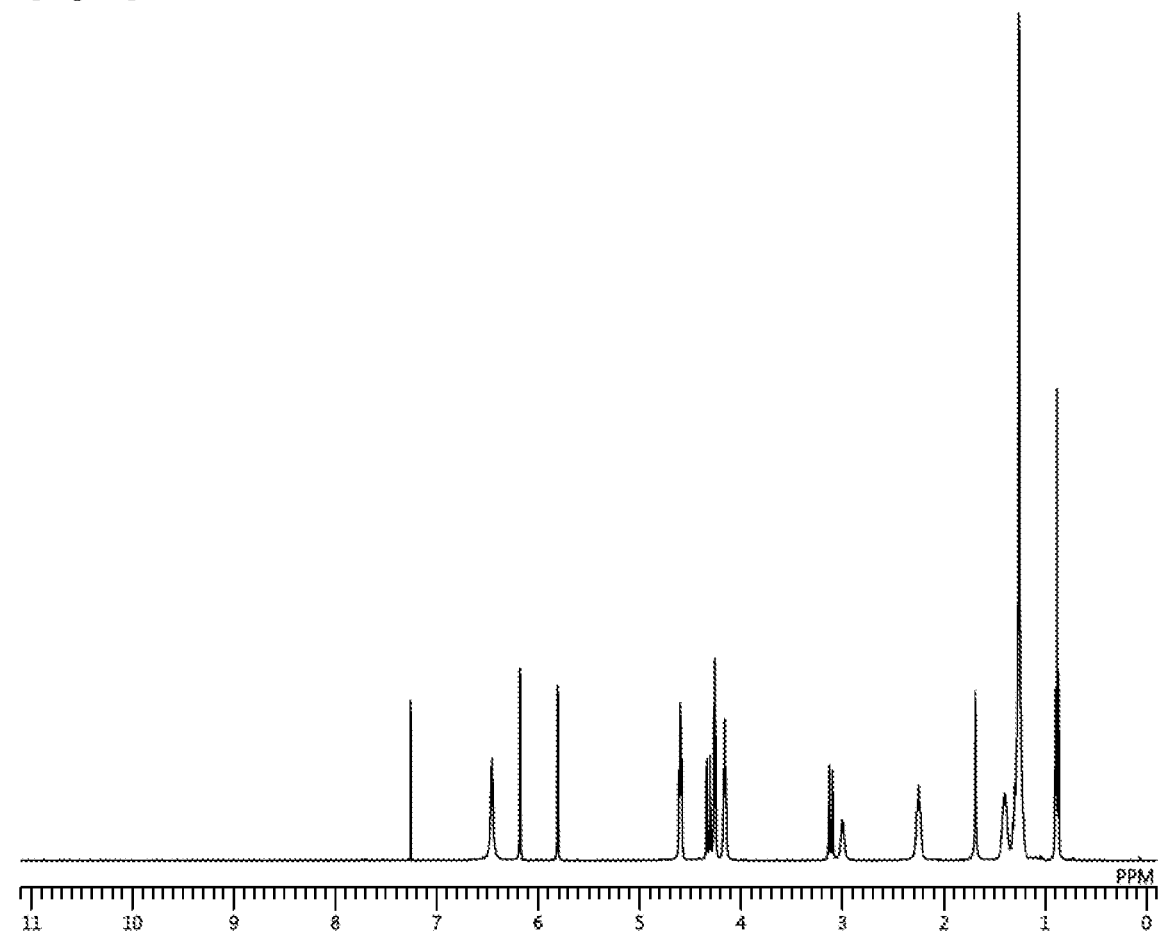

[Fig. 7]
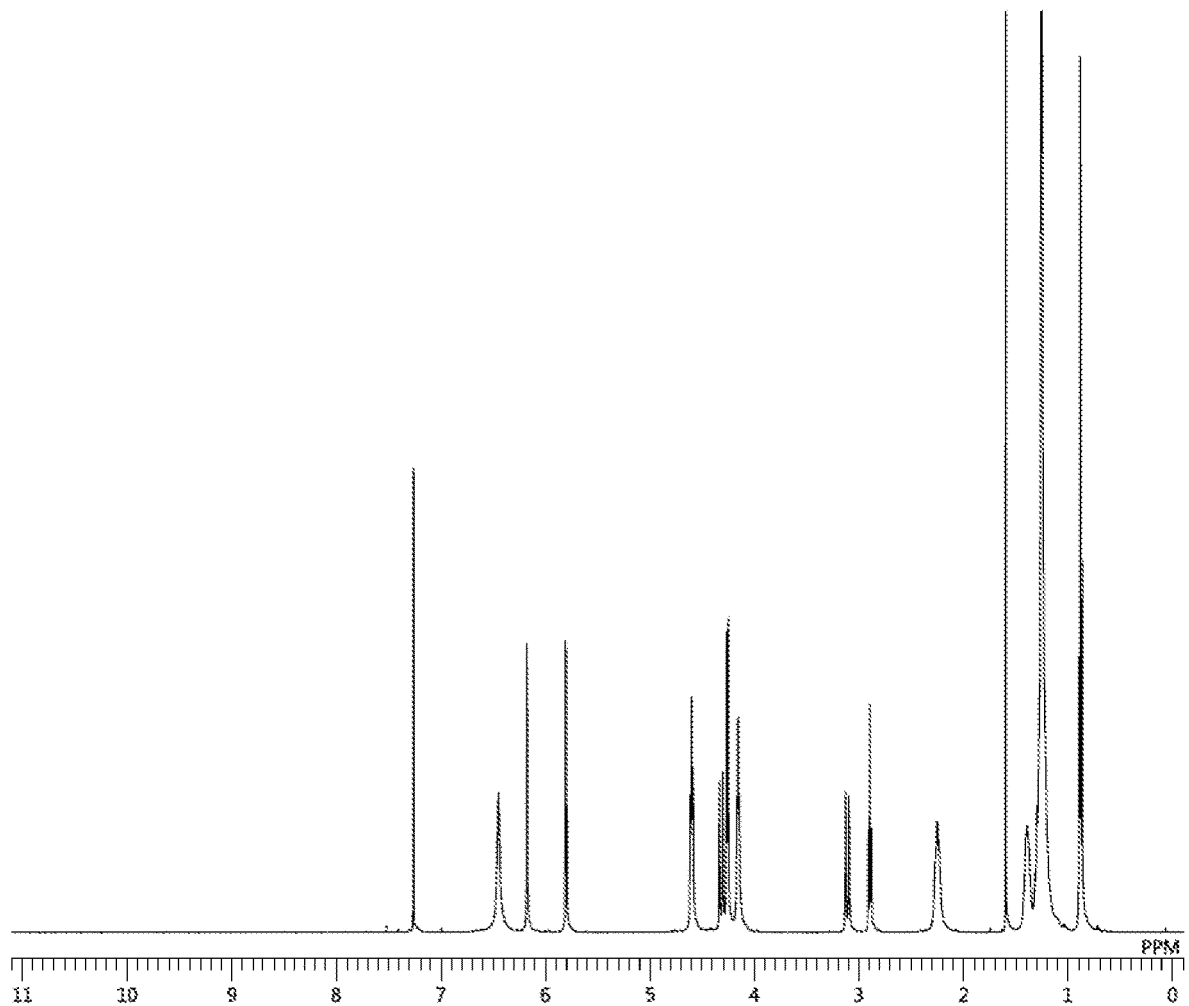

CALIXARENE COMPOUND, CURABLE COMPOSITION, AND CURED PRODUCT

TECHNICAL FIELD

The present invention relates to a calixarene compound having a novel structure and relates to a curable composition including the calixarene compound and to a cured product of the curable composition.

BACKGROUND ART

Calixarene compounds are expected to provide advantages due to their peculiar structures, such as excellent heat resistance and robustness, and, accordingly, various studies have been conducted for a variety of applications, including special paints and resist materials. Examples of known technologies related to calixarene compounds include a technology in which a (meth)acryloyl group or the like is introduced to a phenolic hydroxy group of a para-cresol-type or para-tertiary-butyl-phenol-type calixarene, for use in a paint that provides excellent heat resistance and surface hardness (see PTL 1, for example) or for use in a resist material that enables formation of a fine pattern (see PTL 2, for example). As stated above, calixarene compounds are compounds that are expected to provide advantages such as excellent heat resistance and robustness, but, on the other hand, problems exist in that, for example, calixarene compounds are highly crystalline, hard but brittle, and have low adhesion to a substrate. The calixarene compounds described in PTL 1 and 2 also presented such problems. Accordingly, there is a need for the development of a calixarene compound that can overcome these problems and, therefore, has high utility.

CITATION LIST

Patent Literature

PTL 1: Japanese Unexamined Patent Application Publication No. 9-263560
PTL 2: Japanese Unexamined Patent Application Publication No. 11-72916

SUMMARY OF INVENTION

Technical Problem

Accordingly, an object of the present invention is to provide a calixarene compound that has a novel structure and which has excellent properties in terms of not only, for example, heat resistance and hardness but also, for example, adhesion to a substrate, and further objects are to provide a curable composition including the calixarene compound and to provide a cured product of the curable composition.

Solution to Problem

The present inventors diligently performed studies to solve the problems described above and found the following. A calixarene compound containing, per molecule, at least one —CH$_2$OH group or phenolic hydroxy group and at least one carbon-carbon unsaturated bond can form a cured product or a molded body having excellent properties in terms of not only, for example, heat resistance and hardness but also, for example, adhesion to a substrate. Accordingly, the present invention was completed.

Specifically, the present invention provides a calixarene compound represented by structural formula (1) below. The calixarene compound contains, per molecule, at least one —CH$_2$OH group or phenolic hydroxy group and at least one carbon-carbon unsaturated bond.

[Chem. 1]

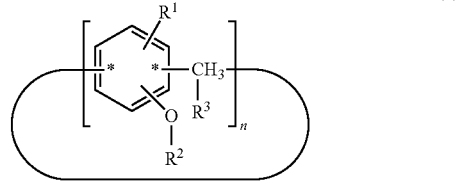

(1)

Here, R$^1$'s are a structural moiety (A), which has a —CH$_2$OH group; a structural moiety (B), which has a carbon-carbon unsaturated bond; a structural moiety (C), which has both a —CH$_2$OH group and a carbon-carbon unsaturated bond; a monovalent organic group (D), which is different from the structural moiety (A), the structural moiety (B), and the structural moiety (C) and has 1 to 20 carbon atoms; or a hydrogen atom (E). R$^2$'s are a structural moiety (A), which has a —CH$_2$OH group; a structural moiety (B), which has a carbon-carbon unsaturated bond; a structural moiety (C), which has both a —CH$_2$OH group and a carbon-carbon unsaturated bond; a monovalent organic group (D), which is different from the structural moiety (A), the structural moiety (B), and the structural moiety (C) and has 1 to 20 carbon atoms; or a hydrogen atom (E), provided that not all R$^2$'s are a hydrogen atom (E). R$^3$'s are one of a hydrogen atom, an optionally substituted aliphatic hydrocarbon group, and an optionally substituted aryl group. n is an integer of 2 to 10. R$^1$'s are identical to or different from one another, R$^2$'s are identical to or different from one another, and R$^3$'s are identical to or different from one another, per molecule. * is a point of attachment to an aromatic ring. In addition, the present invention provides a curable composition including the calixarene compound and provides a cured product of the curable composition.

Advantageous Effects of Invention

The present invention provides a calixarene compound that has a novel structure and which has excellent properties in terms of not only, for example, heat resistance and hardness but also, for example, adhesion to a substrate. The present invention also provides a curable composition including the calixarene compound and provides a cured product of the curable composition. Calixarene compounds of the present invention are suitable for use in a variety of applications, such as paints, printing inks, adhesives, resist materials, and interlayer insulating films.

BRIEF DESCRIPTION OF DRAWINGS

FIG. 1 is an FD-MS chart of a calixarene compound (1-2), which was obtained in Example 1.
FIG. 2 is a $^1$H-NMR chart of the calixarene compound (1-2) obtained in Example 1.
FIG. 3 is a $^{13}$C-NMR chart of the calixarene compound (1-2) obtained in Example 1.
FIG. 4 is a $^1$H-NMR chart of a calixarene compound (23-1), which was obtained in Example 23.

FIG. 5 is a $^1$H-NMR chart of a calixarene compound (26-2), which was obtained in Example 26.

FIG. 6 is a $^1$H-NMR chart of a calixarene compound (36-1), which was obtained in Example 36.

FIG. 7 is a $^1$H-NMR chart of a calixarene compound (37-1), which was obtained in Example 37.

DESCRIPTION OF EMBODIMENTS

The present invention will now be described in detail.

A calixarene compound of the present invention is a compound represented by structural formula (1) below. The calixarene compound contains, per molecule, at least one —CH$_2$OH group or phenolic hydroxy group and at least one carbon-carbon unsaturated bond.

[Chem. 2]

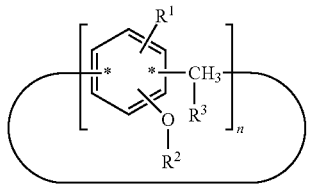
(1)

Here, R$^1$'s are a structural moiety (A), which has a —CH$_2$OH group; a structural moiety (B), which has a carbon-carbon unsaturated bond; a structural moiety (C), which has both a —CH$_2$OH group and a carbon-carbon unsaturated bond; a monovalent organic group (D), which is different from the structural moiety (A), the structural moiety (B), and the structural moiety (C) and has 1 to 20 carbon atoms; or a hydrogen atom (E). R$^2$'s are a structural moiety (A), which has a —CH$_2$OH group; a structural moiety (B), which has a carbon-carbon unsaturated bond; a structural moiety (C), which has both a —CH$_2$OH group and a carbon-carbon unsaturated bond; a monovalent organic group (D), which is different from the structural moiety (A), the structural moiety (B), and the structural moiety (C) and has 1 to 20 carbon atoms; or a hydrogen atom (E), provided that not all R$^2$'s are a hydrogen atom (E). R$^3$'s are one of a hydrogen atom, an optionally substituted aliphatic hydrocarbon group, and an optionally substituted aryl group. n is an integer of 2 to 10. R$^1$'s are identical to or different from one another, R$^2$'s are identical to or different from one another, and R$^3$'s are identical to or different from one another, per molecule. * is a point of attachment to an aromatic ring.

In structural formula (1), n is an integer of 2 to 10. In particular, it is preferable that n be 4, 6, or 8 because in such a case, structural stability is achieved and the structural characteristics of the calixarene compound become prominent. It is particularly preferable that n be 4.

In structural formula (1), R$^1$'s are a structural moiety (A), which has a —CH$_2$OH group; a structural moiety (B), which has a carbon-carbon unsaturated bond; a structural moiety (C), which has both a —CH$_2$OH group and a carbon-carbon unsaturated bond; a monovalent organic group (D), which is different from the structural moiety (A), the structural moiety (B), and the structural moiety (C) and has 1 to 20 carbon atoms; or a hydrogen atom (E). R$^1$'s present per molecule may have structures different from one another or may have an identical structure.

With regard to the structural moiety (A) that has a —CH$_2$OH group, the structural moiety (A) should have one or more —CH$_2$OH groups, and other specific structures thereof are not particularly limited. An example of the structural moiety (A) is, for example, a (poly)hydroxyalkyl group (A-1), which has a —CH$_2$OH group, a structural moiety represented by structural formula (A-2) below, or the like.

[Chem. 3]

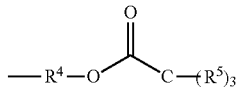
(A-2)

Here, R$^4$ is an aliphatic hydrocarbon group or a direct bond, and R$^5$'s are each independently one of a hydrogen atom, a hydroxy group, an alkyl group, and a (poly)hydroxyalkyl group. At least one of R$^5$'s is a group having a —CH$_2$OH group.

With regard to the (poly)hydroxyalkyl group (A-1), the alkyl group that serves as the backbone may be linear or branched, and the number of carbon atoms is not particularly limited. In particular, it is preferable that the number of carbon atoms be within a range of 1 to 20 because in such a case, the heat resistance and robustness of the calixarene compound are maintained, and excellent properties in terms of, for example, adhesion to a substrate are also achieved. More preferably, the range is 1 to 12. Furthermore, it is preferable that the number of hydroxy groups be within a range of 1 to 3. It is necessary that at least one of the hydroxy groups be a primary hydroxy group.

With regard to the structural moiety represented by structural formula (A-2), R$^4$ in structural formula (A-2) is an aliphatic hydrocarbon group or a direct bond. The aliphatic hydrocarbon group may be linear or branched. Furthermore, a cyclo ring structure may be included therein as a partial structure. In particular, it is preferable that R$^4$ be an alkyl group because in such a case, the heat resistance and robustness of the calixarene compound are maintained, and excellent properties in terms of, for example, adhesion to a substrate are also achieved. More preferably, R$^4$ is a linear alkyl group. Furthermore, the number of carbon atoms is preferably within a range of 1 to 12 and more preferably within a range of 1 to 6.

In structural formula (A-2), R$^5$'s are each independently one of a hydrogen atom, a hydroxy group, an alkyl group, and a (poly)hydroxyalkyl group. At least one of R$^5$'s is a group having a —CH$_2$OH group. The alkyl group may be linear or branched, and the number of carbon atoms is not particularly limited. In particular, it is preferable that the number of carbon atoms be within a range of 1 to 12 because in such a case, the heat resistance and robustness of the calixarene compound are maintained, and excellent properties in terms of, for example, adhesion to a substrate are also achieved. More preferably, the range is 1 to 6. The (poly)hydroxyalkyl group may be one similar to the (poly)hydroxyalkyl group (A-1). In particular, it is preferable that the number of carbon atoms be within a range of 1 to 12 because in such a case, the heat resistance and robustness of the calixarene compound are maintained, and excellent properties in terms of, for example, adhesion to a substrate are also achieved. More preferably, the range is 1 to 6. Furthermore, it is preferable that the number of hydroxy groups be within a range of 1 to 3. It is necessary that at least one of the hydroxy groups be a primary hydroxy group.

With regard to the structural moiety (B) that has a carbon-carbon unsaturated bond, the carbon-carbon unsaturated bond is specifically an ethylenic double bond or an acetylenic triple bond. The structural moiety (B) should have one or more such carbon-carbon unsaturated bonds, and other specific structures thereof are not particularly limited. An example of the specific structures is, for example, a vinyl group, a propargyl group, a (meth)acryloyl group, a (meth) acryloylamino group, a structural moiety represented by structural formula (B-1) or (B-2) below, or the like.

[Chem. 4]

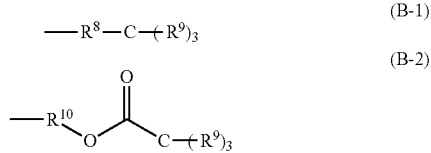

Here, $R^8$ and $R^{10}$ are each independently an aliphatic hydrocarbon group or a direct bond. $R^9$'s are each independently one of a hydrogen atom, an alkyl group, a vinyl group, a vinyloxy group, a vinyloxyalkyl group, an allyl group, an allyloxy group, an allyloxyalkyl group, a propargyl group, a propargyloxy group, a propargyloxyalkyl group, a (meth)acryloyl group, a (meth)acryloyloxy group, a (meth)acryloyloxyalkyl group, a (meth)acryloylamino group, and a (meth)acryloylaminoalkyl group. At least one of $R^9$'s is one of a vinyl group, a vinyloxy group, a vinyloxyalkyl group, an allyl group, an allyloxy group, an allyloxyalkyl group, a propargyl group, a propargyloxy group, a propargyloxyalkyl group, a (meth)acryloyl group, a (meth)acryloyloxy group, a (meth)acryloyloxyalkyl group, a (meth)acryloylamino group, and a (meth)acryloylaminoalkyl group.

In structural formulae (B-1) and (B-2), $R^8$ and $R^{10}$ are an aliphatic hydrocarbon group or a direct bond. The aliphatic hydrocarbon group may be linear or branched and may have an unsaturated bond in the structure. Furthermore, a cyclo ring structure may be included therein as a partial structure. In particular, it is preferable that $R^8$ and $R^{10}$ be a direct bond or an alkyl group because in such a case, the heat resistance and robustness of the calixarene compound are maintained, and excellent properties in terms of, for example, adhesion to a substrate are also achieved. The number of carbon atoms of the alkyl group is preferably within a range of 1 to 12 and more preferably within a range of 1 to 6.

In formulae (B-1) and (B-2), $R^9$'s are each independently one of a hydrogen atom, an alkyl group, a vinyl group, a vinyloxy group, a vinyloxyalkyl group, an allyl group, an allyloxy group, an allyloxyalkyl group, a propargyl group, a propargyloxy group, a propargyloxyalkyl group, a (meth) acryloyl group, a (meth)acryloyloxy group, a (meth)acryloyloxyalkyl group, a (meth)acryloylamino group, and a (meth)acryloylaminoalkyl group. At least one of $R^9$'s is one of a vinyl group, a vinyloxy group, a vinyloxyalkyl group, an allyl group, an allyloxy group, an allyloxyalkyl group, a propargyl group, a propargyloxy group, a propargyloxyalkyl group, a (meth)acryloyl group, a (meth)acryloyloxy group, a (meth)acryloyloxyalkyl group, a (meth)acryloylamino group, and a (meth)acryloylaminoalkyl group.

The alkyl group may be linear or branched, and the number of carbon atoms is not particularly limited. In particular, it is preferable that the number of carbon atoms be within a range of 1 to 12 because in such a case, the heat resistance and robustness of the calixarene compound are maintained, and excellent properties in terms of, for example, adhesion to a substrate are also achieved. More preferably, the range is 1 to 6.

In the vinyloxyalkyl group, the allyloxyalkyl group, the propargyloxyalkyl group, the (meth)acryloyloxyalkyl group, and the (meth)acryloylaminoalkyl group, the alkyl group may be linear or branched, and the number of carbon atoms is not particularly limited. In particular, it is preferable that the number of carbon atoms be within a range of 1 to 12 because in such a case, the heat resistance and robustness of the calixarene compound are maintained, and excellent properties in terms of, for example, adhesion to a substrate are also achieved. More preferably, the range is 1 to 6.

With regard to the structural moiety (C) that has both a —$CH_2OH$ group and a carbon-carbon unsaturated bond, the structural moiety (C) should have at least one —$CH_2OH$ group and at least one carbon-carbon unsaturated bond, and other specific structures thereof are not particularly limited. An example of the specific structures is, for example, a structural moiety represented by structural formula (C-1) or (C-2) below, or the like.

[Chem. 5]

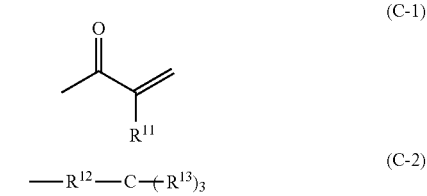

Here, $R^{11}$ is an alkyl group having a —$CH_2OH$ group. $R^{12}$ is an aliphatic hydrocarbon group or a direct bond. $R^{13}$'s are each independently one of a hydrogen atom, an alkyl group, an alkyl group having a —$CH_2OH$ group, a vinyl group, a vinyloxy group, a vinyloxyalkyl group, an allyl group, an allyloxy group, an allyloxyalkyl group, a propargyl group, a propargyloxy group, a propargyloxyalkyl group, a (meth) acryloyl group, a (meth)acryloyloxy group, a (meth)acryloyloxyalkyl group, a (meth)acryloylamino group, a (meth) acryloylaminoalkyl group, and a structural moiety represented by structural formula (C-2-1) below.

[Chem. 6]

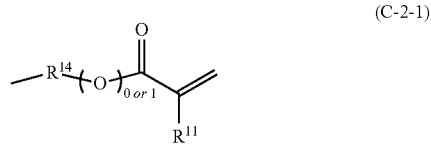

Here, $R^{14}$ is an aliphatic hydrocarbon group or a direct bond, and $R^{11}$ is an alkyl group having a —$CH_2OH$ group. At least one of $R^{13}$'s is an alkyl group having a —$CH_2OH$ group or a structural moiety represented by structural formula (C-2-1), and at least one of $R^{13}$'s is one of a vinyl group, a vinyloxy group, an allyl group, an allyloxy group, a propargyl group, a propargyloxy group, a (meth)acryloyl group, a (meth)acryloyloxy group, a (meth)acryloyloxyalkylene group, a (meth)acryloylamino group, a (meth)acryloylaminoalkylene group, and a structural moiety represented by structural formula (C-2-1).

With regard to $R^{11}$ in structural formula (C-1) and structural formula (C-2-1), the alkyl group having a —CH$_2$OH group may be one similar to the (poly)hydroxyalkyl group (A-1). In particular, it is preferable that the number of carbon atoms be within a range of 1 to 12 because in such a case, the heat resistance and robustness of the calixarene compound are maintained, and excellent properties in terms of, for example, adhesion to a substrate are also achieved. More preferably, the range is 1 to 6. Furthermore, it is preferable that the number of hydroxy groups be within a range of 1 to 3.

In structural formula (C-2), $R^{12}$ is an aliphatic hydrocarbon group or a direct bond. The aliphatic hydrocarbon group may be linear or branched and may have an unsaturated bond in the structure. Furthermore, a cyclo ring structure may be included therein as a partial structure. In particular, it is preferable that $R^{12}$ be an alkyl group because in such a case, the heat resistance and robustness of the calixarene compound are maintained, and excellent properties in terms of, for example, adhesion to a substrate are also achieved. The number of carbon atoms is preferably within a range of 1 to 12 and more preferably within a range of 1 to 6.

In structural formula (C-2), $R^{13}$'s are each independently one of a hydrogen atom, an alkyl group, an alkyl group having a —CH$_2$OH group, a vinyl group, a vinyloxy group, a vinyloxyalkyl group, an allyl group, an allyloxy group, an allyloxyalkyl group, a propargyl group, a propargyloxy group, a propargyloxyalkyl group, a (meth)acryloyl group, a (meth)acryloyloxy group, a (meth)acryloyloxyalkyl group, a (meth)acryloylamino group, a (meth)acryloylaminoalkyl group, and a structural moiety represented by structural formula (C-2-1).

With regard to $R^{13}$'s, the alkyl group may be linear or branched, and the number of carbon atoms is not particularly limited. In particular, it is preferable that the number of carbon atoms be within a range of 1 to 12 because in such a case, the heat resistance and robustness of the calixarene compound are maintained, and excellent properties in terms of, for example, adhesion to a substrate are also achieved. More preferably, the range is 1 to 6.

With regard to $R^{13}$'s, the alkyl group having a —CH$_2$OH group may be one similar to the (poly)hydroxyalkyl group (A-1). In particular, it is preferable that the number of carbon atoms be within a range of 1 to 12 because in such a case, the heat resistance and robustness of the calixarene compound are maintained, and excellent properties in terms of, for example, adhesion to a substrate are also achieved. More preferably, the range is 1 to 6. Furthermore, it is preferable that the number of hydroxy groups be within a range of 1 to 3.

With regard to $R^{13}$'s, the alkyl group in the vinyloxyalkyl group, the allyloxyalkyl group, the propargyloxyalkyl group, the (meth)acryloyloxyalkyl group, and the (meth)acryloylaminoalkyl group may be linear or branched, and the number of carbon atoms is not particularly limited. In particular, it is preferable that the number of carbon atoms be within a range of 1 to 12 because in such a case, the heat resistance and robustness of the calixarene compound are maintained, and excellent properties in terms of, for example, adhesion to a substrate are also achieved. More preferably, the range is 1 to 6.

In structural formula (C-2-1), $R^{14}$ is an aliphatic hydrocarbon group or a direct bond. The aliphatic hydrocarbon group may be linear or branched and may have an unsaturated bond in the structure. Furthermore, a cyclo ring structure may be included therein as a partial structure. In particular, it is preferable that $R^{14}$ be a direct bond or an alkyl group because in such a case, the heat resistance and robustness of the calixarene compound are maintained, and excellent properties in terms of, for example, adhesion to a substrate are also achieved. The number of carbon atoms of the alkyl group is preferably within a range of 1 to 12 and more preferably within a range of 1 to 6.

The monovalent organic group (D) that is different from the structural moiety (A), the structural moiety (B), and the structural moiety (C) and has 1 to 20 carbon atoms is not particularly limited and may be, for example, an aliphatic hydrocarbon group, a structural moiety formed of an aliphatic hydrocarbon group in which one or more hydrogen atoms are replaced with a halogen atom, or the like. The aliphatic hydrocarbon group may be linear or branched. Furthermore, a cyclo ring structure may be included therein as a partial structure. In particular, it is preferable that the monovalent organic group be an aliphatic hydrocarbon group because in such a case, the heat resistance and robustness of the calixarene compound are maintained, and excellent properties in terms of, for example, adhesion to a substrate are also achieved. The monovalent organic group is more preferably an alkyl group and particularly preferably a linear alkyl group. Furthermore, the number of carbon atoms is preferably within a range of 4 to 20 and particularly preferably within a range of 5 to 20.

In calixarene compounds of the present invention, the calixarene compounds should contain, per molecule, at least one —CH$_2$OH group or phenolic hydroxy group and at least one carbon-carbon unsaturated bond, and combinations of R and $R^2$ are not particularly limited. However, in calixarene compounds of the present invention, not all $R^2$'s per molecule are hydrogen atoms (E).

In structural formula (1), $R^3$'s are each independently one of a hydrogen atom, an optionally substituted aliphatic hydrocarbon group, and an optionally substituted aryl group. Some of the specific examples thereof include aliphatic hydrocarbon groups, such as alkyl groups, which include methyl groups, ethyl groups, propyl groups, isopropyl groups, butyl groups, t-butyl groups, pentyl groups, hexyl groups, cyclohexyl groups, heptyl groups, octyl groups, and nonyl groups; structural moieties including such an aliphatic hydrocarbon group and in which one or more hydrogen atoms are replaced with a hydroxy group, an alkoxy group, a halogen atom, or the like; aromatic-ring-containing hydrocarbon groups, such as phenyl groups, tolyl groups, xylyl groups, naphthyl groups, and anthryl groups; and structural moieties including such an aromatic-ring-containing hydrocarbon group and in which a substituent, such as a hydroxy group, an alkyl group, an alkoxy group, or a halogen atom, is attached to the aromatic nucleus. In particular, it is preferable that $R^3$'s be a hydrogen atom.

The location of the point of attachment represented by * in structural formula (1) is not particularly limited, and any structure is possible. In particular, calixarene compounds represented by structural formula (1-1) or (1-2) below are preferable because in such calixarene compounds, heat resistance and robustness are maintained, and excellent properties in terms of, for example, adhesion to a substrate are also achieved, and further because there is an advantage in terms of production. In compounds represented by these structural formulae, functional groups having conflicting properties, such as hydrophobicity and hydrophilicity or reactivity and non-reactivity, are disposed opposite to each other with respect to the benzene ring; this configuration makes it possible to significantly improve the surface functionality of resulting cured products while ensuring adhesion to a substrate. Hence, the compounds have enhanced industrial usefulness.

[Chem. 7]

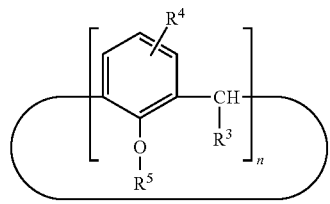

(1-1)

Here, $R^4$'s are a monovalent organic group (d1), which is represented by —X—R where X is a direct bond or a carbonyl group, and R is a hydrogen atom or an aliphatic hydrocarbon group having 1 to 20 carbon atoms. $R^5$'s are a structural moiety (A), which has a —CH$_2$OH group; a structural moiety (B), which has a carbon-carbon unsaturated bond; a structural moiety (C), which has both a —CH$_2$OH group and a carbon-carbon unsaturated bond; or a hydrogen atom (E), provided that not all $R^5$'s are a hydrogen atom (E). $R^3$'s are as described above. n is an integer of 2 to 10. $R^4$'s are identical to or different from one another, $R^5$'s are identical to or different from one another, and $R^3$'s are identical to or different from one another, per molecule.

[Chem. 8]

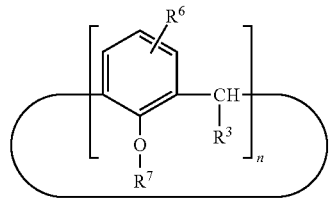

(1-2)

Here, $R^6$'s are a structural moiety (A), which has a —CH$_2$OH group; a structural moiety (B), which has a carbon-carbon unsaturated bond; or a structural moiety (C), which has both a —CH$_2$OH group and a carbon-carbon unsaturated bond. $R^7$'s are an aliphatic hydrocarbon group (d2), which has 1 to 20 carbon atoms. $R^3$'s are as described above. n is an integer of 2 to 10. $R^6$'s are identical to or different from one another, $R^7$'s are identical to or different from one another, and $R^3$'s are identical to or different from one another, per molecule.

Compounds represented by structural formula (1-1) are compounds in which $R^4$'s, which are relatively hydrophobic functional groups, are present in an upper region, and reactive functional groups are present in a lower region, in the structural formula. One or more phenolic hydroxy groups may be present, that is, $R^2$'s may be one or more hydrogen atoms (E); however, in the case where all $R^2$'s in the compound are phenolic hydroxy groups, properties such as adhesion to a substrate become insufficient, and, therefore, some of $R^5$'s need to be one of a structural moiety (A), which has a —CH$_2$OH group, a structural moiety (B), which has a carbon-carbon unsaturated bond, and a structural moiety (C), which has both a —CH$_2$OH group and a carbon-carbon unsaturated bond.

$R^4$'s in structural formula (1-1) is a monovalent organic group (d1), which is represented by —X—R where X is a direct bond or a carbonyl group, and R is a hydrogen atom or an aliphatic hydrocarbon group having 1 to 20 carbon atoms. The aliphatic hydrocarbon group may be linear or branched. A cyclo ring structure may be included therein as a partial structure. It is preferable that the aliphatic hydrocarbon group be a linear alkyl group. Furthermore, the number of carbon atoms is more preferably within a range of 4 to 20 and particularly preferably within a range of 5 to 20. The position of attachment of $R^4$'s to the aromatic rings is not particularly limited. However, the position may be a para position relative to the position of attachment of the —O—$R^5$ groups; this configuration is particularly preferable from the standpoint of enabling the effects of the present invention to be produced more easily and achieving an advantage in a production method.

$R^5$'s in structural formula (1-1) correspond to $R^2$'s, described above. Those preferred as $R^2$'s are also preferred as $R^5$'s.

Compounds represented by structural formula (1-2) are compounds in which $R^7$'s, which are hydrophobic functional groups, are present in a lower region, and $R^6$'s, which are reactive functional groups, are present in an upper region, in the structural formula.

$R^7$'s in structural formula (1-2) are an aliphatic hydrocarbon group (d2), which has 1 to 20 carbon atoms and may be linear or branched. A cyclo ring structure may be included therein as a partial structure. It is preferable that the aliphatic hydrocarbon group be a linear alkyl group. Furthermore, the number of carbon atoms is more preferably within a range of 4 to 20 and particularly preferably within a range of 5 to 20.

$R^6$'s in structural formula (1-2) correspond to $R^1$'s, described above. Those preferred as $R^1$'s are also preferred as $R^6$'s. The position of attachment of $R^6$'s to the aromatic rings is not particularly limited. However, the position may be a para position relative to the position of attachment of the —O—$R^7$ groups; this configuration is particularly preferable from the standpoint of enabling the effects of the present invention to be produced more easily and achieving an advantage in a production method.

Calixarene compounds of the present invention may be produced by any method. Examples of methods for producing calixarene compounds of the present invention will be described below.

A method for introducing the substituents $R^1$'s and $R^2$'s of structural formula (1) is as follows, for example. Structural moieties (A), (B), (C), or (D) that serve as $R^1$'s are introduced into an intermediate (α), which is represented by structural formula (2) below.

[Chem. 9]

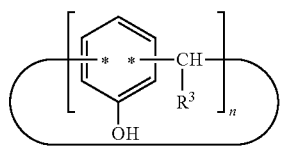

(2)

Here, $R^3$'s, n, and * are as described above. Subsequently, some or all of the hydrogen atoms of the phenolic hydroxy groups are replaced with one or more of structural moieties (A), (B), (C), and (D) to introduce structural moieties that serve as R²'s. Alternatively, the phenolic hydroxy group may be modified first, and thereafter one or more of structural moieties (A), (B), (C), and (D) may be introduced.

The intermediate (α) represented by structural formula (2) can be produced by using, for example, a method of direct production from phenol and an aldehyde compound or a method in which an intermediate (α), which has a calixarene structure, is obtained by reacting a para-alkyl phenol with an aldehyde compound, and thereafter dealkylation is performed in the presence of phenol and aluminum chloride. In particular, in terms of enabling higher yield production of the intermediate (α), it is preferable that the production be performed using the method in which an intermediate (a), which has a calixarene structure, is obtained by reacting a para-alkyl phenol with an aldehyde compound, and thereafter dealkylation is performed in the presence of phenol and aluminum chloride.

Methods for introducing, as R¹, a monovalent organic group (d1) into the intermediate (α) are described. The monovalent organic group (d1) is an example of the monovalent organic group (D) that is different from the structural moiety (A), the structural moiety (B), and the structural moiety (C) and has 1 to 20 carbon atoms. The monovalent organic group (d1) is represented by —X—R where X is a direct bond or a carbonyl group, and R is a hydrogen atom or an aliphatic hydrocarbon group having 1 to 20 carbon atoms. Examples of the methods include a method in which a Friedel-Crafts alkylation reaction is used and a method in which an acyl group is introduced via a Friedel-Crafts acylation reaction. Furthermore, the carbonyl group of the acyl group may be reduced to form an aliphatic hydrocarbon group. The Friedel-Crafts reactions can be carried out using a common method, examples of which include a method in which a reaction with a corresponding halide is caused in the presence of a Lewis acid catalyst, such as aluminum chloride. The reduction of the carbonyl group can be carried out using a common method, such as a Wolff-Kishner reduction reaction.

In the present invention, calixarene compounds are compounds containing, per molecule, at least one —CH₂OH group or phenolic hydroxy group and at least one carbon-carbon unsaturated bond. For such compounds, structural moieties (A), (B), and/or (C) may be introduced as R¹'s, which are substituents on the aromatic rings, by using, for instance, the following method. For example, in a case where a structural moiety (A), which has a —CH₂OH group, is to be present on one or more of the aromatic rings present per molecule, and a structural moiety (B), which has a carbon-carbon unsaturated bond, is to be present on one or more of the aromatic rings, it is possible to introduce structural moieties (A) into a plurality or all of the aromatic rings present per molecule and thereafter convert some of the structural moieties (A) into one or more structural moieties (B).

A method for introducing structural moieties (A), (B), and/or (C) as R¹'s, which are substituents on the aromatic rings, may be the following method, for example. An intermediate (β), represented by structural formula (3) below, is obtained.

[Chem. 10]

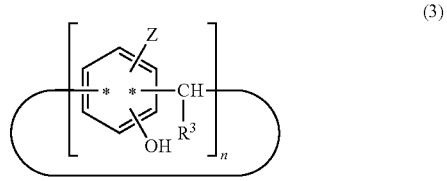

(3)

Here, R³'s, n, and * are as described above, and Zs are functional groups for introducing the R¹ groups). Subsequently, the Z groups are modified into one or more of structural moieties (A), (B), and (C).

In the intermediate (β), the Z groups are not particularly limited provided that the Z groups are functional groups that can be converted into structural moieties (A), (B), and/or (C). In a case where the Z groups are allyl groups, the desired intermediate (β) can be obtained with high efficiency from an allylic etherification product of the intermediate (α), which is known to undergo a transfer reaction as shown below in the presence of a large excess of an amine compound.

[Chem. 11]

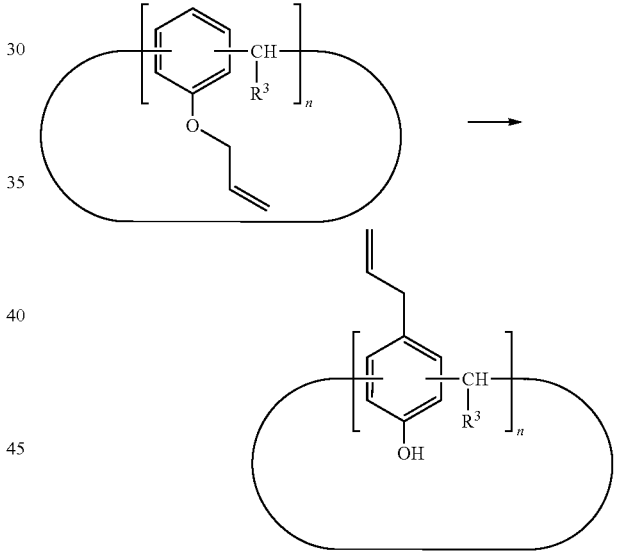

The allylic etherification of the intermediate (α) can be accomplished by reacting the intermediate (α) with a halogenated allyl under basic catalyst conditions, in a manner similar to that for a so-called Williamson ether synthesis. The amine compound that is used in the transfer reaction is not particularly limited. Examples of the amine compound include tertiary amines, such as N,N-dimethylaniline, N,N-diethylaniline, N,N,N-trimethylamine, N,N,N-triethylamine, and diisopropylethylamine, and secondary amines, such as N,N-dimethylamine and N,N-diethylamine. These may be used alone or in a combination of two or more.

Methods for replacing the allyl groups of the intermediate (β) with one or more of structural moieties (A), (B), and (C) are not particularly limited. Specific examples of simplest methods are as follows. By using a Brown hydroboration reaction in which a borane compound and hydrogen peroxide are reacted with an allyl group, primary alcoholic hydroxy groups are formed. For some of the primary alcoholic hydroxy groups, in one method, an esterification reaction is caused between the primary alcoholic hydroxy groups and a carbon-carbon unsaturated bond-containing carboxylic acid compound, such as (meth)acrylic acid, under neutral conditions, by using N,N'-dicyclohexylcarbodiimide or a Mitsunobu reagent including diethyl azodicarboxylate and triphenylphosphine; and, in another method, an esterification reaction is caused between the hydroxy groups and a carbon-carbon unsaturated bond-containing carboxylic acid halide, such as (meth)acrylic acid chloride, in the presence of a base.

The borane compound is not particularly limited. Examples of the borane compound include borabicyclo [3.3.1]nonane (9-BBN), diborane, disiamylborane, thexylborane, dicyclohexylborane, catecholborane, and pinacolborane.

In a case where the Z groups in the intermediate ((3) are halomethyl groups, primary alcoholic hydroxy groups can be formed in the following manner. It is known that a halomethylation product of the intermediate ($\alpha$) is formed from a reaction between an acid halide and a formalin derivative. Thus, a halomethylation product that serves as the intermediate ($\beta$) may be acyloxylated by being reacted with a metal salt of an organic carboxylic acid in the presence of a quaternary ammonium salt, and then the product may be hydrolyzed by using a metal hydroxide or the like. Furthermore, in a case where the Z groups in the intermediate ($\beta$) are formyl groups, primary alcoholic hydroxy groups can be formed by reducing a formylation product of the intermediate ($\alpha$) by using a reduction agent. Primary alcoholic hydroxy groups formed in these manners can also be replaced with one or more of structural moieties (B) and (C) by utilizing an esterification reaction as described above.

[Chem. 12]

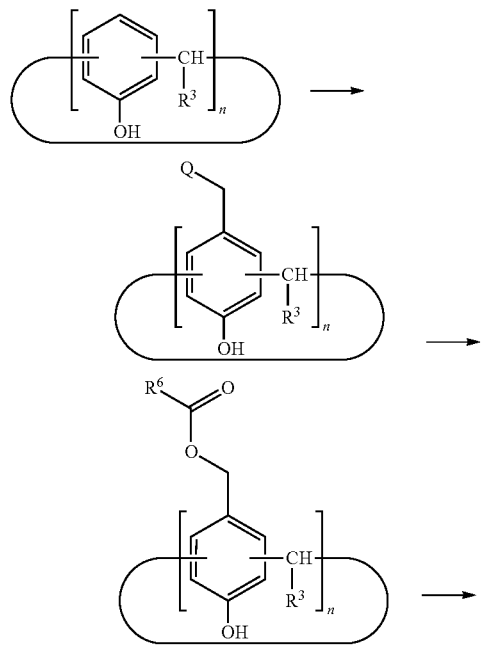

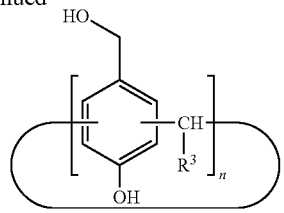

Q represents a halogen atom, such as a chlorine atom, a bromine atom, or an iodine atom, and $R^6$ represents an alkyl group or alkylene group having 1 to 4 carbon atoms.

Methods for the halomethylation are not particularly limited. Examples of the methods include a method in which chloromethylation is achieved by causing paraformaldehyde and hydrogen chloride to act in an acetic acid solvent and a method in which bromomethylation is achieved under the same conditions except that hydrogen bromide is caused to act instead of hydrogen chloride. Furthermore, the quaternary ammonium salt that is used in the acyloxylation is not particularly limited. Examples thereof include tetrabutylammonium bromide, benzyltributylammonium bromide, benzyltrimethylammonium bromide, benzyltributylammonium bromide, tetraethylammonium bromide, benzyltriethylammonium chloride, benzyltrimethylammonium chloride, benzyltributylammonium chloride, tetraethylammonium chloride, methyl tributyl ammonium chloride, and tetrabutylammonium chloride. Furthermore, the organic carboxylic acid is not particularly limited. Examples thereof include sodium acetate, potassium acetate, sodium propionate, potassium propionate, sodium acrylate, potassium acrylate, sodium methacrylate, and potassium methacrylate.

[Chem. 13]

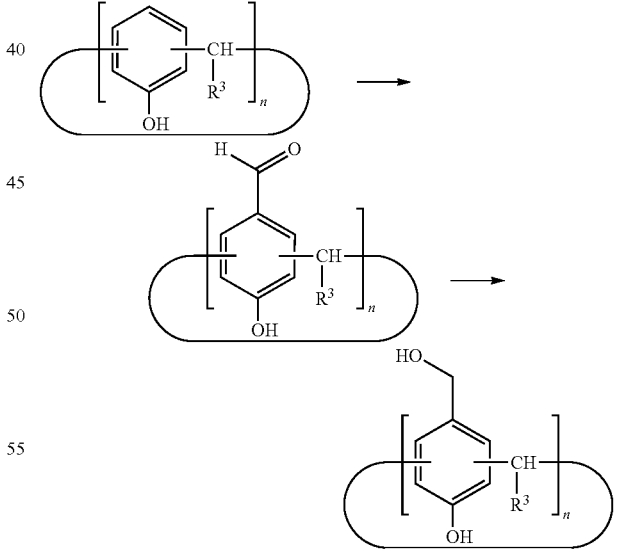

Methods for the formylation are not particularly limited. Examples of the methods include a common method of a Vilsmeier-Haack reaction, in which N,N-dimethylformamide and phosphorus oxychloride are caused to act, and a common method of a Duff reaction, in which formylation is carried out by activating hexamethylenetetramine with acid. Methods for reducing the resulting formyl product are not particularly limited. Examples of the methods include a common method of catalytic reduction using hydrogen, which is performed in the presence of a metal hydride, such as sodium borohydride or lithium aluminum hydride, or a metal catalyst, such as palladium.

Methods for modifying some or all of the phenolic hydroxy groups to structural moieties (A), (B), (C), or (D) after introducing $R^1$'s as substituents, which are present in the intermediate ($\alpha$) or the intermediate ($\beta$) or on the aromatic rings, are also not particularly limited; a typical reaction for phenolic hydroxy groups known in the art, such as a Mitsunobu reaction or a Williamson ether synthesis, may be appropriately applied.

In the present invention, calixarene compounds are compounds containing, per molecule, at least one —CH$_2$OH group or phenolic hydroxy group and at least one carbon-carbon unsaturated bond. Methods for obtaining such a compound are, for instance, as follows. For example, a case is considered in which one or more of the phenolic hydroxy groups present per molecule are structural moieties (A), which have a —CH$_2$OH group, and one or more of the phenolic hydroxy groups are structural moieties (B), which have a carbon-carbon unsaturated bond. $R^1$'s are introduced as substituents, which are present in the intermediate ($\alpha$) or ($\beta$) or on the aromatic rings. Thereafter, in one method, a structural moiety (B) is introduced to some of the phenolic hydroxy groups, and a structural moiety (A) is introduced to the remaining one or more phenolic hydroxy groups, or, in another method, a structural moiety (A) is introduced to all of the phenolic hydroxy groups, and thereafter some of the structural moieties (A) are converted into one or more structural moieties (B).

In a case where the phenolic hydroxy group is modified into a substituent that includes a structural moiety (B), which has a carbon-carbon unsaturated bond, it is possible to utilize a Mitsunobu reaction in which an alcoholic-hydroxy-group-containing compound corresponding to the structural moiety (B) is used. In this manner, efficient production can be achieved. Examples of the alcoholic-hydroxy-group-containing compound include hydroxyethyl (meth)acrylate, hydroxypropyl (meth)acrylate, glycerol di(meth)acrylate, trimethylolpropane dimethacrylate, pentaerythritol tri(meth)acrylate, dipentaerythritol penta(meth)acrylate, hydroxyethyl (meth)acrylamide, hydroxypropyl (meth)acrylamide, hydroxyethyl vinyl ether, and hydroxypropyl vinyl ether. For $R^2$'s of structural formula (1), the structural moiety (B) to hydrogen atom (E) ratio can be appropriately adjusted with a reaction molar ratio.

Methods for introducing a structural moiety (A) to the phenolic hydroxy group include the following, for example: a method in which a corresponding halogenated silyl etherification product is reacted in a manner of a Williamson ether synthesis, and thereafter the product is desilylated in the presence of tetrabutylammonium fluoride; and a method in which a ketone structure or an ester structure is introduced by reacting an appropriate halide, and thereafter the product is reduced to alcohol. Furthermore, a structural moiety (A) having a more complex structure can be introduced by using, for example, the following method or the like; a silyl-ether-group-containing nucleophilic compound, such as a carboxylic acid compound, is additionally introduced into an already introduced structural moiety (A) via a Mitsunobu reaction, and the product is desilylated.

Methods for converting some of the structural moieties (A) into one or more structural moieties (B), which have a carbon-carbon unsaturated bond, include the following, for example: a method in which a Mitsunobu reaction that uses a nucleophilic compound having a partial structure corresponding to a structural moiety (B), such as a carbon-carbon unsaturated bond-containing carboxylic acid compound, is utilized; and a method in which an electrophilic compound having a partial structure corresponding to a structural moiety (B), such as a carbon-carbon unsaturated bond-containing carboxylic acid halide, is esterified in the presence of a base.

In a calixarene compound of the present invention, in a case where $R^2$'s of structural formula (1) are structural moieties (C), which have both a —CH$_2$OH group and a carbon-carbon unsaturated bond, examples of the methods include the following: a method in which $R^1$'s are introduced as substituents, which are present in the intermediate ($\alpha$) or ($\beta$) or on the aromatic rings, and thereafter a halide corresponding to a structural moiety (C) is reacted with some or all of the phenolic hydroxy groups; a method in which $R^1$'s are introduced as substituents, which are present in the intermediate ($\alpha$) or ($\beta$) or on the aromatic rings, and thereafter a structural moiety having a carbon-carbon unsaturated bond and a silyl ether group is introduced to some or all of the phenolic hydroxy groups, and further, the product is desilylated; and a method in which $R^1$'s are introduced as substituents, which are present in the intermediate ($\alpha$) or ($\beta$) or on the aromatic rings, thereafter a structural moiety having a plurality of hydroxy groups is introduced to some or all of the phenolic hydroxy groups, and further, some of the hydroxy groups are replaced with a carbon-carbon unsaturated bond-containing structure.

Methods for introducing a structural moiety having a carbon-carbon unsaturated bond and a silyl ether group to the phenolic hydroxy groups after introducing $R^1$'s as substituents, which are present in the intermediate ($\alpha$) or ($\beta$) or on the aromatic rings, include the following, for example: a method in which a corresponding halogenated silyl etherification product is reacted in a manner of a Williamson ether synthesis as described above; and a method in which, after structural moieties (A) are first introduced, a nucleophilic compound having a silyl ether group, such as a carboxylic acid compound, is introduced via a Mitsunobu reaction.

Methods for introducing a structural moiety having a plurality of hydroxy groups to the phenolic hydroxy groups after introducing $R^1$'s as substituents, which are present in the intermediate ($\alpha$) or ($\beta$) or on the aromatic rings, include the following, for example: a method in which a structural moiety having a plurality of silyl ether groups is introduced in the manner described above, and thereafter the product is desilylated; and a method in which a halide having an acetal structure is reacted, and thereafter the product is deacetalized. Methods for replacing some of the hydroxy groups with a carbon-carbon unsaturated bond-containing structure include a method in which a carbon-carbon unsaturated bond-containing halide is reacted. In this case, some of the hydroxy groups may be protected by, for example, silyl ether formation.

Methods for introducing an aliphatic hydrocarbon group (d2), which has 1 to 20 carbon atoms and serves as the structural moiety (D), to the phenolic hydroxy groups include, for example, a method in which a halide of the relevant aliphatic hydrocarbon is reacted under basic catalyst conditions in a manner similar to that for the so-called Williamson ether synthesis.

In the above description, methods for producing calixarene compounds of the present invention are described with some specific examples. However, calixarene compounds of the present invention are not limited to the compounds that can be obtained in the specific production methods described above. For example, elementary reactions presented above may be, for instance, appropriately combined or repeatedly conducted. Accordingly, calixarene compounds having more diverse and complex molecular structures can be obtained.

Calixarene compounds of the present invention retain properties characterizing calixarene compounds, such as excellent heat resistance and hardness, and moreover have excellent characteristics in terms of, for example, adhesion to a substrate and toughness, which have been difficult to achieve in calixarene compounds of the related art. Uses of calixarene compounds of the present invention are not particularly limited, and application to various uses is possible. Some of the application examples are presented below.

Calixarene compounds of the present invention have at least one carbon-carbon unsaturated bond per molecule and, therefore, can be utilized as a curable resin material with the carbon-carbon unsaturated bond serving as a polymerizable group. The type of the curing may be photocuring or thermal curing, but the following description describes a case in which the compounds are used as a photocurable material.

In the case where a calixarene compound of the present invention is used as a photocurable resin material, it is preferable that the material be a curable composition including a photopolymerization initiator, which will be described later, an additional photocurable composition, and any of a variety of additives, for example. The additional photocurable compound may be a (meth)acryloyl-group-containing compound or the like. Examples of the (meth)acryloyl-group-containing compound include mono(meth)acrylate compounds and modified products thereof (R1), aliphatic-hydrocarbon-type poly(meth)acrylate compounds and modified products thereof (R2), alicyclic poly(meth)acrylate compounds and modified products thereof (R3), aromatic poly(meth)acrylate compounds and modified products thereof (R4), (meth)acrylate resins having a silicone chain and modified products thereof (R5), epoxy (meth)acrylate resins and modified products thereof (R6), urethane (meth)acrylate resins and modified products thereof (R7), acrylic (meth)acrylate resins and modified products thereof (R8), and dendrimer-type (meth)acrylate resins and modified products thereof (R9).

Examples of the mono(meth)acrylate compounds and modified products thereof (R1) include the following mono(meth)acrylate compounds: aliphatic mono(meth)acrylate compounds, such as methyl (meth)acrylate, ethyl (meth)acrylate, hydroxyethyl (meth)acrylate, propyl (meth)acrylate, hydroxypropyl (meth)acrylate, butyl (meth)acrylate, and 2-ethylhexyl (meth)acrylate; alicyclic mono(meth)acrylate compounds, such as cyclohexyl (meth)acrylate, isobornyl (meth)acrylate, and adamantyl mono(meth)acrylate; heterocyclic mono(meth)acrylate compounds, such as glycidyl (meth)acrylate and tetrahydrofurfuryl acrylate; aromatic mono(meth)acrylate compounds, such as phenyl (meth)acrylate, benzyl (meth)acrylate, phenoxy (meth)acrylate, phenoxy ethyl (meth)acrylate, phenoxy ethoxy ethyl (meth)acrylate, 2-hydroxy-3-phenoxypropyl (meth)acrylate, phenylphenol (meth)acrylate, phenyl benzyl (meth)acrylate, phenoxy benzyl (meth)acrylate, benzylbenzyl (meth)acrylate, phenyl phenoxy ethyl (meth)acrylate, and para-cumylphenol (meth)acrylate; and compounds represented by structural formula (5) below.

[Chem. 14]

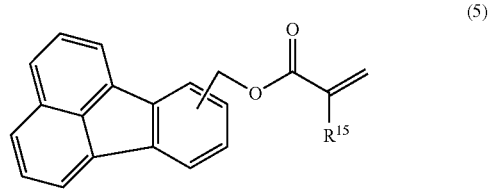

(5)

Here, $R^{15}$ is a hydrogen atom or a methyl group. Further examples include (poly)oxyalkylene-modified products of the above-mentioned various mono(meth)acrylate compounds, the products having a (poly)oxyalkylene chain, such as a (poly)oxyethylene chain, a (poly)oxypropylene chain, or a (poly)oxytetramethylene chain, introduced in the molecular structure; and lactone-modified products of the above-mentioned various mono(meth)acrylate compounds, the products having a (poly)lactone structure introduced in the molecular structure.

Examples of the aliphatic-hydrocarbon-type poly(meth)acrylate compounds and modified products thereof (R2) include aliphatic di(meth)acrylate compounds, such as ethylene glycol di(meth)acrylate, propylene glycol di(meth)acrylate, butanediol di(meth)acrylate, and hexanediol di(meth)acrylate, and neopentyl glycol di(meth)acrylate; aliphatic tri(meth)acrylate compounds, such as trimethylolpropane tri(meth)acrylate, glycerol tri(meth)acrylate, pentaerythritol tri(meth)acrylate, ditrimethylolpropane tri(meth)acrylate, and dipentaerythritol tri(meth)acrylate; and tetra- or higher functional aliphatic poly(meth)acrylate compounds, such as pentaerythritol tetra(meth)acrylate, ditrimethylolpropane tetra(meth)acrylate, dipentaerythritol tetra(meth)acrylate, dipentaerythritol penta(meth)acrylate, and dipentaerythritol hexa(meth)acrylate. Further examples include (poly)oxyalkylene-modified products of the above-mentioned various aliphatic-hydrocarbon-type poly(meth)acrylate compounds, the products having a (poly)oxyalkylene chain, such as a (poly)oxyethylene chain, a (poly)oxypropylene chain, or a (poly)oxytetramethylene chain, introduced in the molecular structure; and lactone-modified products of the above-mentioned various aliphatic-hydrocarbon-type poly(meth)acrylate compounds, the products having a (poly)lactone structure introduced in the molecular structure.

Examples of the alicyclic poly(meth)acrylate compounds and modified products thereof (R3) include alicyclic di(meth)acrylate compounds, such as 1,4-cyclohexanedimethanol di(meth)acrylate, norbornane di(meth)acrylate, norbornane dimethanol di(meth)acrylate, dicyclopentanyl di(meth)acrylate, and tricyclodecane dimethanol di(meth)acrylate. Further examples include (poly)oxyalkylene-modified products of the above-mentioned various alicyclic poly(meth)acrylate compounds, the products having a (poly)oxyalkylene chain, such as a (poly)oxyethylene chain, a (poly)oxypropylene chain, or a (poly)oxytetramethylene chain, introduced in the molecular structure; and lactone-modified products of the above-mentioned various alicyclic poly(meth)acrylate compounds, the products having a (poly)lactone structure introduced in the molecular structure.

Examples of the aromatic poly(meth)acrylate compounds and modified products thereof (R4) include aromatic di(meth)acrylate compounds. Examples thereof include biphenol di(meth)acrylate, bisphenol di(meth)acrylate, bicarbazole compounds represented by structural formula (9) below, and fluorene compounds.

[Chem. 15]

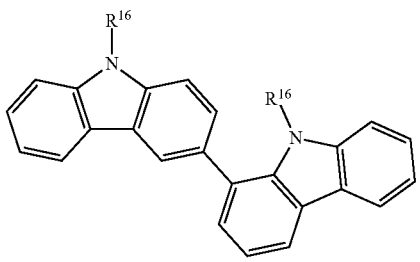

(6)

Here, $R^{16}$'s are each independently one of a (meth)acryloyl group, a (meth)acryloyloxy group, and a (meth)acryloyloxyalkyl group. The fluorene compounds are represented by structural formula (7-1) or (7-2) below.

[Chem. 16]

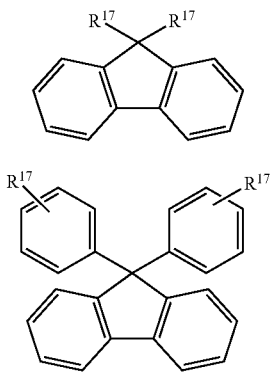

(7-1)

(7-2)

Here, $R^{17}$'s are each independently one of a (meth)acryloyl group, a (meth)acryloyloxy group, and a (meth)acryloyloxyalkyl group. Further examples include (poly)oxyalkylene-modified products of the above-mentioned various aromatic poly(meth)acrylate compounds, the products having a (poly)oxyalkylene chain, such as a (poly)oxyethylene chain, a (poly)oxypropylene chain, or a (poly)oxytetramethylene chain, introduced in the molecular structure; and lactone-modified products of the above-mentioned various aromatic poly(meth)acrylate compounds, the products having a (poly)lactone structure introduced in the molecular structure.

The (meth)acrylate resins having a silicone chain and modified products thereof (R5) are not particularly limited provided that the resins and modified products are compounds having a silicone chain and a (meth)acryloyl group in the molecular structure; therefore, any of a variety of compounds may be used. Furthermore, production methods therefor are not particularly limited. Specific examples of the (meth)acrylate resins having a silicone chain and modified products thereof (R5) include a reaction product of an alkoxy-silane-group-containing silicone compound and a hydroxy-group-containing (meth)acrylate compound.

Examples of the alkoxy-silane-group-containing silicone compound include commercially available products, examples of which include X-40-9246 (alkoxy group content: 12 mass %), KR-9218 (alkoxy group content: 15 mass %), X-40-9227 (alkoxy group content: 15 mass %), KR-510 (alkoxy group content: 17 mass %), KR-213 (alkoxy group content: 20 mass %), X-40-9225 (alkoxy group content: 24 mass %), X-40-9250 (alkoxy group content: 25 mass %), KR-500 (alkoxy group content: 28 mass %), KR-401N (alkoxy group content: 33 mass %), KR-515 (alkoxy group content: 40 mass %), and KC-89S (alkoxy group content: 45 mass %), manufactured by Shin-Etsu Chemical Co., Ltd. These may be used alone or in a combination of two or more. In particular, it is preferable that the alkoxy group content be within a range of 15 to 40 mass %. Furthermore, in the case where two or more silicone compounds are used in combination, it is preferable that the average of the alkoxy group contents be within a range of 15 to 40 mass %.

Examples of the hydroxy-group-containing (meth)acrylate compound include hydroxy-group-containing (meth)acrylate compounds, such as hydroxyethyl (meth)acrylate, hydroxypropyl (meth)acrylate, trimethylolpropane di(meth)acrylate, pentaerythritol tri(meth)acrylate, ditrimethylolpropane tri(meth)acrylate, and dipentaerythritol penta(meth)acrylate. Further examples include (poly)oxyalkylene-modified products of the above-mentioned various hydroxy-group-containing (meth)acrylate compounds, the products having a (poly)oxyalkylene chain, such as a (poly)oxyethylene chain, a (poly)oxypropylene chain, or a (poly)oxytetramethylene chain, introduced in the molecular structure; and lactone-modified products of the above-mentioned various hydroxy-group-containing (meth)acrylate compounds, the products having a (poly)lactone structure introduced in the molecular structure.

Furthermore, examples of the (meth)acrylate resins having a silicone chain and modified products thereof (R5) include the following commercially available products. An example is a silicone oil having a (meth)acryloyl group at one end, examples of which include X-22-174ASX (methacryloyl group equivalent weight: 900 g/eq.), X-22-174BX (methacryloyl group equivalent weight: 2,300 g/eq.), X-22-174DX (methacryloyl group equivalent weight: 4,600 g/eq.), KF-2012 (methacryloyl group equivalent weight: 4,600 g/eq.), X-22-2426 (methacryloyl group equivalent weight: 12,000 g/eq.), X-22-2404 (methacryloyl group equivalent weight: 420 g/eq.), and X-22-2475 (methacryloyl group equivalent weight: 420 g/eq.), manufactured by Shin-Etsu Chemical Co., Ltd. Another example is a silicone oil having a (meth)acryloyl group at both ends, examples of which include X-22-164 (methacryloyl group equivalent weight: 190 g/eq.), X-22-164AS (methacryloyl group equivalent weight: 450 g/eq.), X-22-164A (methacryloyl group equivalent weight: 860 g/eq.), X-22-164B (methacryloyl group equivalent weight: 1,600 g/eq.), X-22-164C (methacryloyl group equivalent weight: 2,400 g/eq.), X-22-164E (methacryloyl group equivalent weight: 3,900 g/eq.), and X-22-2445 (acryloyl group equivalent weight: 1,600 g/eq.), manufactured by Shin-Etsu Chemical Co., Ltd. Another example is an oligomer-type silicone compound having a plurality of (meth)acryloyl groups per molecule, examples of which include KR-513 (methacryloyl group equivalent weight: 210 g/eq.) and -40-9296 (methacryloyl group equivalent weight: 230 g/eq.), manufactured by Shin-Etsu Chemical Co., Ltd., and AC-SQ TA-100 (acryloyl group equivalent weight: 165 g/eq.), AC-SQ SI-20 (acryloyl group equivalent weight: 207 g/eq.), MAC-SQ TM-100 (methacryloyl group equivalent weight: 179 g/eq.), MAC-SQ SI-20 (methacryloyl group equivalent weight: 224 g/eq.), and MAC-SQ HDM (methacryloyl group equivalent weight: 239 g/eq.), manufactured by Toagosei Co., Ltd.

It is preferable that the (meth)acrylate resins having a silicone chain and modified products thereof (R5) have a weight average molecular weight (Mw) within a range of 1,000 to 10,000; more preferably, the range is 1,000 to 5,000. Furthermore, it is preferable that the (meth)acryloyl group equivalent weight thereof be within a range of 150 to 5,000 g/eq.; more preferably, the range is 150 to 2,500 g/eq.

Examples of the epoxy (meth)acrylate resins and modified products thereof (R6) include products obtained by reacting an epoxy resin with (meth)acrylic acid or an anhydride thereof. Examples of the epoxy resin include diglycidyl ethers of a dihydric phenol, such as hydroquinone or catechol; diglycidyl ethers of a biphenol compound, such as 3,3'-biphenyldiol or 4,4'-biphenyldiol; bisphenol type epoxy resins, such as bisphenol A epoxy resins, bisphenol B epoxy resins, bisphenol F epoxy resins, and bisphenol S epoxy resins; polyglycidyl ethers of a naphthol compound, such as 1,4-naphthalenediol, 1,5-naphthalenediol, 1,6-naphthalenediol, 2,6-naphthalenediol, 2,7-naphthalenediol, binaphthol, or bis(2,7-dihydroxynaphthyl)methane; triglycidyl ethers, such as 4,4'4"-methylidynetrisphenol; and novolac type epoxy resins, such as phenol novolac epoxy resins and cresol novolac resins. Further examples include (poly)oxyalkylene-modified products of the above-mentioned various epoxy resins, the products having a (poly)oxyalkylene chain, such as a (poly)oxyethylene chain, a (poly)oxypropylene chain, or a (poly)oxytetramethylene chain, introduced in the molecular structure; and lactone-modified products of the above-mentioned epoxy resins, the products having a (poly)lactone structure introduced in the molecular structure.

Examples of the urethane (meth)acrylate resins and modified products thereof (R7) include products obtained by reacting any of a variety of polyisocyanate compounds with any of various hydroxy-group-containing (meth)acrylate compounds and, if necessary, any of various polyol compounds. Examples of the polyisocyanate compounds include aliphatic diisocyanate compounds, such as butane diisocyanate, hexamethylene diisocyanate, 2,2,4-trimethylhexamethylene diisocyanate, and 2,4,4-trimethylhexamethylene diisocyanate; alicyclic diisocyanate compounds, such as norbornane diisocyanate, isophorone diisocyanate, hydrogenated xylylene diisocyanate, and hydrogenated diphenylmethane diisocyanate; aromatic diisocyanate compounds, such as tolylene diisocyanate, xylylene diisocyanate, tetramethylxylylene diisocyanate, diphenylmethane diisocyanate, and 1,5-naphthalene diisocyanate; polymethylene polyphenyl polyisocyanate having repeating structures represented by structural formula (8) below; and isocyanurates, biurets, and allophanates of the foregoing compounds.

[Chem. 17]

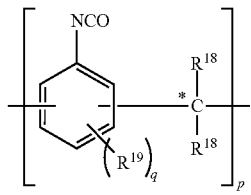

(8)

Here, $R^{18}$'s are each independently one of a hydrogen atom and a hydrocarbon group having 1 to 6 carbon atoms. $R^9$'s are each independently an alkyl group having 1 to 4 carbon atoms or a point of attachment connected to a structural moiety represented by structural formula (8) via the methylene group indicated by symbol *. q is an integer of 0 or 1 to 3, and p is an integer greater than or equal to 1.

Examples of the hydroxy-group-containing (meth)acrylate compounds include hydroxy-group-containing (meth)acrylate compounds such as hydroxyethyl (meth)acrylate, hydroxypropyl (meth)acrylate, trimethylolpropane di(meth)acrylate, pentaerythritol tri(meth)acrylate, ditrimethylolpropane tri(meth)acrylate, and dipentaerythritol penta(meth)acrylate. Further examples include (poly)oxyalkylene-modified products of the above-mentioned various hydroxy-group-containing (meth)acrylate compounds, the products having a (poly)oxyalkylene chain, such as a (poly)oxyethylene chain, a (poly)oxypropylene chain, or a (poly)oxytetramethylene chain, introduced in the molecular structure; and lactone-modified products of the above-mentioned various hydroxy-group-containing (meth)acrylate compounds, the products having a (poly)lactone structure introduced in the molecular structure.

Examples of the polyol compounds include aliphatic polyol compounds, such as ethylene glycol, propylene glycol, butanediol, hexanediol, glycerol, trimethylolpropane, ditrimethylolpropane, pentaerythritol, and dipentaerythritol; and aromatic polyol compounds, such as biphenols and bisphenols. Further examples include (poly)oxyalkylene-modified products of the above-mentioned various polyol compounds, the products having a (poly)oxyalkylene chain, such as a (poly)oxyethylene chain, a (poly)oxypropylene chain, or a (poly)oxytetramethylene chain, introduced in the molecular structure; and lactone-modified products of the above-mentioned various polyol compounds, the products having a (poly)lactone structure introduced in the molecular structure.

Examples of the acrylic (meth)acrylate resins and modified products thereof (R8) include products obtained in the following manner. An acrylic resin intermediate is obtained by performing polymerization in which a reactive-functional-group-containing (meth)acrylate monomer (α) is used as an essential component, examples of the reactive functional group including hydroxy groups, carboxy groups, isocyanate groups, and glycidyl groups. Furthermore, the acrylic resin intermediate is reacted with a reactive-functional-group-containing (meth)acrylate monomer (β), the reactive functional group being capable of reacting with the above-mentioned functional groups. Accordingly, (meth)acryloyl groups are introduced.

Examples of the reactive-functional-group-containing (meth)acrylate monomer (α) include hydroxy-group-containing (meth)acrylate monomers, such as hydroxyethyl (meth)acrylate and hydroxypropyl (meth)acrylate; carboxy-group-containing (meth)acrylate monomers, such as (meth)acrylic acid; isocyanate-group-containing (meth)acrylate monomers, such as 2-acryloyloxyethyl isocyanate, 2-methacryloyloxyethyl isocyanate, and 1,1-bis(acryloyloxymethyl) ethyl isocyanate, and glycidyl-group-containing (meth)acrylate monomers, such as glycidyl (meth)acrylate and 4-hydroxybutyl acrylate glycidyl ether. These may be used alone or in a combination of two or more.

The acrylic resin intermediate may be an intermediate in which the (meth)acrylate monomer (α) is copolymerized, if necessary, with one or more additional polymerizable-unsaturated-group-containing compounds. Examples of the one or more additional polymerizable-unsaturated-group-containing compounds include (meth)acrylic acid alkyl esters, such as methyl (meth)acrylate, ethyl (meth)acrylate, propyl (meth)acrylate, butyl (meth)acrylate, and 2-ethylhexyl (meth)acrylate; cyclo-ring-containing (meth)acrylates, such as cyclohexyl (meth)acrylate, isobornyl (meth)acrylate, and dicyclopentanyl (meth)acrylate; aromatic-ring-containing (meth)acrylates, such as phenyl (meth)acrylate, benzyl (meth)acrylate, and phenoxyethyl acrylate; silyl-group-containing (meth)acrylates, such as 3-methacryloxy-propyl trimethoxysilane; and styrene and styrene derivatives, such as α-methylstyrene and chlorostyrene. These may be used alone or in a combination of two or more.

The (meth)acrylate monomer (β) is not particularly limited provided that the (meth)acrylate monomer (β) is capable of reacting with a reactive functional group present in the (meth)acrylate monomer (α); however, the following combinations are preferable from the standpoint of reactivity. Specifically, in a case where a hydroxy-group-containing (meth)acrylate is used as the (meth)acrylate monomer (α), it is preferable to use, as the (meth)acrylate monomer (β), an isocyanate-group-containing (meth)acrylate. In a case where a carboxy-group-containing (meth)acrylate is used as the (meth)acrylate monomer (α), it is preferable to use, as the (meth)acrylate monomer (β), a glycidyl-group-containing (meth)acrylate. In a case where an isocyanate-group-containing (meth)acrylate is used as the (meth)acrylate monomer (α), it is preferable to use, as the (meth)acrylate monomer (β), a hydroxy-group-containing (meth)acrylate. In a case where a glycidyl-group-containing (meth)acrylate is used as the (meth)acrylate monomer (α), it is preferable to use, as the (meth)acrylate monomer (β), a carboxy-group-containing (meth)acrylate.

It is preferable that the acrylic (meth)acrylate resins and modified products thereof (R8) have a weight average molecular weight (Mw) within a range of 5,000 to 50,000. Furthermore, it is preferable that the (meth)acryloyl group equivalent weight be within a range of 200 to 300 g/eq.

The dendrimer-type (meth)acrylate resins and modified products thereof (R9) are resins having an ordered multi-branched structure and having a (meth)acryloyl group at an end of each of the branched chains. Such resins are referred to as dendrimer type and are also referred to as hyper-branched type, star polymers, and the like. Examples of such compounds include compounds represented by formulae (9-1) to (9-8) below. These are non-limiting examples, and any compound may be used provided that the compound is a resin having an ordered multi-branched structure and having a (meth)acryloyl group at an end of each of the branched chains.

[Chem. 18]

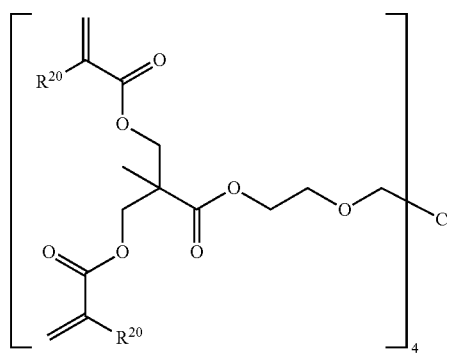

(9-1)

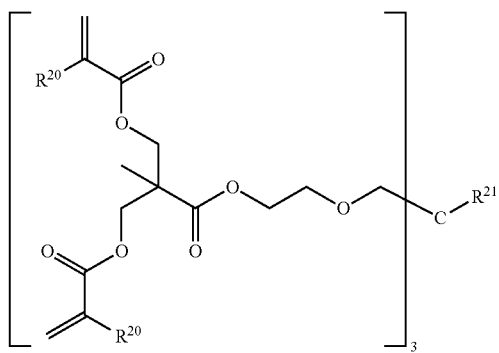

(9-2)

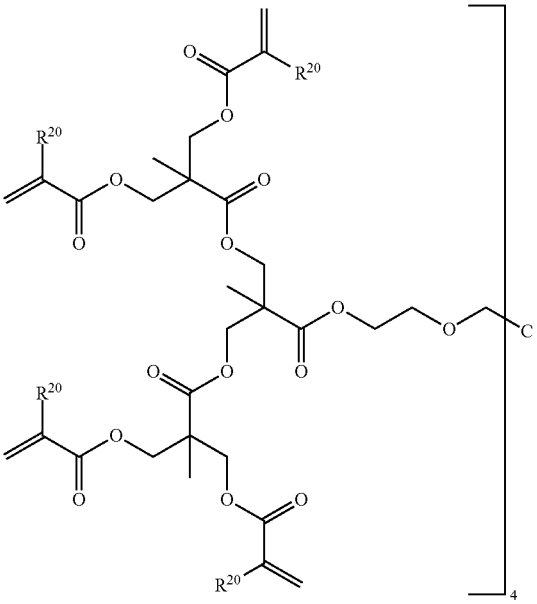

(9-3)

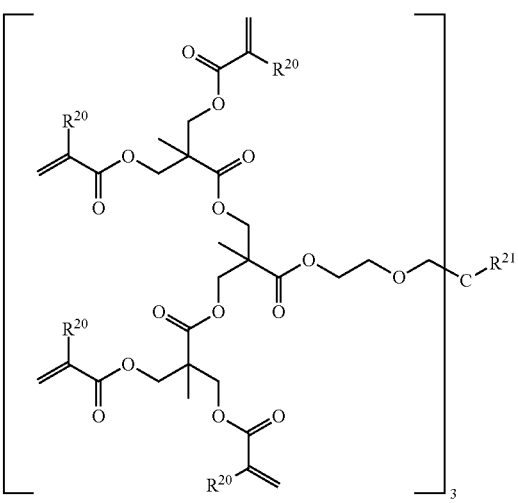

(9-4)

[Chem. 19]

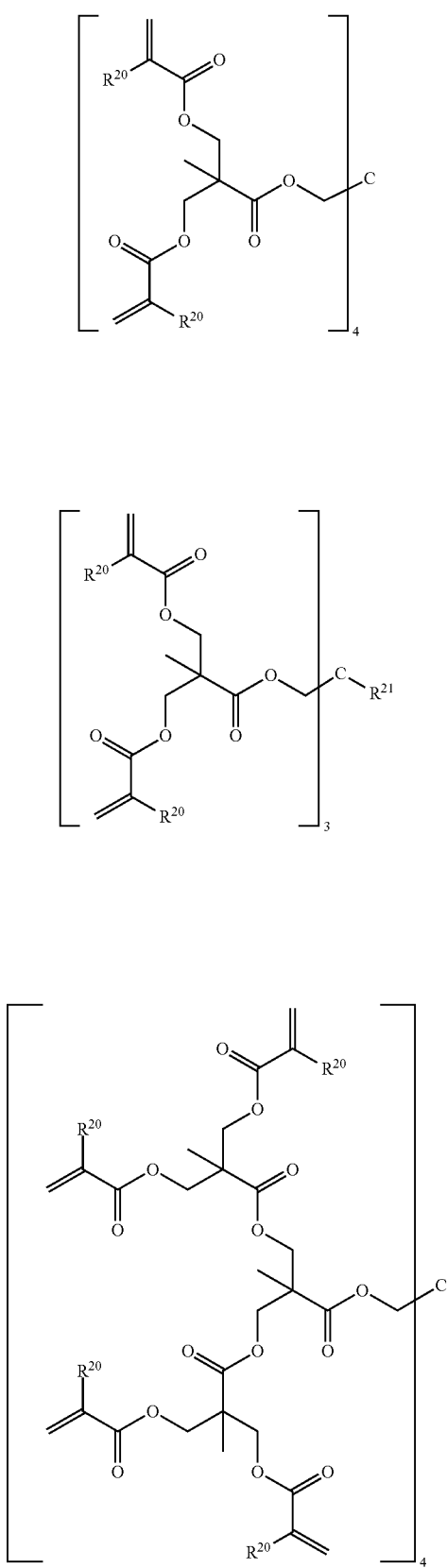

(9-5)

(9-6)

(9-7)

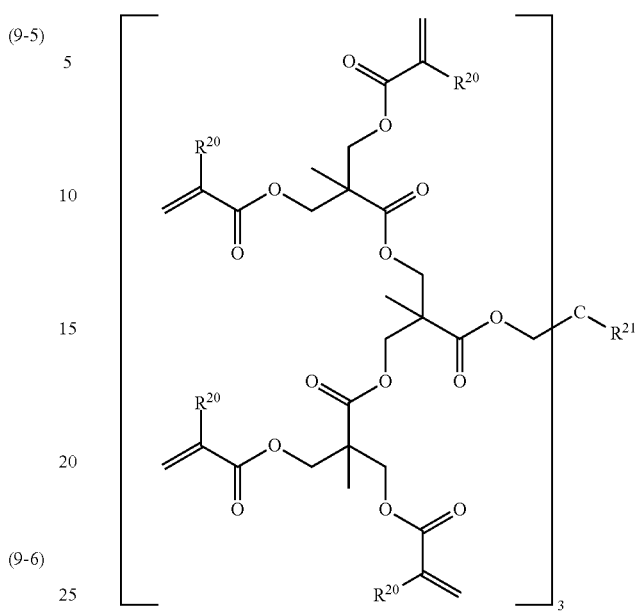

(9-8)

Here, R$^{20}$'s are a hydrogen atom or a methyl group, and R$^{21}$ is a hydrocarbon group having 1 to 4 carbon atoms.

Such dendrimer-type (meth)acrylate resins and modified products thereof (R9) may be commercially available products, examples of which include Viscoat #1000 [weight average molecular weight (Mw), 1,500 to 2,000; average (meth)acryloyl group number on per-molecule basis, 14], Viscoat 1020 [weight average molecular weight (Mw), 1,000 to 3,000], and SIRIUS 501 [weight average molecular weight (Mw), 15,000 to 23,000], manufactured by Osaka Organic Chemical Industry Ltd.; SP-1106 [weight average molecular weight (Mw), 1,630; average (meth)acryloyl group number on per-molecule basis, 18], manufactured by Miwon Specialty Chemical Co., Ltd.; CN2301 and CN2302 [average (meth)acryloyl group number on per-molecule basis, 16], CN2303 [average (meth)acryloyl group number on per-molecule basis, 6], and CN2304 [average (meth) acryloyl group number on per-molecule basis, 18], manufactured by Sartomer Company; Esdrimer HU-22, manufactured by Nippon Steel & Sumikin Chemical Co., Ltd.; A-HBR-5, manufactured by Shin Nakamura Chemical Co., Ltd.; New Frontier R-1150, manufactured by DKS Co., Ltd.; and Hypertech UR-101, manufactured by Nissan Chemical Corporation.

It is preferable that the dendrimer-type (meth)acrylate resins and modified products thereof (R9) have a weight average molecular weight (Mw) within a range of 1,000 to 30,000. Furthermore, it is preferable that the average (meth) acryloyl group number on a per-molecule basis be within a range of 5 to 30.

In the case where a calixarene compound of the present invention is used as a photocurable resin material, it is preferable that the material include a photopolymerization initiator. The photopolymerization initiator may be appropriately selected in accordance with, for example, the type of actinic radiation to be radiated. Specific examples of the photopolymerization initiator include alkylphenone-based photopolymerization initiators, such as 1-hydroxy cyclohexyl phenyl ketone, 2-benzyl-2-dimethylamino-1-(4-morpholinophenyl)-butanone-1, and 2-(dimethylamino)-2-[(4- methylphenyl)methyl]-1-[4-(4-morpholinyl)phenyl]-1-butanone; acylphosphine oxide-based photopolymerization initiators, such as 2,4,6-trimethylbenzoyl diphenyl phosphine oxide; and intramolecular-hydrogen-abstraction-type photopolymerization initiators, such as benzophenone compounds. These may be used alone or in a combination of two or more.

Examples of commercially available products of the photopolymerization initiator include Irgacure 127, Irgacure 184, Irgacure 250, Irgacure 270, Irgacure 290, Irgacure 369E, Irgacure 379EG, Irgacure 500, Irgacure 651, Irgacure 754, Irgacure 819, Irgacure 907, Irgacure 1173, Irgacure 2959, Irgacure MBF, Irgacure TPO, Irgacure OXE 01, and Irgacure OXE 02, manufactured by BASF.

It is preferable that the amount of the photopolymerization initiator to be used be within a range of 0.05 to 20 parts by mass per 100 parts by mass of the components other than an organic solvent of the curable composition; more preferably, the range is 0.1 to 10 parts by mass.

The curable composition may be diluted with an organic solvent. Examples of the organic solvent include alkylene glycol monoalkyl ethers, such as ethylene glycol monomethyl ether, ethylene glycol monoethyl ether, ethylene glycol monopropyl ether, ethylene glycol monobutyl ether, and propylene glycol monomethyl ether; dialkylene glycol dialkyl ethers, such as diethylene glycol dimethyl ether, diethylene glycol diethyl ether, diethylene glycol dipropyl ether, and diethylene glycol dibutyl ether; alkylene glycol alkyl ether acetates, such as ethylene glycol monomethyl ether acetate, ethylene glycol monoethyl ether acetate, and propylene glycol monomethyl ether acetate; ketone compounds, such as acetone, methyl ethyl ketone, cyclohexanone, and methyl amyl ketone; cyclic ethers, such as dioxane; and ester compounds, such as methyl 2-hydroxypropanoate, ethyl 2-hydroxypropanoate, ethyl 2-hydroxy-2-methylpropanoate, ethyl ethoxyacetate, ethyl oxyacetate, 2-hydroxy-3-methylbutanoic acid methyl ester, 3-methoxybutyl acetate, 3-methyl-3-methoxybutyl acetate, ethyl formate, ethyl acetate, butyl acetate, methyl acetoacetate, and ethyl acetoacetate. These may be used alone or in a combination of two or more. The amount of the organic solvent to be added is appropriately adjusted in accordance with, for example, a desired viscosity of the composition.

A curable composition of the present invention may include any of a variety of additives in accordance with desired properties. Examples of the additives include UV absorbers, antioxidants, photosensitizers, silicone-based additives, silane coupling agents, fluorinated additives, rheology control agents, defoaming agents, antistatic agents, antifogging agents, adhesion agents, organic pigments, inorganic pigments, extender pigments, organic fillers, and inorganic fillers.

EXAMPLES

The present invention will now be described in more detail with reference to Production Examples and Examples; however, the present invention is not limited to these examples. In the examples, "parts" and "%" are all on a mass basis unless otherwise specified.

The structures of the products (calixarene compounds) were determined by using $^1$H-NMR, $^{13}$C-NMR, and FD-MS measured under the following conditions.

The $^1$H-NMR was measured under the following conditions by using a JNM-ECM400S, manufactured by Jeol Resonance Inc.

Magnetic field strength: 400 MHz
Number of scans: 16
Solvent: deuterated chloroform
Sample concentration: 2 mg/0.5 ml The $^{13}$C-NMR was measured under the following conditions by using a JNM-ECM400S, manufactured by Jeol Resonance Inc.

Magnetic field strength: 100 MHz
Number of scans: 1000
Solvent: deuterated chloroform
Sample concentration: 2 mg/0.5 ml The FD-MS was measured under the following conditions by using a JMS-T100GC AccuTOF, manufactured by JEOL Ltd.

Measurement range: m/z=50.00 to 2000.00
Rate of change: 25.6 mA/min
Final current value: 40 mA
Cathode voltage: −10 kV Synthesis Example 1: Synthesis of Intermediate (α-1)

In a 20-L separable four-neck flask equipped with a stirrer, a thermometer, and a reflux condenser, 1000 g (1.54 mol) of tert-butyl calix[4]arene, 1159 g (12.32 mol) of phenol, and 9375 ml of anhydrous toluene were quickly loaded and stirred at 300 rpm under a nitrogen flow. The tert-butyl calix[4]arene, which was a starting material, was not dissolved but suspended. Subsequently, 1643 g (12.32 mol) of anhydrous aluminum (III) chloride was added in several portions while the flask was cooled in an ice bath. The solution turned to a clear pale orange solution, with anhydrous aluminum (III) chloride being sedimented on the bottom. The reaction was allowed to proceed at room temperature for 5 hours. Subsequently, the contents were transferred to a 1-L beaker, and 20 kg of ice, 10 L of 1N hydrochloric acid, and 20 L of chloroform were added to quench the reaction. The solution turned clear pale yellow. The reaction mixture was transferred to a separatory funnel to separate the organic layer. Next, the aqueous layer was extracted three times with 5 L of chloroform, and the organic layers were combined together. The organic layers were predried with anhydrous magnesium sulfate and then filtered. The solvent was evaporated using an evaporator, and thus a mixture of white crystals and a clear colorless liquid was obtained. Methanol was slowly added to the mixture with stirring, to cause reprecipitation. White crystals were filtered out with a Kiriyama funnel and then washed with methanol. White crystals that were obtained were dried under vacuum (at 50° C. for 6 hours or more). Thus, an intermediate (α-1), which was a target compound, was obtained. The intermediate (α-1) was in an amount of 597 g. The yield was 91%.

[Chem. 20]

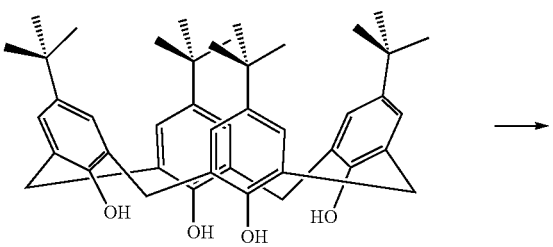

(α-1)

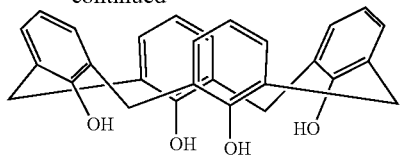

Synthesis Example 2: Introduction of R4's (d1) (1)

In a 2-L four-neck flask equipped with a stirrer, a thermometer, and a reflux condenser, 205 g (1.52 mol) of n-hexanoyl chloride and 709 g (9.44 mol) of nitroethane were added and stirred. Subsequently, 243 g (1.82 mol) of anhydrous aluminum (III) chloride was added in several portions while the flask was cooled in an ice bath. The solution turned to a clear pale orange solution. While stirring was performed at room temperature for 30 minutes, 100 g (0.236 mol) of the intermediate (α-1) was added in several portions. The reaction proceeded with foaming, and the solution turned to a clear orange solution. The reaction was allowed to proceed at room temperature for 5 hours. Subsequently, the contents were slowly transferred to a 2-L beaker containing 450 ml of chloroform and 956 g of ice water to terminate the reaction. Subsequently, 1N hydrochloric acid was added until a pH of 1 was reached. Subsequently, the reaction mixture was transferred to a separatory funnel to separate the organic layer. Next, the aqueous layer was extracted three times with 400 ml of chloroform, and the organic layers were combined together. The organic layers were predried with anhydrous magnesium sulfate and then filtered. The solvent was evaporated using an evaporator, and thus a clear yellow solution was obtained. In an ice bath, methanol was added to cause reprecipitation. White crystals were filtered out with a Kiriyama funnel and then recrystallized in chloroform and methanol. White crystals that were obtained were dried under vacuum (at 60° C. for 6 hours or more). Thus, a compound represented by the structural formula below was obtained. The compound was in an amount of 122 g. The yield was 63%.

[Chem. 21]

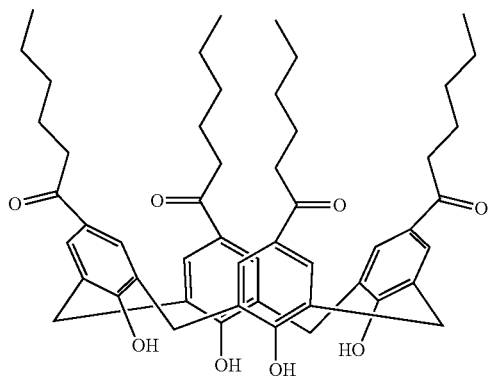

Synthesis Example 3: Introduction of R$^4$'s (d1) (2)

This example was carried out as in Synthesis Example 2 except that butyl chloride was used instead of n-hexanoyl chloride. Thus, a compound represented by the structural formula below was obtained. The compound was in an amount of 106 g. The yield was 64%.

[Chem. 22]

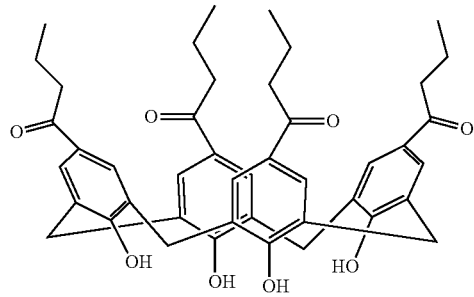

Synthesis Example 4: Introduction of R$^4$'s (d1) (3)

This example was carried out as in Synthesis Example 2 except that n-heptanoyl chloride was used instead of n-hexanoyl chloride. Thus, a compound represented by the structural formula below was obtained. The compound was in an amount of 134 g. The yield was 65%.

[Chem. 23]

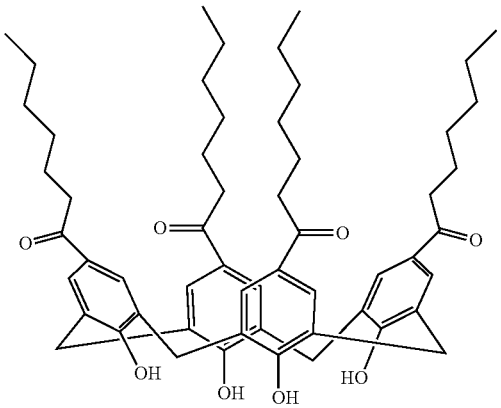

Synthesis Example 5: Introduction of R$^4$'s (d1) (4)

This example was carried out as in Synthesis Example 2 except that stearoyl chloride was used instead of n-hexanoyl chloride. Thus, a compound represented by the structural formula below was obtained. The compound was in an amount of 228 g. The yield was 65%.

[Chem. 24]

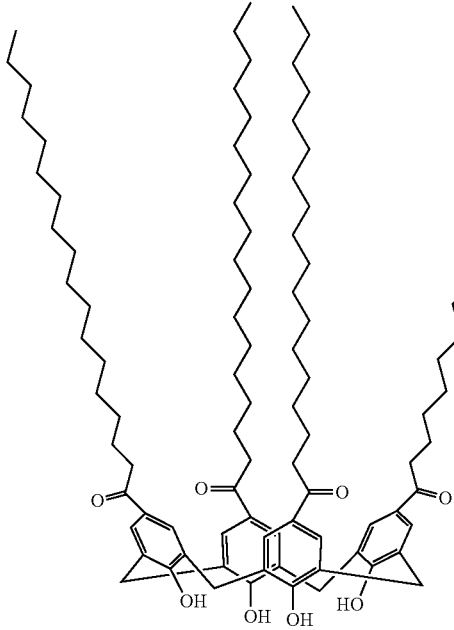

[Chem. 25]

(1-1)

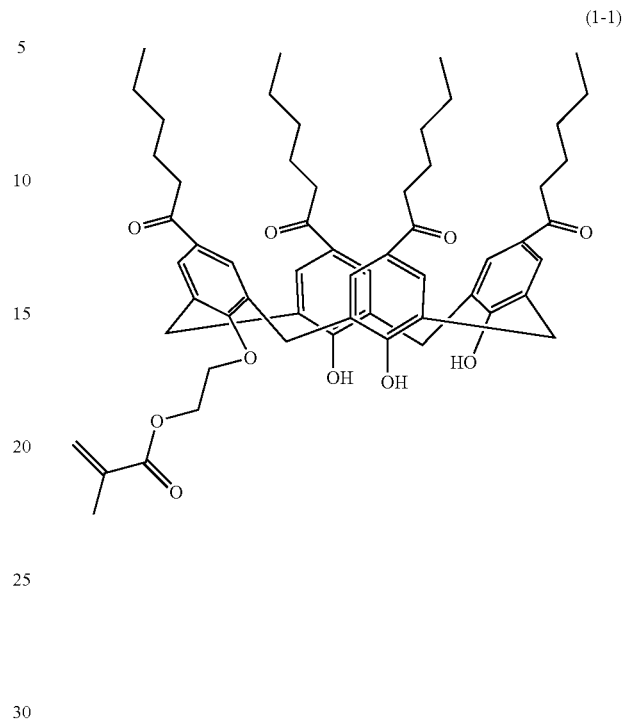

(1-2)

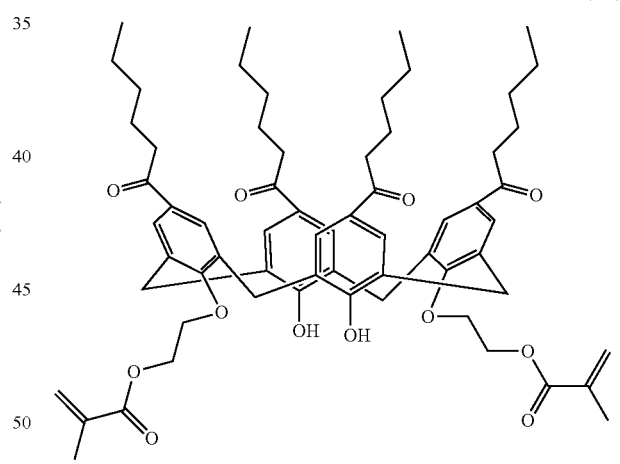

Example 2

Example 1: Introduction of R⁵'s (B)

In a 50-mL four-neck flask equipped with a stirrer, a thermometer, and a reflux condenser, 1.00 g (1.224 mmol) of the compound obtained in Synthesis Example 2, 8.8 g of tetrahydrofuran, 1.059 g (4.039 mmol) of triphenylphosphine, and 0.478 g (3.672 mmol) of hydroxyethyl methacrylate were added and stirred. The resulting solution, which was a suspended ocherous solution, was cooled in ice, and thereafter 0.907 g (4.039 mmol) of diisopropyl azodicarboxylate was added dropwise over 30 minutes. The reaction liquid turned to a clear orange solution and was stirred as it was at room temperature for 6 hours. Hexane was added to the reaction solution to remove by-products, such as triphenylphosphine, by precipitation, and thereafter chloroform extraction was carried out. The extracts were washed with water and saturated brine and subsequently dried with magnesium sulfate. The solvent was evaporated using an evaporator. A red viscous liquid was purified by column chromatography (developing solvent:n-hexane:acetone=95:5) Thus, a compound (1-1) and a compound (1-2), which were target compounds, were obtained. The compound (1-1) was in an amount of 0.2309 g, in a 20.3% yield. The compound (1-2) was in an amount of 0.4524 g, in a 35.5% yield. The compound (1-1) contained, as R⁵, one structural moiety (B). The compound (1-2) contained, as R⁵'s, two structural moieties (B).

This example was carried out as in Example 1 except that the compound obtained in Synthesis Example 3 was used instead of the compound obtained in Synthesis Example 2, which was used in Example 1. Thus, a compound (2-1) and a compound (2-2), which were target compounds, were obtained. The compound (2-1) was in an amount of 0.1808 g, in a 15.6% yield. The compound (2-2) was in an amount of 0.4653 g, in a 35.3% yield. The compound (2-1) contained, as R⁵, one structural moiety (B). The compound (2-2) contained, as R⁵'s, two structural moieties (B).

[Chem. 26]

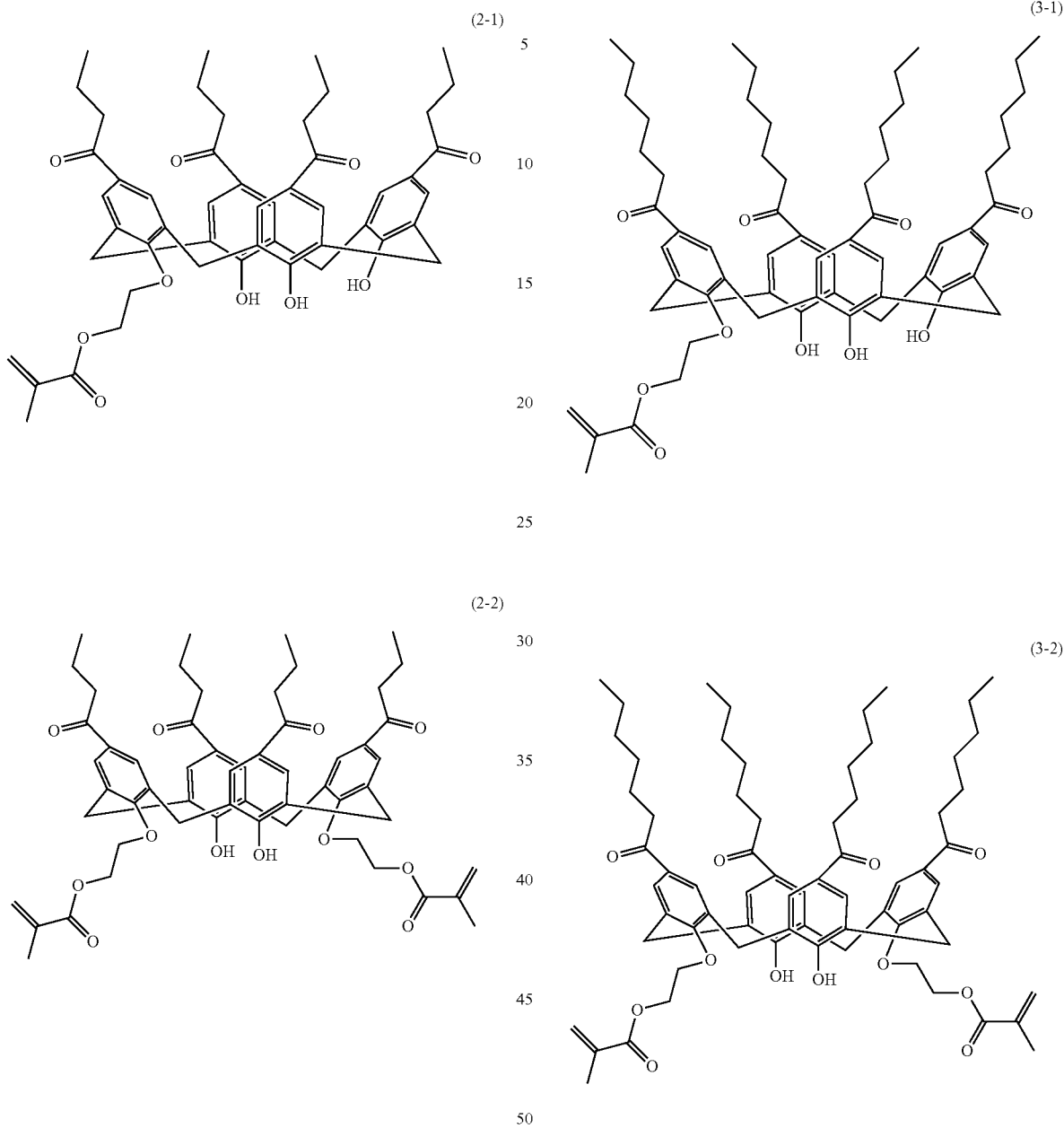

Example 3

This example was carried out as in Example 1 except that the compound obtained in Synthesis Example 4 was used instead of the compound obtained in Synthesis Example 2, which was used in Example 1. Thus, a compound (3-1) and a compound (3-2), which were target compounds, were obtained. The compound (3-1) was in an amount of 0.2313 g, in a 20.5% yield. The compound (3-2) was in an amount of 0.4072 g, in a 32.4% yield. The compound (3-1) contained, as $R^5$, one structural moiety (B). The compound (3-2) contained, as $R^5$'s, two structural moieties (B).

Example 4

This example was carried out as in Example 1 except that hydroxyethyl acrylate was used instead of hydroxyethyl methacrylate. Thus, a compound (4-1) and a compound (4-2), which were target compounds, were obtained. The compound (4-1) was in an amount of 0.2890 g, in a 25.8% yield. The compound (4-2) was in an amount of 0.4688 g, in a 37.8% yield. The compound (4-1) contained, as $R^5$, one structural moiety (B). The compound (4-2) contained, as $R^5$'s, two structural moieties (B).

[Chem. 28]

(4-1)

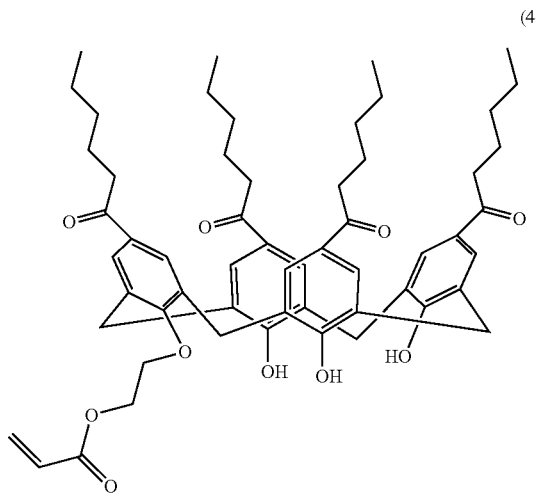

(4-2)

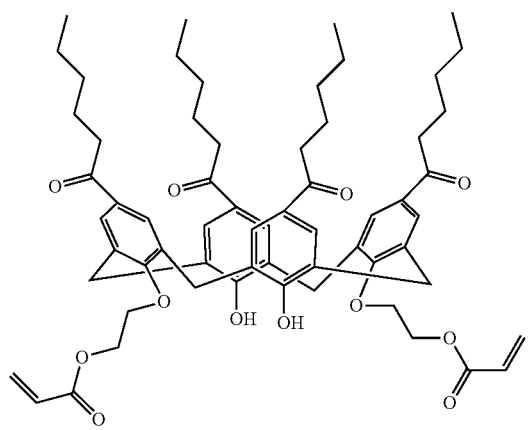

[Chem. 29]

(5-1)

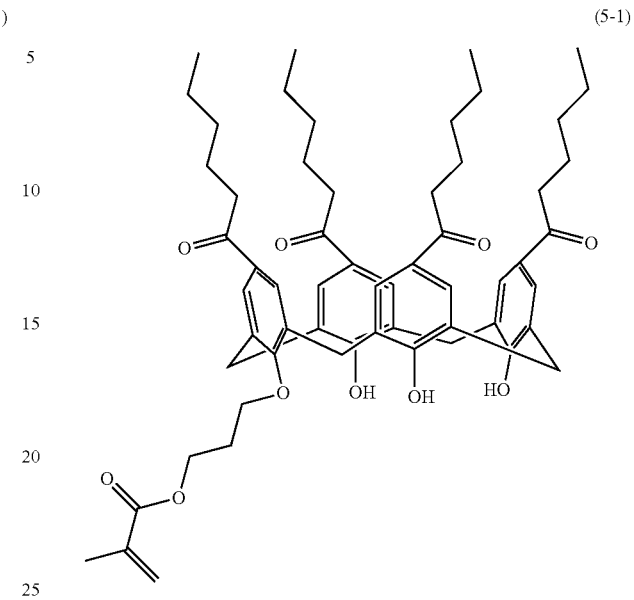

(5-2)

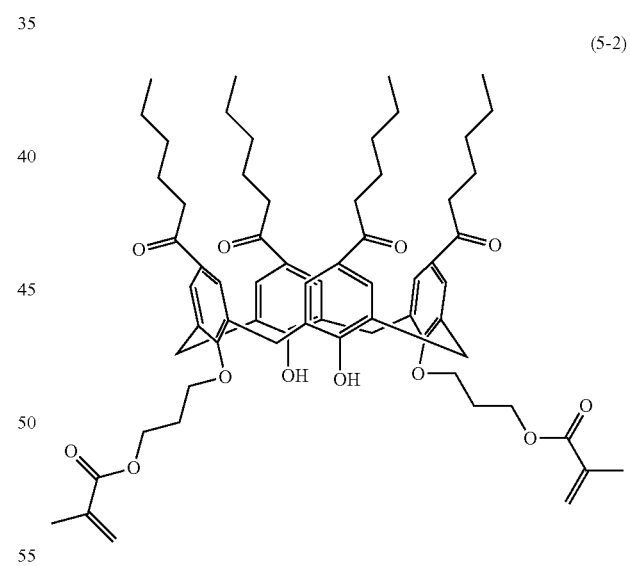

Example 5

This example was carried out as in Example 1 except that hydroxypropyl methacrylate was used instead of hydroxy methacrylate. Thus, a compound (5-1) and a compound (5-2), which were target compounds, were obtained. The compound (5-1) was in an amount of 0.257 g, in a 22.3% yield. The compound (5-2) was in an amount of 0.439 g, in a 33.6% yield. The compound (5-1) contained, as $R^5$, one structural moiety (B). The compound (5-2) contained, as $R^5$'s, two structural moieties (B).

Example 6

This example was carried out as in Example 1 except that 4-hydroxybutyl acrylate was used instead of hydroxy methacrylate. Thus, a compound (6-1) and a compound (6-2), which were target compounds, were obtained. The compound (6-1) was in an amount of 0.353 g, in a 30.6% yield. The compound (6-2) was in an amount of 0.543 g, in a 41.5% yield. The compound (6-1) contained, as $R^5$, one structural moiety (B). The compound (6-2) contained, as $R^5$'s, two structural moieties (B).

[Chem. 30]

(6-1)

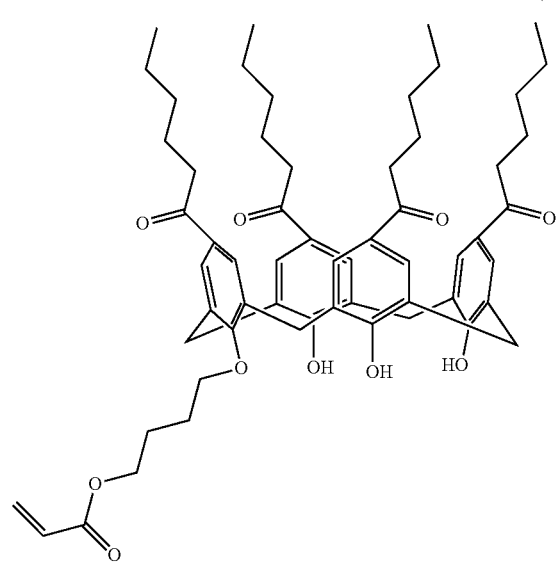

(6-2)

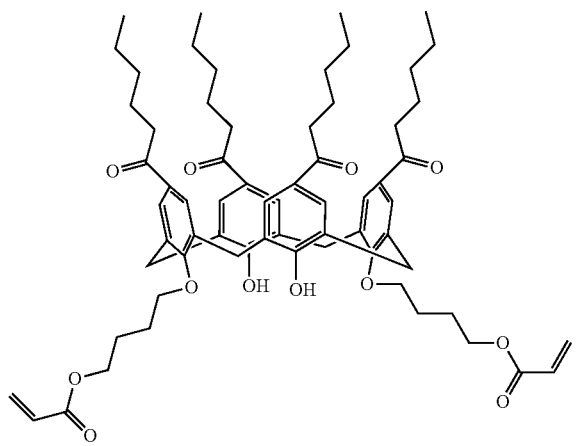

Synthesis Example 6: Modification of Phenolic Hydroxy Groups (Synthesis of Precursor)

In a 100-mL four-neck flask equipped with a stirrer, a thermometer, and a reflux condenser, 5.00 g (6.119 mmol) of the compound obtained in Synthesis Example 2, 24.10 g of anhydrous acetone, 11.28 g (48.95 mmol) of potassium carbonate, 0.813 g (4.896 mmol) of potassium iodide, and 7.489 g (48.95 mmol) of methyl 2-bromoacetate were added and heated at 60° C. for 40 hours. The contents were cooled to room temperature. Subsequently, ion exchanged water and 0.3N hydrochloric acid were added to bring the pH to 6. The reaction mixture was transferred to a separatory funnel and then extracted with 50 g of chloroform that was added. Next, the aqueous layer was extracted three times with 50 g of chloroform, and the organic layers were combined together. The organic layers were predried with anhydrous magnesium sulfate and then filtered. The solvent was evaporated using an evaporator. A red waxy solid that was obtained was dried under vacuum (at 60° C. for 6 hours or more). Thus, a compound represented below, which was a target compound, was obtained. The compound was in an amount of 5.039 g. The yield was 74.5%.

[Chem. 31]

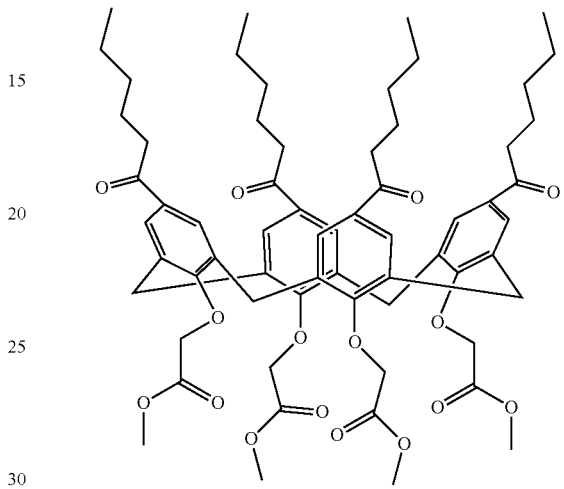

Synthesis Example 7

In a 500-mL four-neck flask equipped with a stirrer, a thermometer, and a reflux condenser, in an ice bath, 16.44 g of anhydrous tetrahydrofuran was added, and 1.038 g (27.35 mmol) of lithium aluminum hydride was slowly added. The 5.039 g (4.559 mmol) compound obtained in Synthesis Example 6 was diluted with 49.31 g (683.8 mmol) of anhydrous tetrahydrofuran and added using a dropping funnel, in a manner such that the temperature did not exceed 10° C. The resulting reaction solution, which was a gray suspension, was stirred at room temperature for 6 hours to cause a reaction. In an ice bath, 30 g of chloroform was added, and 30 g of 5N hydrochloric acid was added drop by drop to terminate the reaction. Subsequently, the reaction liquid was filtered through diatomaceous earth. The filtrate was transferred to a separatory funnel to separate the organic layer. Next, the aqueous layer was extracted three times with 30 g of chloroform, and the organic layers were combined together. The organic layers were predried with anhydrous magnesium sulfate and then filtered. The solvent was evaporated using an evaporator. A pale yellow liquid that was obtained was subjected to column chromatography (developing solvents:n-hexane:ethyl acetate=1:1, which was used to remove by-products, and chloroform:isopropyl alcohol=5:1, which was subsequently used). Thus, a white solid was obtained. The white solid that was obtained was dried under vacuum (at 60° C. for 6 hours or more). Thus, a compound represented below, which was a target compound, was obtained. The compound was in an amount of 2.857 g. The yield was 63.1%.

[Chem. 32]

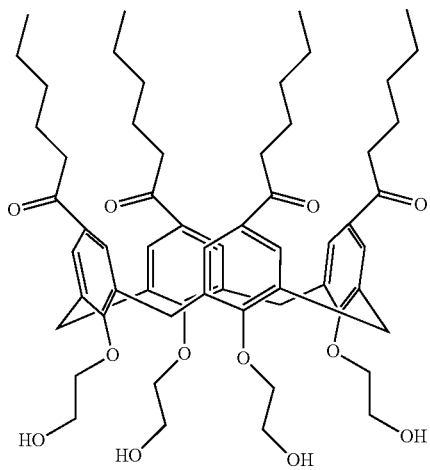

[Chem. 33]

(7-1)

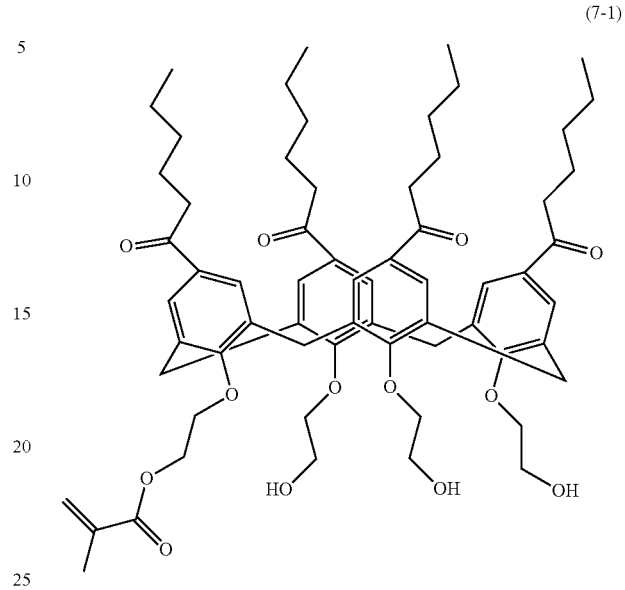

Example 7

In a 100-mL four-neck flask equipped with a stirrer, a thermometer, and a reflux condenser, 2.00 g (2.014 mmol) of the compound obtained in Synthesis Example 7, 7.26 g of tetrahydrofuran, 1.056 g (4.027 mmol) of triphenylphosphine, and 0.347 g (4.027 mmol) of methacrylic acid were added and stirred. A clear pale yellow solution. Next, in an ice bath, 0.905 g (4.027 mmol) of diisopropyl azodicarboxylate was added dropwise over 30 minutes. A clear pale yellow solution. Stirring was performed at room temperature for 10 hours. Hexane was added to the reaction solution to remove by-products, such as triphenylphosphine, by precipitation, and thereafter chloroform extraction was carried out. The extracts were washed with water and saturated brine and subsequently dried with magnesium sulfate. The solvent was evaporated using an evaporator. An orange viscous liquid was purified by column chromatography (developing solvent: n-hexane:acetone=90:10). Thus, a compound (7-1), two compounds (7-2) and (7-3), and a compound (7-4), which are represented by the structural formulae below, were obtained. The compound (7-1) contained, as $R^5$'s, three structural moieties (A) and one structural moiety (B). The compounds (7-2) and (7-3) each contained two structural moieties (A) and two structural moieties (B). The compound (7-4) contained one structural moiety (A) and three structural moieties (B). The compounds were dried under vacuum (at 60° C. for 6 hours or more). The compounds were in respective amounts of 0.765 g, 0.321 g, 0.287 g, and 0.101 g, with the respective yields being 35.8%, 14.1%, 12.6%, and 4.2%.

(7-2)

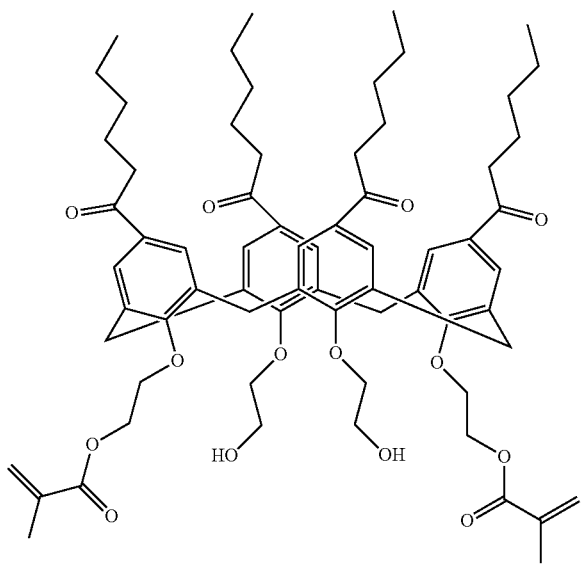

(7-3)
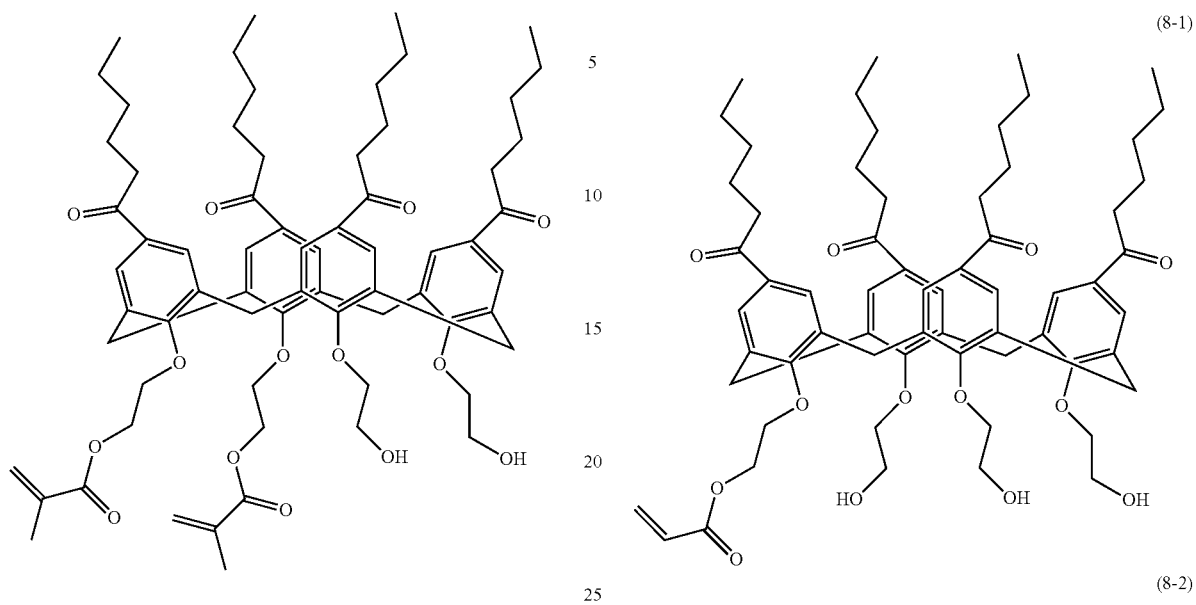
(7-4)
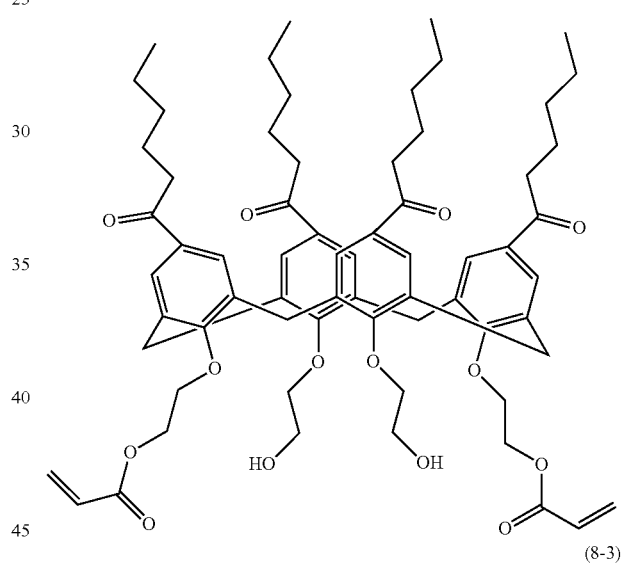
Example 8
This example was carried out as in Example 7 except that acrylic acid was used instead of methacrylic acid. The compounds were in respective amounts of 0.843 g, 0.475 g, 0.342 g, and 0.124 g, with the respective yields being 40.0%, 21.4%, 15.4%, and 5.33%.
[Chem. 34]
(8-1)
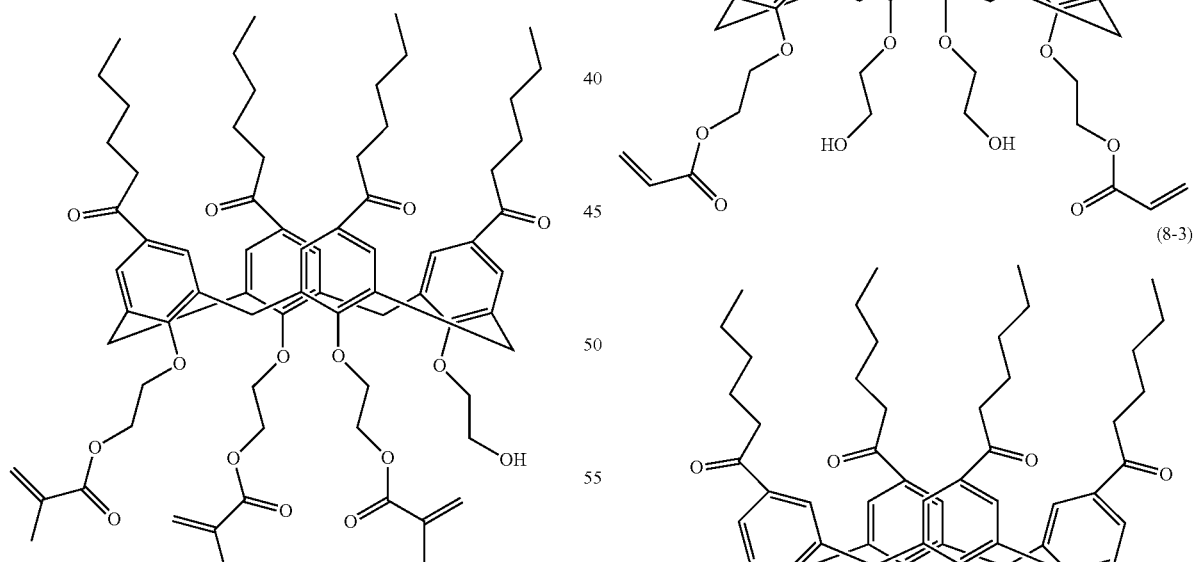
(8-2)
(8-3)
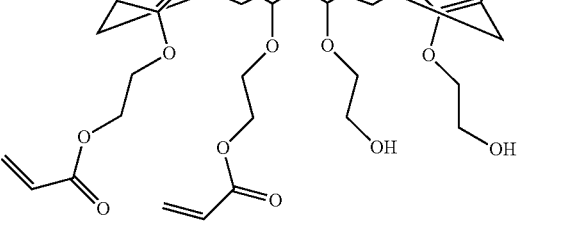

(8-4)

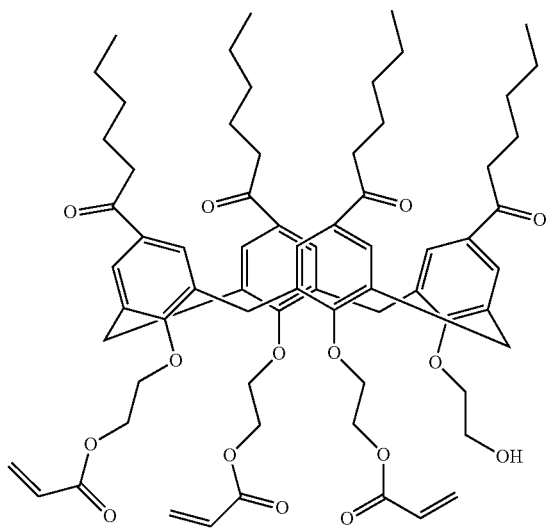

[Chem. 36]

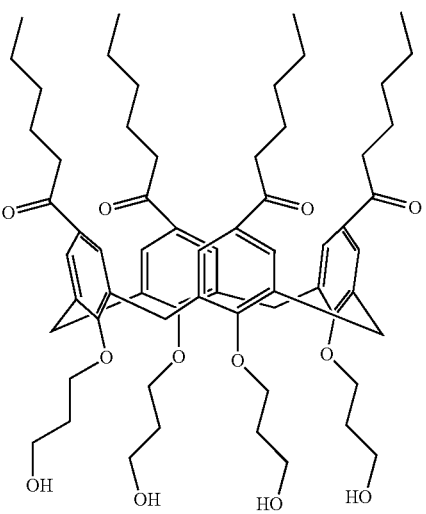

Synthesis Example 8

This example was carried out as in Synthesis Example 6 except that methyl bromopropionate was used instead of methyl bromoacetate. Thus, a compound represented below, which was a target compound, was obtained. The compound was in an amount of 4.307 g. The yield was 60.6%.

[Chem. 35]

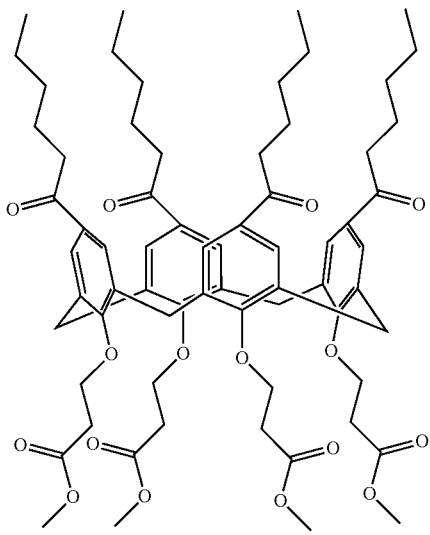

Synthesis Example 9

This example was carried out as in Synthesis Example 7 except that the compound obtained in Synthesis Example 8 was used instead of the compound obtained in Synthesis Example 6. Thus, a compound represented below, which was a target compound, was obtained. The compound was in an amount of 2.989 g. The yield was 80.6%.

Example 9

This example was carried out as in Example 7 except that the compound obtained in Synthesis Example 9 was used instead of the compound obtained in Synthesis Example 7. Thus, compounds shown below were obtained. The compounds were in respective amounts of 0.783 g (36.8% yield), 0.374 g (16.6% yield), 0.374 g (16.6% yield), and 0.123 g (5.15% yield).

[Chem. 37]

(9-1)

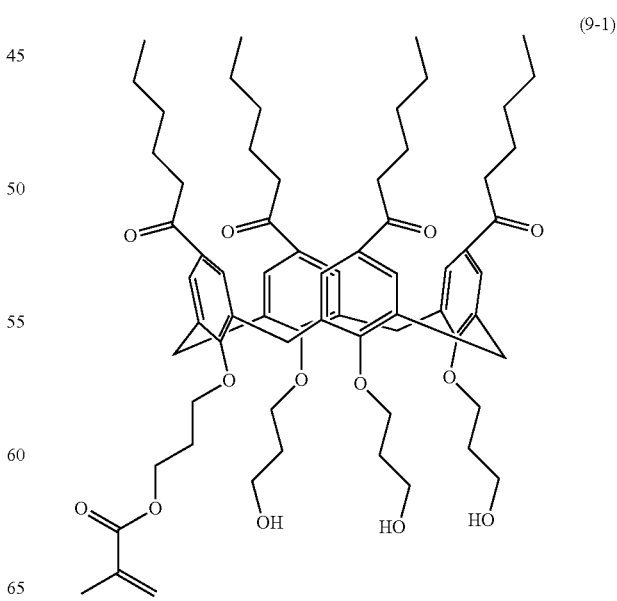

(9-2)
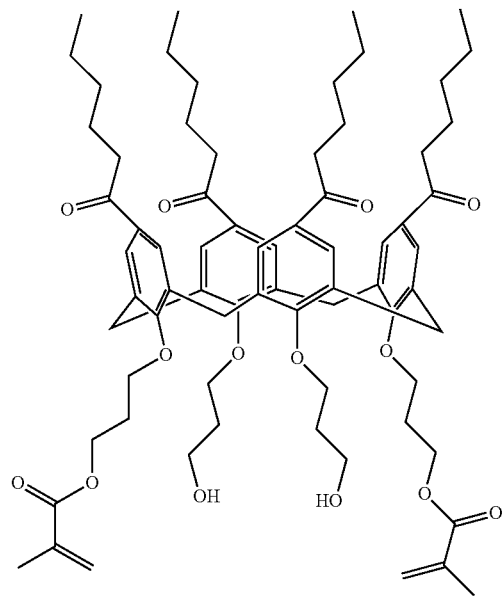
(9-4)
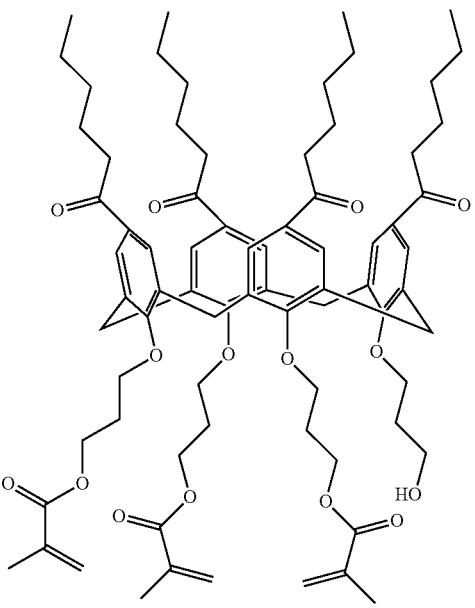
Example 10
This example was carried out as in Example 9 except that acrylic acid was used instead of methacrylic acid. Thus, compounds shown below were obtained. The compounds were in respective amounts of 0.329 g (15.6% yield), 0.189 g (8.57%), 0.173 g (7.84% yield), and 0.089 g (3.85% yield).
[Chem. 38]
(9-3)
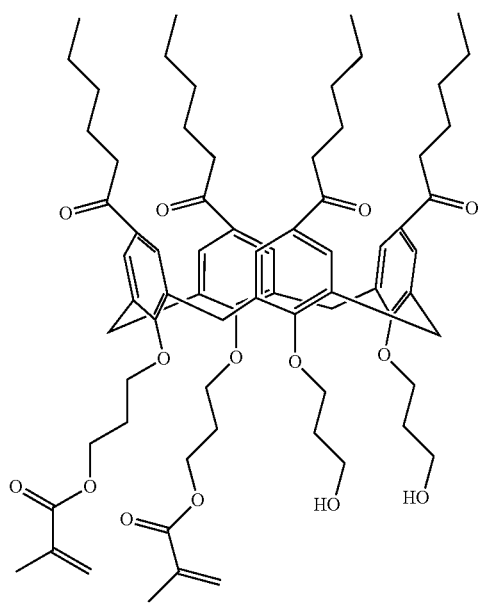
(10-1)
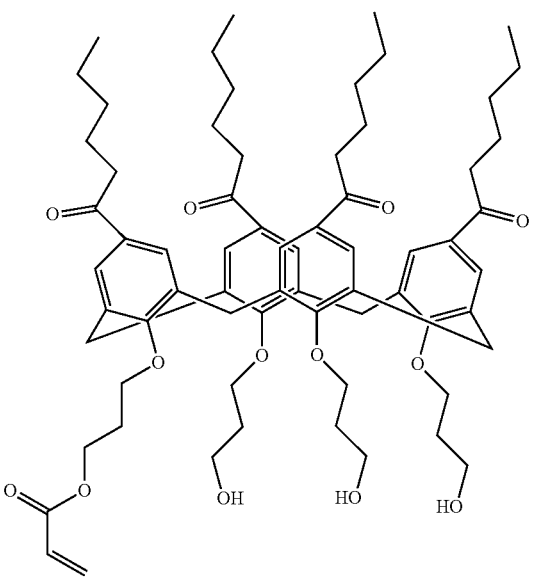

(10-2)

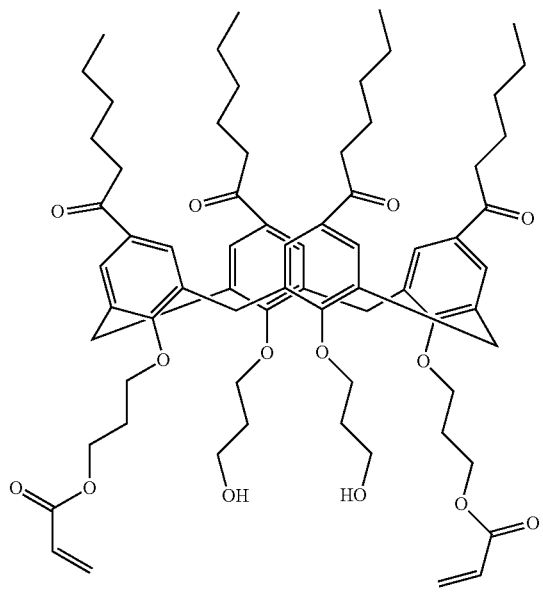

(10-4)

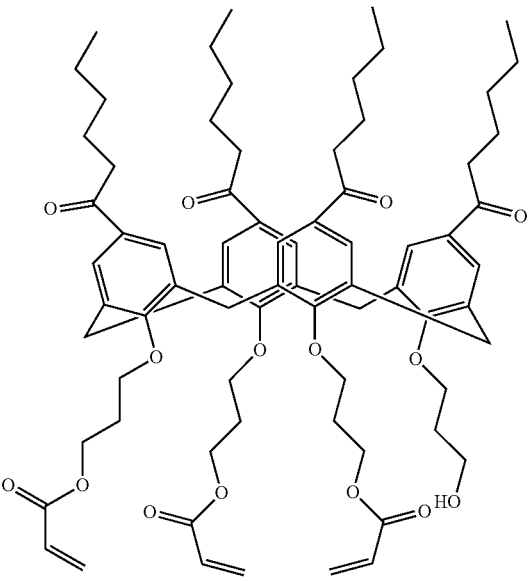

(10-3)

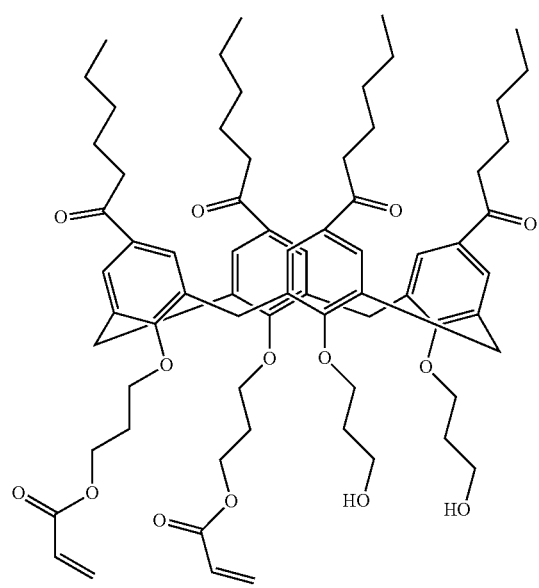

Synthesis Example 10

In a 500-mL four-neck flask equipped with a stirrer, a thermometer, and a reflux condenser, 92.6 g (113.33 mmol) of the compound obtained in Synthesis Example 2 and 944.52 g of diethylene glycol monomethyl ether were added and stirred. Subsequently, 46.4 ml (906.64 mmol) of hydrazine monohydrate was added to a white suspension solution, and further, 50.9 g (906.64 mmol) of potassium hydroxide pellets were added. After being stirred at 100° C. for 30 minutes, the contents were heated to reflux for 8 hours. After completion of the reaction, the mixture was cooled to 90° C., and then 92.6 ml of ion exchanged water was added. Stirring was performed for 30 minutes. The mixture solution was cooled to room temperature and transferred to a beaker. 6N hydrochloric acid was added until a pH of 1 was reached, and 300 g of chloroform was added. The reaction mixture was transferred to a separatory funnel to separate the organic layer. Next, the aqueous layer was extracted three times with 300 g of chloroform, and the organic layers were combined together. All the organic layers were predried with anhydrous magnesium sulfate and then filtered. The solvent was evaporated using an evaporator, and thus an orange viscous liquid was obtained. Methanol was added to cause repre-cipitation. White crystals that were formed were filtered out with a Kiriyama funnel and dried under vacuum (at 60° C. for 6 hours or more). Accordingly, a compound represented below, which was a target compound, was obtained. The compound was in an amount of 54.34 g. The yield was 63.0%.

[Chem. 39]

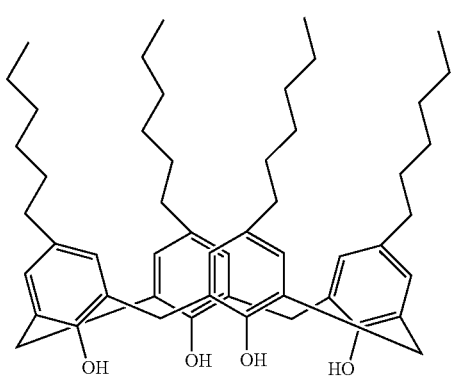

Synthesis Example 11

This example was carried out as in Synthesis Example 10 except that the compound obtained in Synthesis Example 3 was used instead of the compound obtained in Synthesis Example 2. Thus, a compound represented below, which was a target compound, was obtained. The compound was in an amount of 72.45 g. The yield was 83.1%.

[Chem. 40]

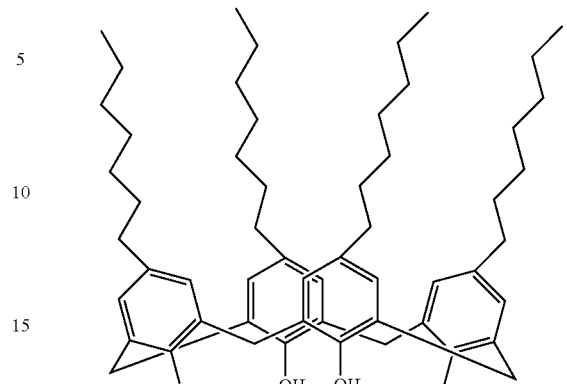

Synthesis Example 12

This example was carried out as in Synthesis Example 10 except that the compound obtained in Synthesis Example 4 was used instead of the compound obtained in Synthesis Example 2. Thus, a compound represented below, which was a target compound, was obtained. The compound was in an amount of 78.4 g. The yield was 82.7%.

[Chem. 41]

Synthesis Example 13

This example was carried out as in Synthesis Example 10 except that the compound obtained in Synthesis Example 5 was used instead of the compound obtained in Synthesis Example 2. Thus, a compound represented below, which was a target compound, was obtained. The compound was in an amount of 37.9 g. The yield was 96.0%.

[Chem. 42]

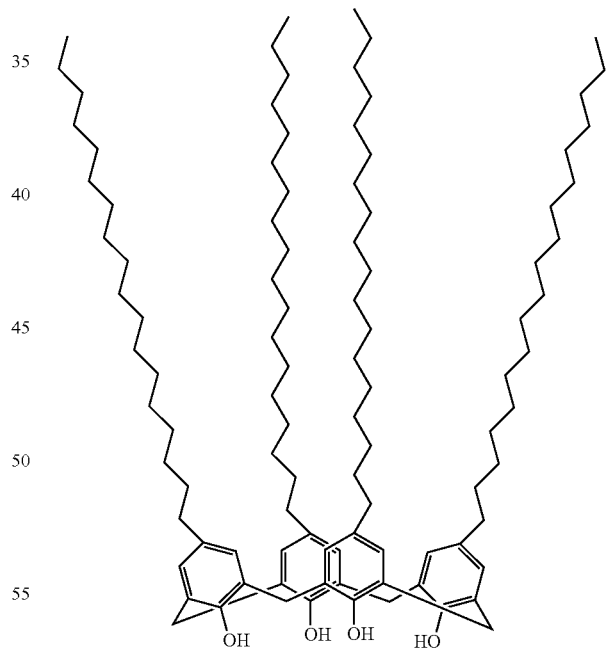

Synthesis Example 14

By referring to a publication (Tetrahedron Letters, 43(43), 7691-7693; 2002 and Tetrahedron Letters, 48(5), 905-12; 1992), a target compound was synthesized from the compound (α-1) in accordance with the scheme shown below (in an amount of 75 g, 66.6% yield).

[Chem. 43]

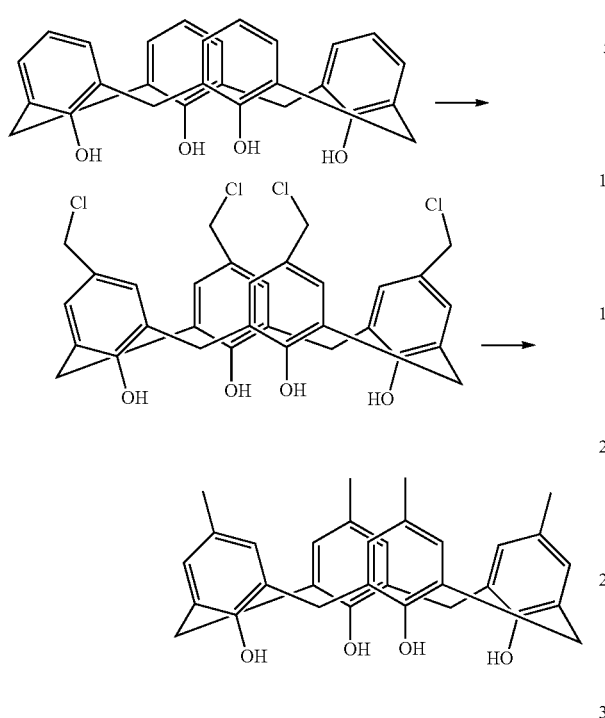

Example 11

This example was carried out as in Example 1 except that the compound obtained in Synthesis Example 10 was used instead of the compound obtained in Synthesis Example 2. Thus, compounds (11-1) and (11-2), shown below, were obtained. The compounds (11-1) and (11-2) were in amounts of 0.278 g (24.23% yield) and 0.413 g (31.9% yield), respectively.

[Chem. 44]

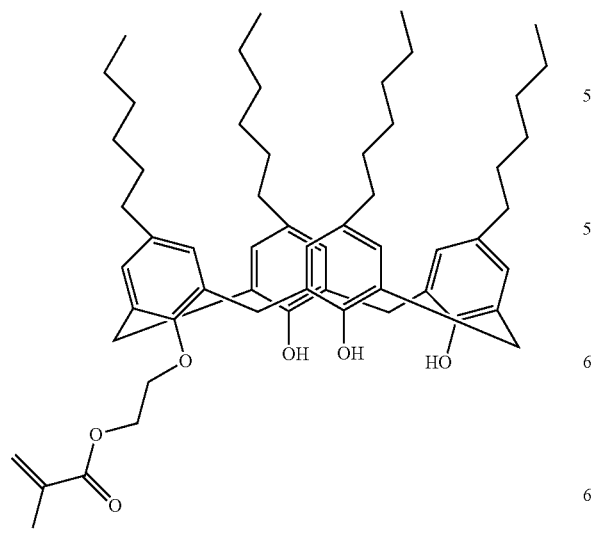

(11-1)

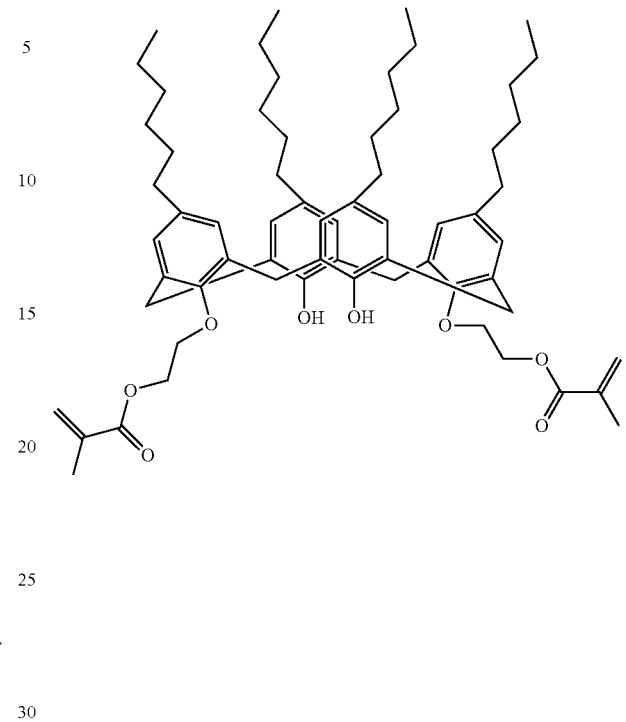

(11-2)

Example 12

This example was carried out as in Example 11 except that the compound obtained in Synthesis Example 11 was used instead of the compound obtained in Synthesis Example 10. Thus, compounds (12-1) and (12-2), shown below, were obtained. The compounds (12-1) and (12-2) were in amounts of 0.214 g (18.2% yield) and 0.421 g (31.3% yield), respectively.

[Chem. 45]

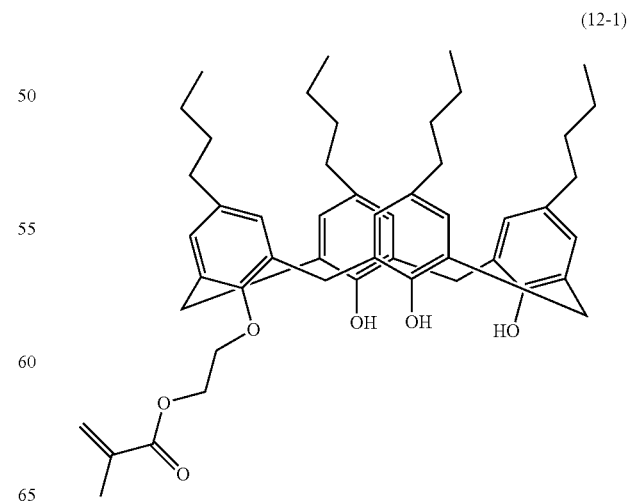

(12-1)

(12-2)

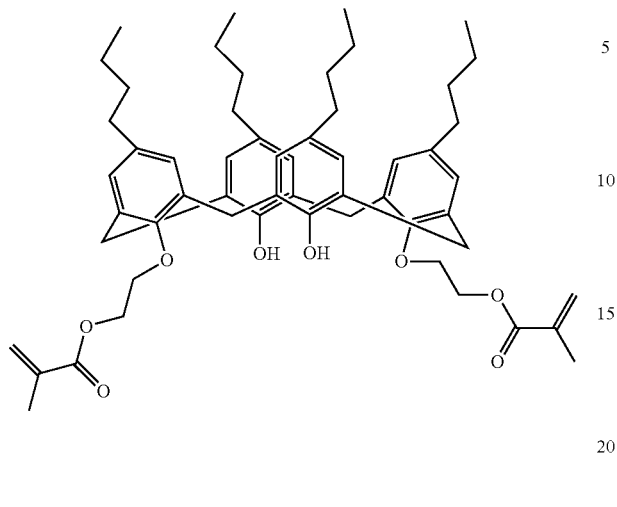

(13-2)

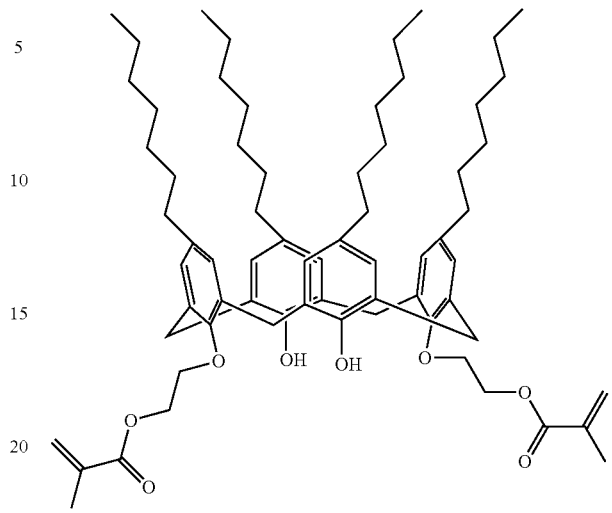

Example 13

This example was carried out as in Example 11 except that the compound obtained in Synthesis Example 12 was used instead of the compound obtained in Synthesis Example 10. Thus, compounds (13-1) and (13-2), shown below, were obtained. The compounds (13-1) and (13-2) were in amounts of 0.228 g (20.0% yield) and 0.378 g (29.7% yield), respectively.

[Chem. 46]

Example 14

This example was carried out as in Example 11 except that the compound obtained in Synthesis Example 13 was used instead of the compound obtained in Synthesis Example 10. Thus, compounds (14-1) and (14-2), shown below, were obtained. The compounds (14-1) and (14-2) were in amounts of 0.231 g (21.4% yield) and 0.761 g (65.8% yield), respectively.

[Chem. 47]

(14-1)

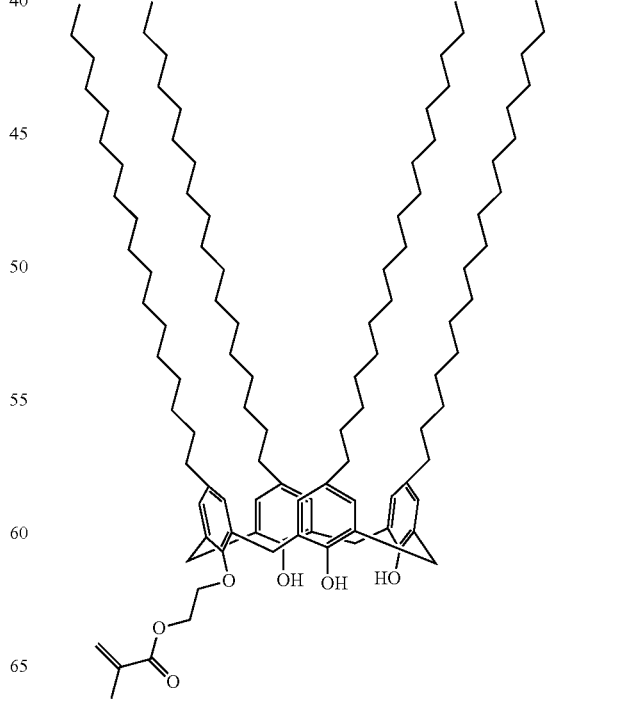

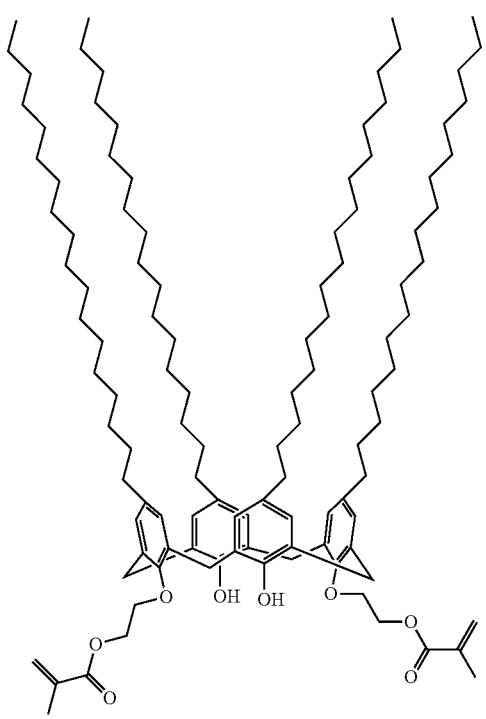

(14-2)

Example 15

This example was carried out as in Example 11 except that the compound obtained in Synthesis Example 14 was used instead of the compound obtained in Synthesis Example 10. Thus, compounds (15-1) and (15-2), shown below, were obtained. The compounds (15-1) and (15-2) were in amounts of 0.125 g (10.1% yield) and 0.213 g (14.5% yield), respectively.

[Chem. 48]

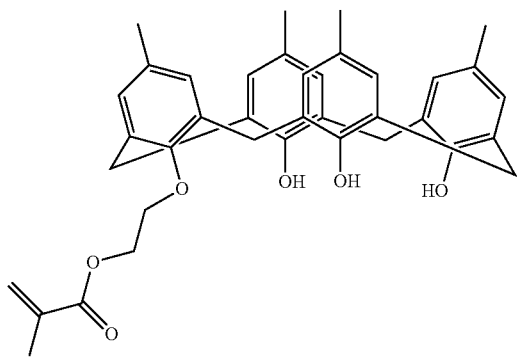

(15-1)

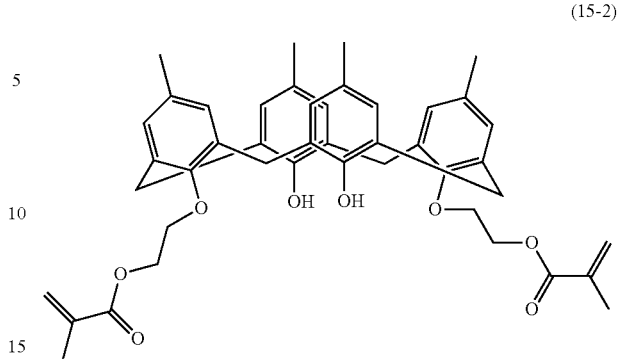

(15-2)

Example 16

This example was carried out as in Example 10 except that acrylic acid was used instead of methacrylic acid. Thus, compounds (16-1) and (16-2), shown below, were obtained. The compounds (16-1) and (16-2) were in amounts of 0.276 g (24.4% yield) and 0.451 g (35.9% yield), respectively.

[Chem. 49]

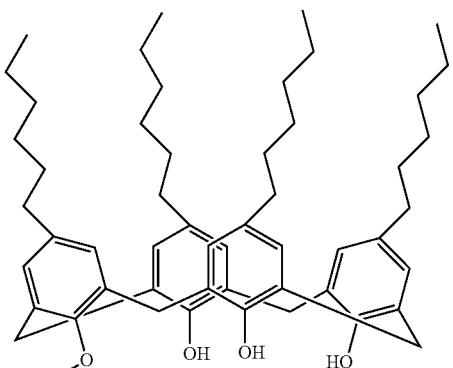

(16-1)

(16-2)

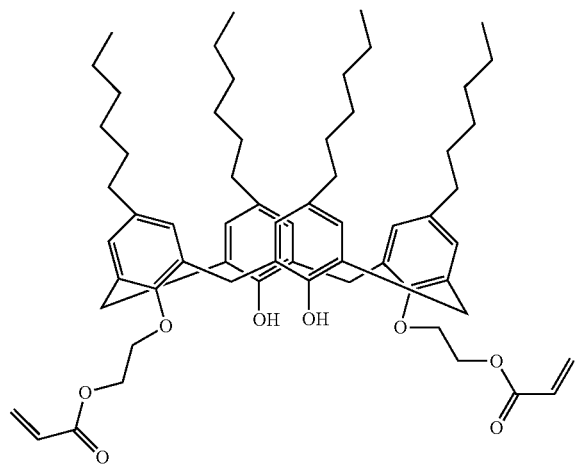

(17-2)

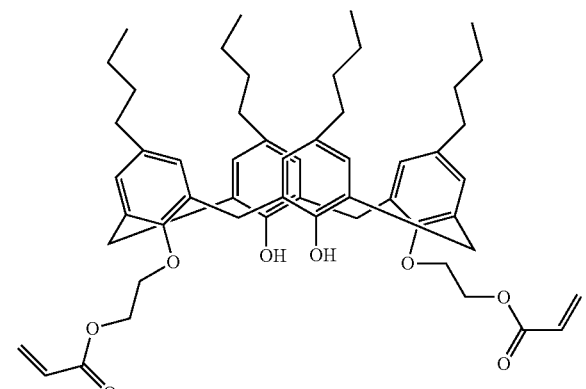

Example 17

This example was carried out as in Example 16 except that the compound obtained in Synthesis Example 11 was used instead of the compound obtained in Synthesis Example 10. Thus, compounds (17-1) and (17-2), shown below, were obtained. The compounds (17-1) and (17-2) were in amounts of 0.291 g (25.3% yield) and 0.491 g (37.7% yield), respectively.

[Chem. 50]

Example 18

This example was carried out as in Example 16 except that the compound obtained in Synthesis Example 12 was used instead of the compound obtained in Synthesis Example 10. Thus, compounds (18-1) and (18-2), shown below, were obtained. The compounds (18-1) and (18-2) were in amounts of 0.221 g (19.7% yield) and 0.354 g (28.5% yield), respectively.

[Chem. 51]

(17-1)

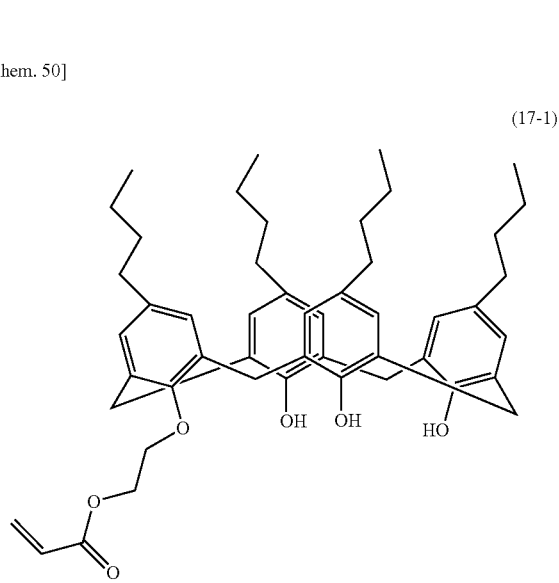

(18-1)

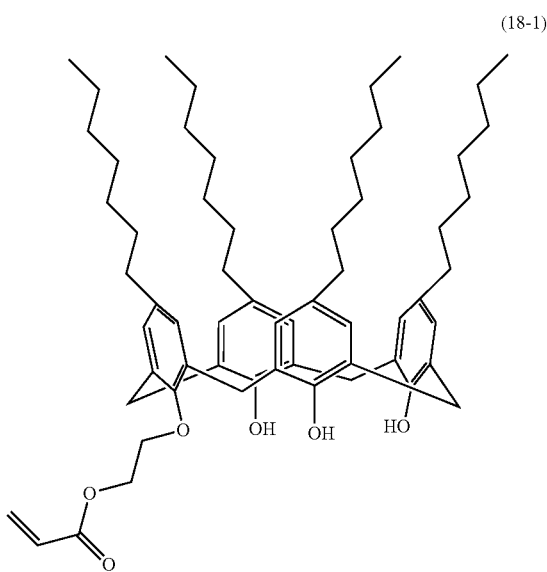

(18-2)

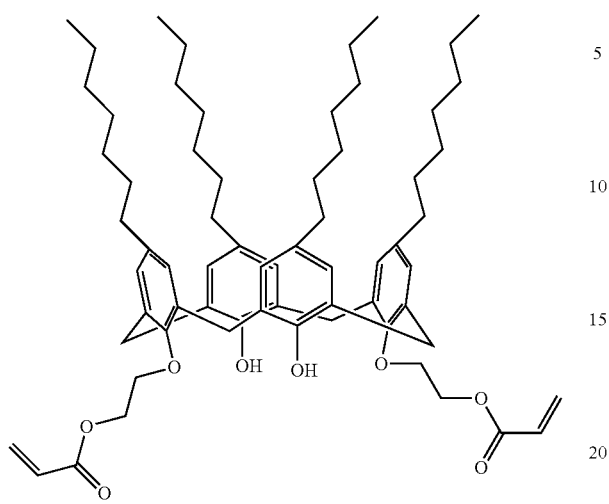

Example 19

This example was carried out as in Example 16 except that the compound obtained in Synthesis Example 13 was used instead of the compound obtained in Synthesis Example 10. Thus, compounds (19-1) and (19-2), shown below, were obtained. The compounds (19-1) and (19-2) were in amounts of 0.1801 g (16.9% yield) and 0.576 g (50.7% yield), respectively.

[Chem. 52]

(19-1)

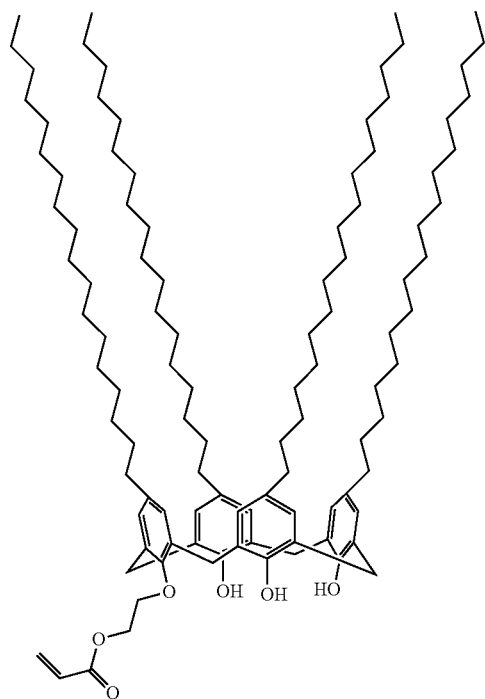

(19-2)

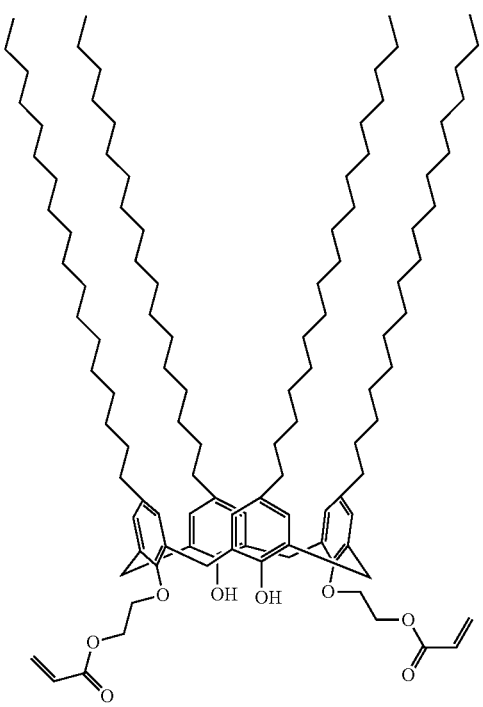

Example 20

This example was carried out as in Example 16 except that the compound obtained in Synthesis Example 14 was used instead of the compound obtained in Synthesis Example 10. Thus, compounds (20-1) and (20-2), shown below, were obtained. The compounds (20-1) and (20-2) were in amounts of 0.143 g (11.9% yield) and 0.345 g (24.5% yield), respectively.

[Chem. 53]

(20-1)

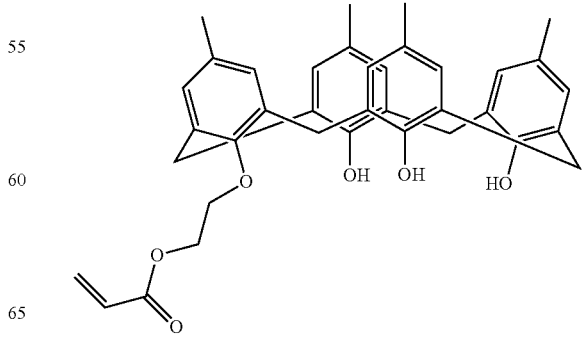

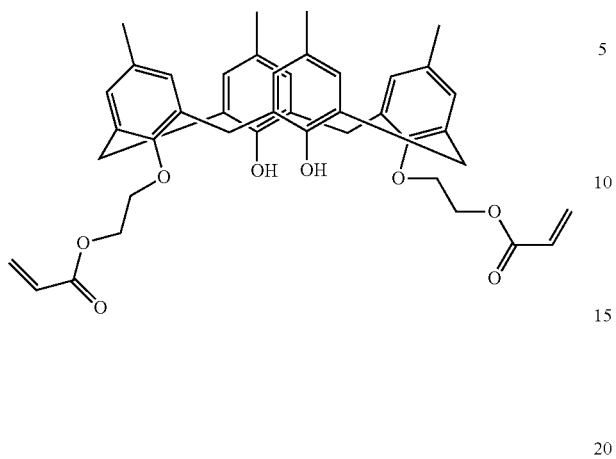

(20-2)

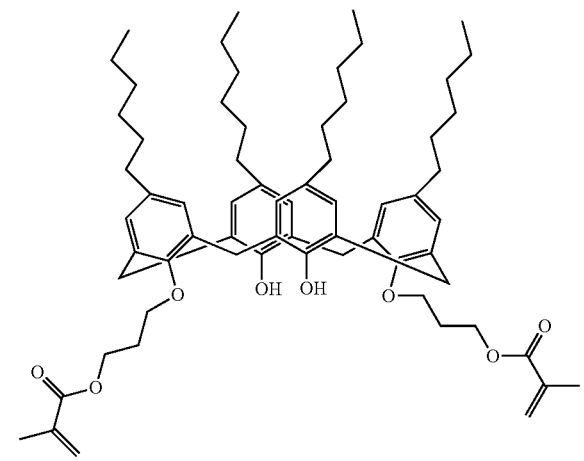

(21-2)

Example 21

This example was carried out as in Example 16 except that hydroxypropyl methacrylate was used instead of hydroxy methacrylate. Thus, compounds (21-1) and (21-2), shown below, were obtained. The compounds (21-1) and (21-2) were in amounts of 0.286 g (24.5% yield) and 0.432 g (32.4% yield), respectively.

Example 22

This example was carried out as in Example 16 except that 4-hydroxybutyl methacrylate was used instead of hydroxy methacrylate. Thus, compounds (22-1) and (22-2), shown below, were obtained. The compounds (22-1) and (22-2) were in amounts of 0.286 g (24.5% yield) and 0.449 g (33.7% yield), respectively.

[Chem. 54]

[Chem. 55]

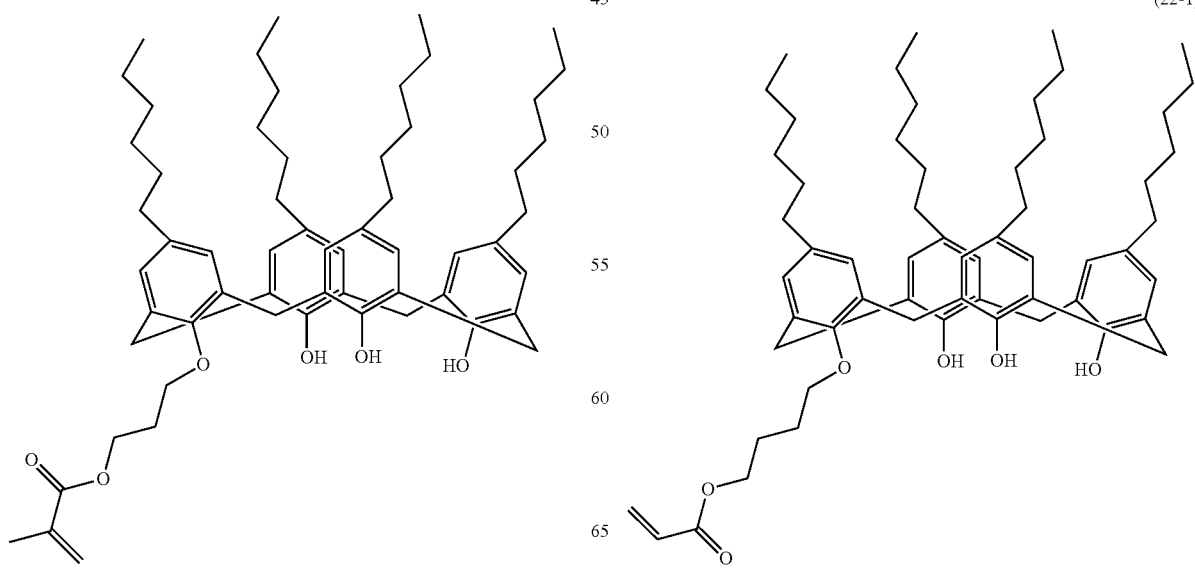

(21-1)      (22-1)

-continued (22-2)

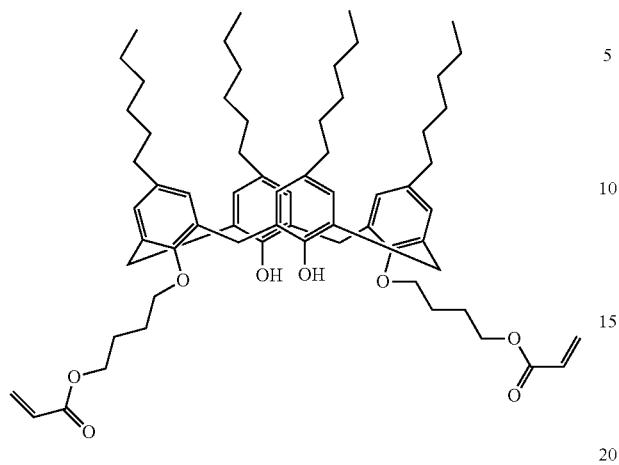

Synthesis Example 15

This example was carried out as in Synthesis Example 6 except that the compound obtained in Synthesis Example 10 was used instead of the compound obtained in Synthesis Example 2. Thus, a compound represented by the formula below was obtained. The compound was in an amount of 5.553 g (80.6% yield).

[Chem. 56]

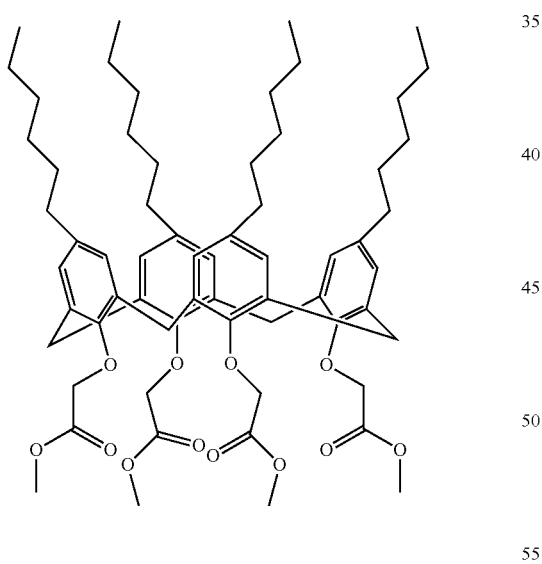

Synthesis Example 16

This example was carried out as in Synthesis Example 15 except that the compound obtained in Synthesis Example 11 was used instead of the compound obtained in Synthesis Example 10. Thus, a compound represented by the formula below was obtained. The compound was in an amount of 5.871 g (72.6% yield).

[Chem. 57]

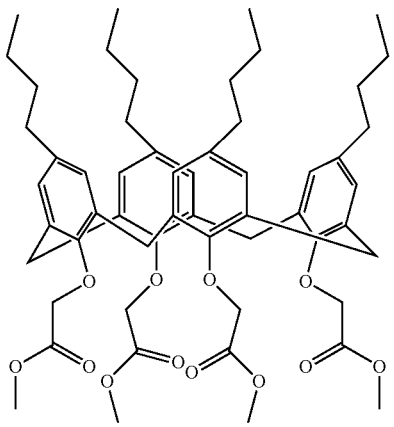

Synthesis Example 17

This example was carried out as in Synthesis Example 15 except that the compound obtained in Synthesis Example 12 was used instead of the compound obtained in Synthesis Example 10. Thus, a compound represented by the formula below was obtained. The compound was in an amount of 5.123 g (75.7% yield).

[Chem. 58]

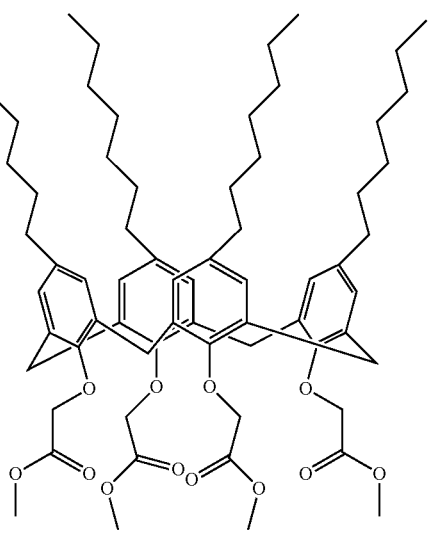

Synthesis Example 18

This example was carried out as in Synthesis Example 15 except that the compound obtained in Synthesis Example 13 was used instead of the compound obtained in Synthesis Example 10. Thus, a compound represented by the formula below was obtained. The compound was in an amount of 5.64 g (93.9% yield)

[Chem. 59]

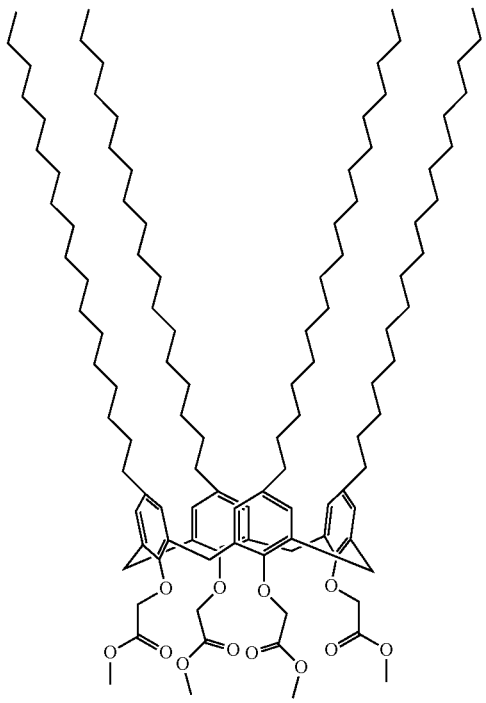

Synthesis Example 19

This example was carried out as in Synthesis Example 15 except that the compound obtained in Synthesis Example 14 was used instead of the compound obtained in Synthesis Example 10. Thus, a compound represented by the formula below was obtained. The compound was in an amount of 4.31 g (53.9% yield)

[Chem. 60]

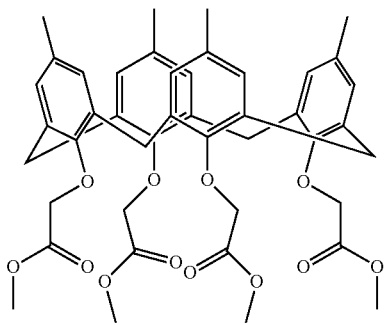

Synthesis Example 20

This example was carried out as in Synthesis Example 7 except that the compound obtained in Synthesis Example 15 was used instead of the compound obtained in Synthesis Example 6. Thus, a compound represented by the formula below was obtained. The compound was in an amount of 4.30 g (86.7% yield).

[Chem. 61]

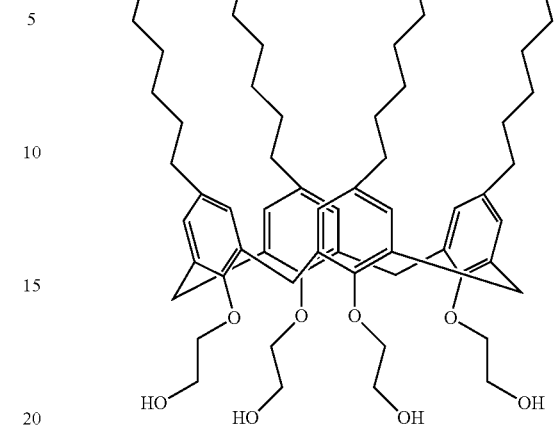

Synthesis Example 21

This example was carried out as in Synthesis Example 20 except that the compound obtained in Synthesis Example 16 was used instead of the compound obtained in Synthesis Example 15. Thus, a compound represented by the formula below was obtained. The compound was in an amount of 4.21 g (81.4% yield).

[Chem. 62]

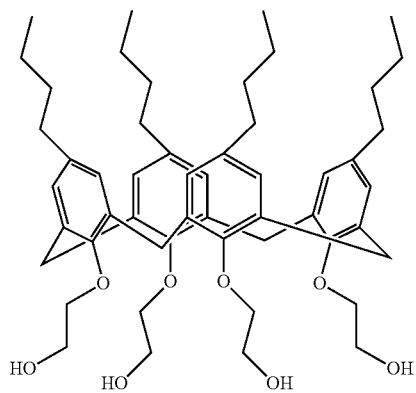

Synthesis Example 22

This example was carried out as in Synthesis Example 20 except that the compound obtained in Synthesis Example 17 was used instead of the compound obtained in Synthesis Example 15. Thus, a compound represented by the formula below was obtained. The compound was in an amount of 3.89 g (84.5% yield).

[Chem. 63]

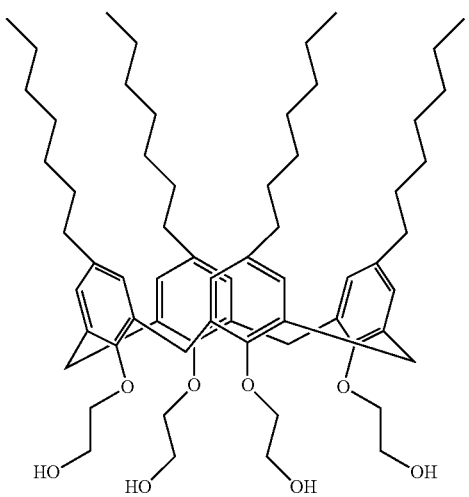

Synthesis Example 23

This example was carried out as in Synthesis Example 20 except that the compound obtained in Synthesis Example 18 was used instead of the compound obtained in Synthesis Example 15. Thus, a compound represented by the formula below was obtained. The compound was in an amount of 4.31 g (81.7% yield).

[Chem. 64]

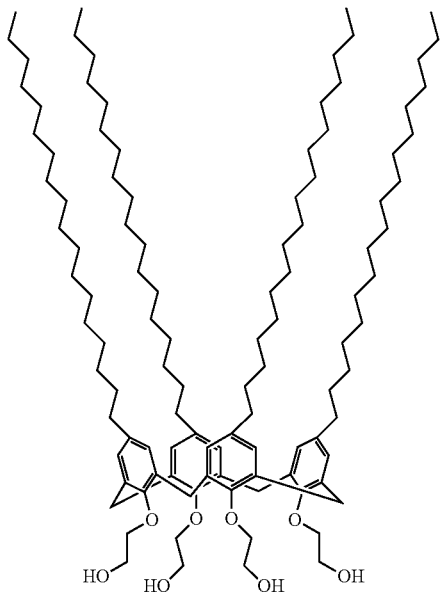

This example was carried out as in Synthesis Example 20 except that the compound obtained in Synthesis Example 19 was used instead of the compound obtained in Synthesis Example 15. Thus, a compound represented by the formula below was obtained. The compound was in an amount of 3.43 g (85.1% yield).

[Chem. 65]

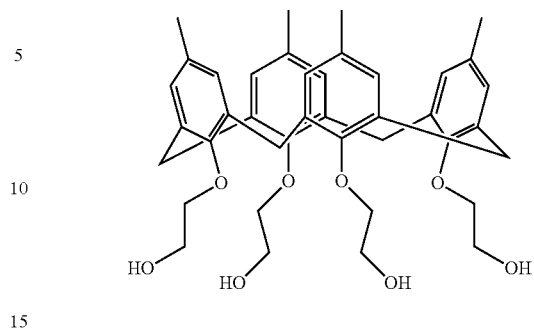

Example 23

In a 100-mL four-neck flask equipped with a stirrer, a thermometer, and a reflux condenser, 2.00 g (2.134 mmol) of the compound obtained in Synthesis Example 20, 7.69 g of tetrahydrofuran, 1.679 g (6.401 mmol) of triphenylphosphine, and 0.459 g (5.334 mmol) of methacrylic acid were added and stirred. A clear pale yellow solution. Subsequently, in an ice bath, 1.438 g (6.401 mmol) of diisopropyl azodicarboxylate was added dropwise over 30 minutes, and then a clear yellow solution was stirred at room temperature for 10 hours. Hexane was added to the reaction solution to remove by-products, such as triphenylphosphine, by precipitation, and thereafter chloroform extraction was carried out. The extracts were washed with water and saturated brine and subsequently dried with magnesium sulfate. The solvent was evaporated using an evaporator. An orange viscous liquid was purified by column chromatography (developing solvent:n-hexane:acetone=90:10). Thus, compounds (23-1) to (23-4), represented by the structural formulae below, were obtained. The compounds were dried under vacuum (at 60° C. for 6 hours or more). The compounds were in respective amounts of 0.21 g, 0.638 g, 0.470 g, and 0.213 g, with the respective yields being 9.79%, 27.9%, 20.5%, and 8.74%.

[Chem. 66]

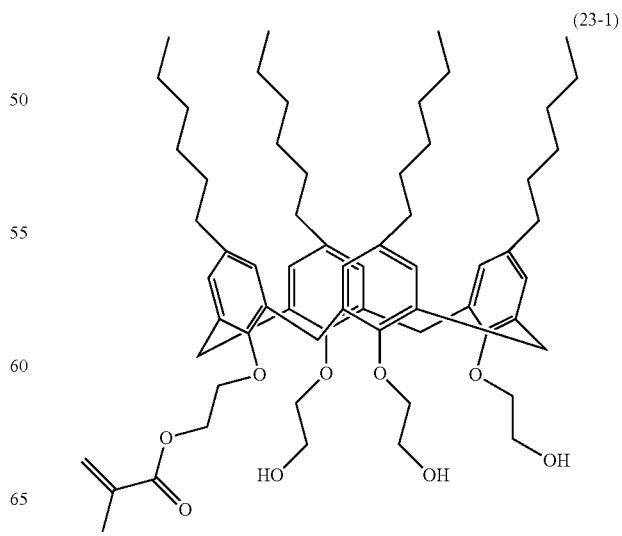

(23-1)

(23-2)
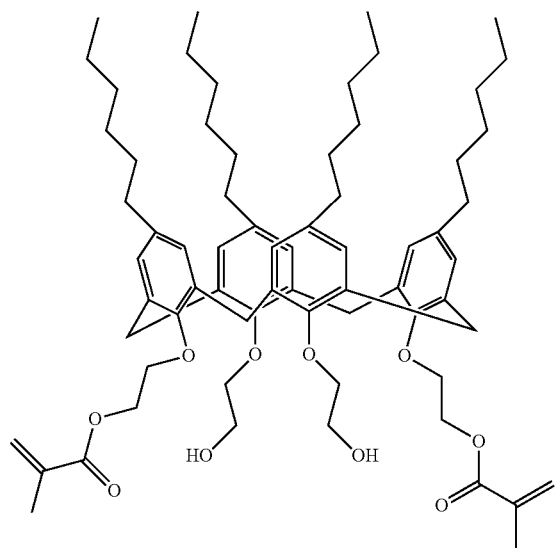
(23-4)
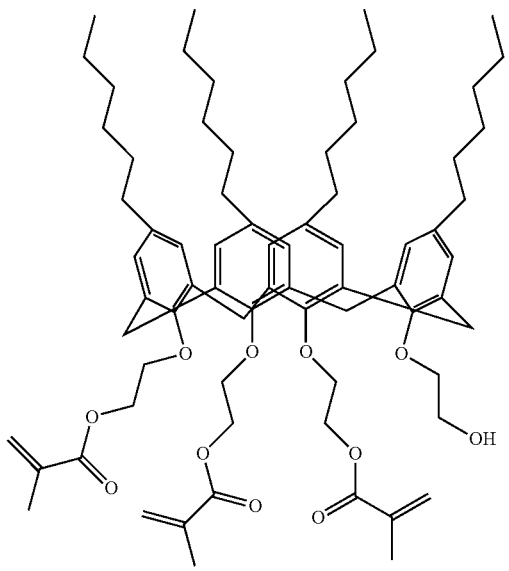
(23-3)
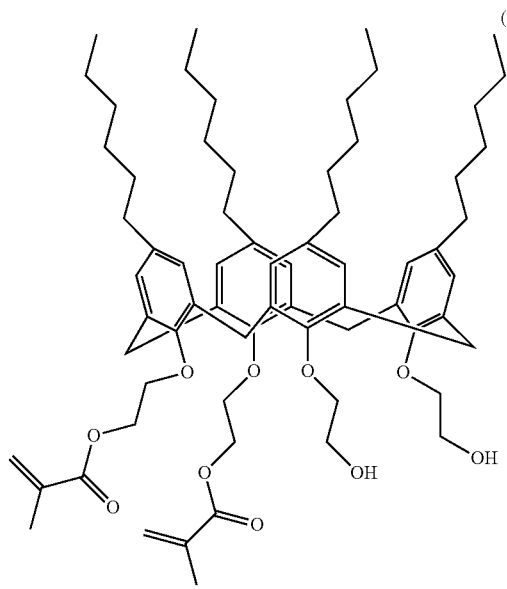
Example 24
This example was carried out as in Example 23 except that the compound obtained in Synthesis Example 21 was used instead of the compound obtained in Synthesis Example 20. Thus, compounds (24-1) to (24-4), represented by the structural formulae below, were obtained. The compounds were in respective amounts of 0.231 g (10.7% yield), 0.583 g (25.0% yield), 0.435 g (18.7% yield), and 0.334 g (13.4% yield).
[Chem. 67]
(24-1)
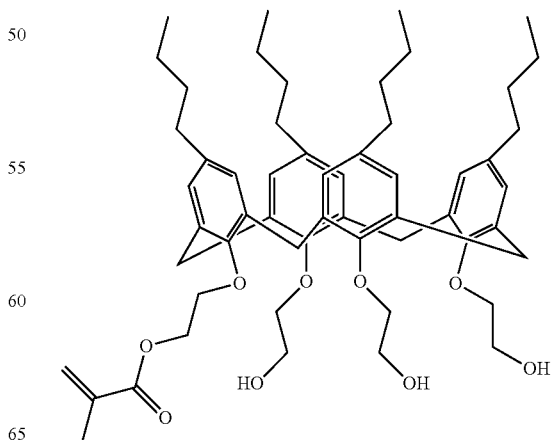

(24-2)
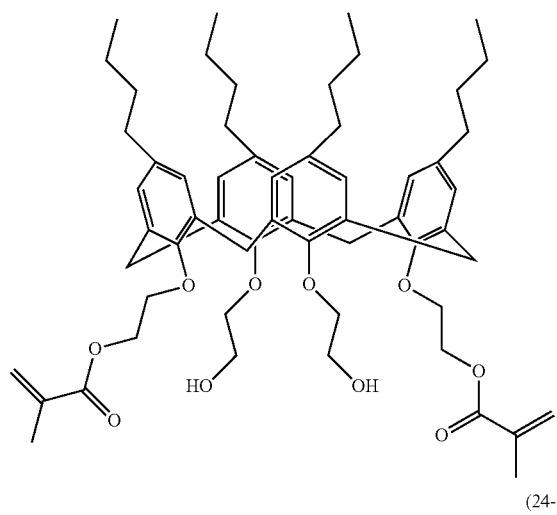
(24-3)
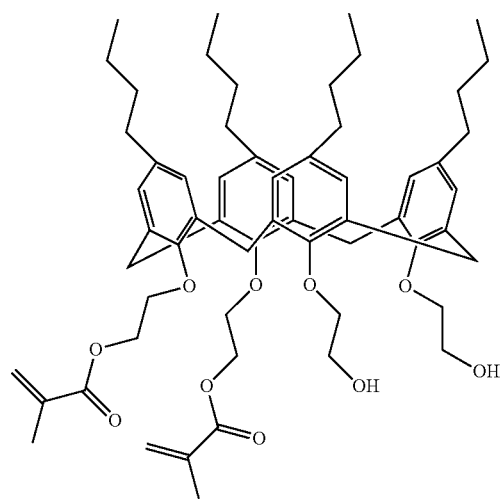
(24-4)
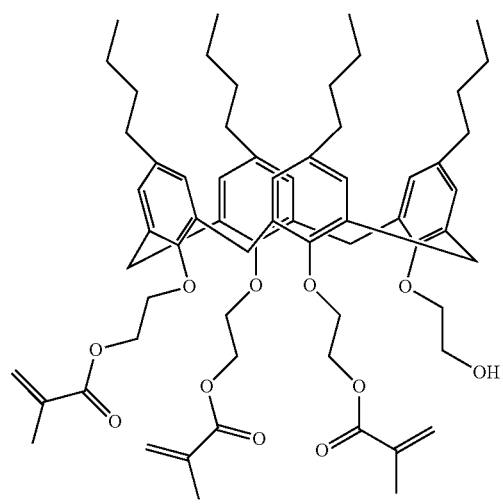
Example 25
This example was carried out as in Example 23 except that the compound obtained in Synthesis Example 22 was used instead of the compound obtained in Synthesis Example 20. Thus, compounds (25-1) to (25-4), represented by the structural formulae below, were obtained. The compounds were in respective amounts of 0.201 g (9.405% yield), 0.498 g (21.9% yield), 0.398 g (17.5% yield), and 0.265 g (11.0% yield).
[Chem. 68]
(25-1)
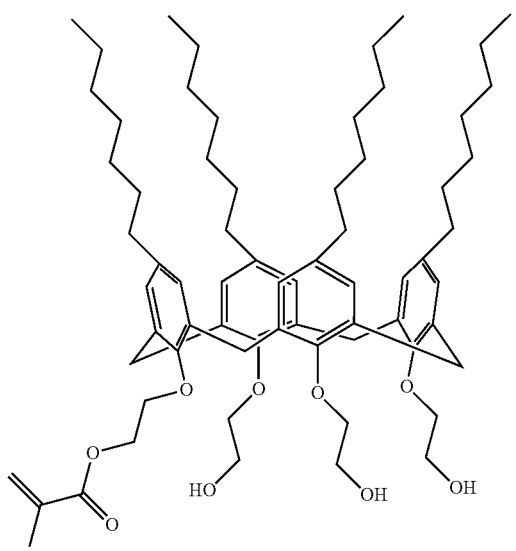
(25-2)
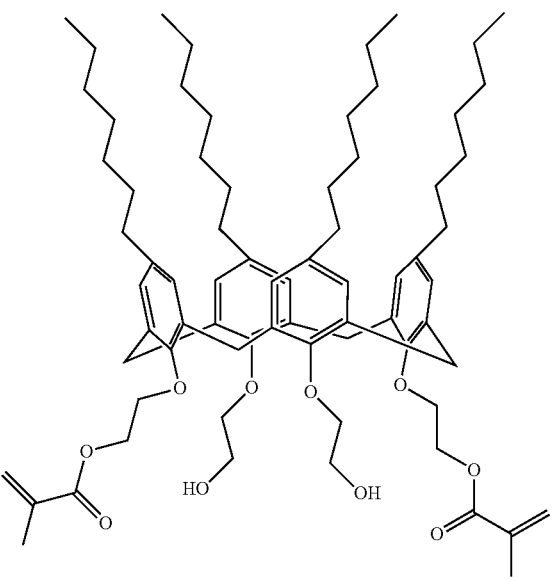

-continued
(25-3)
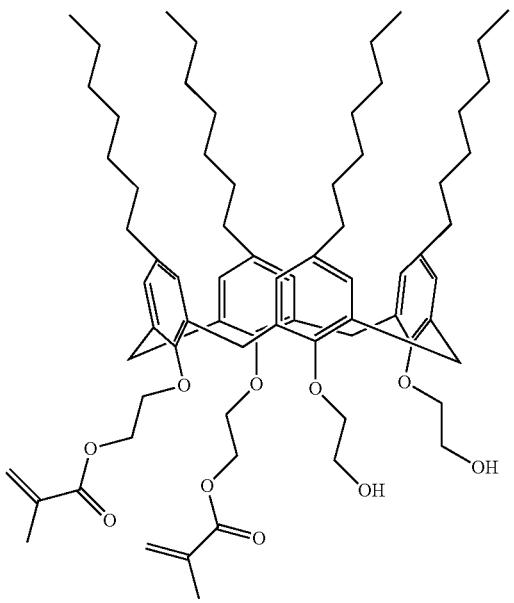
(25-4)
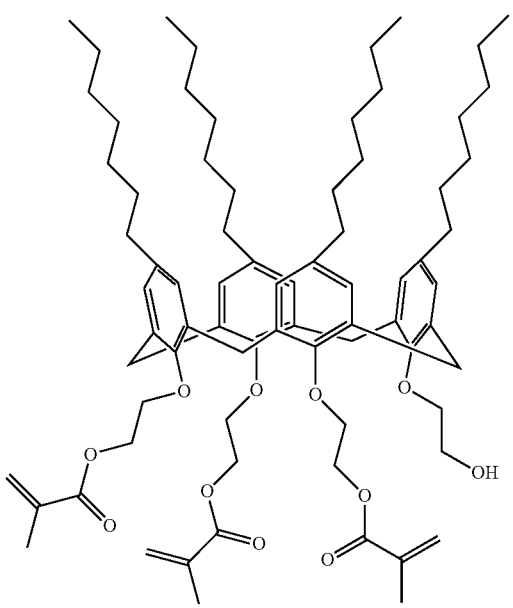
Example 26
This example was carried out as in Example 23 except that the compound obtained in Synthesis Example 23 was used instead of the compound obtained in Synthesis Example 20. Thus, compounds (26-1) to (26-4), represented by the structural formulae below, were obtained. The compounds were in respective amounts of 0.218 g (10.5% yield), 0.437 g (20.1% yield), 0.365 g (16.8% yield), and 0.228 g (10.1% yield).
[Chem. 69]
(26-1)
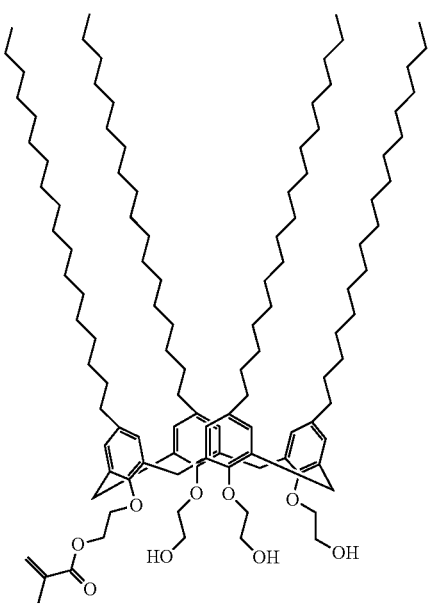
(26-2)
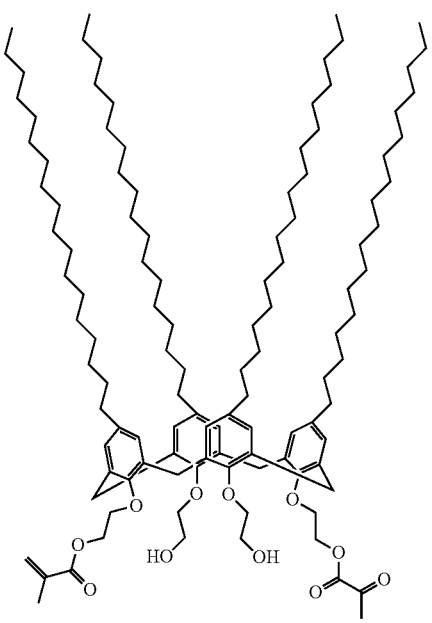

(26-3)
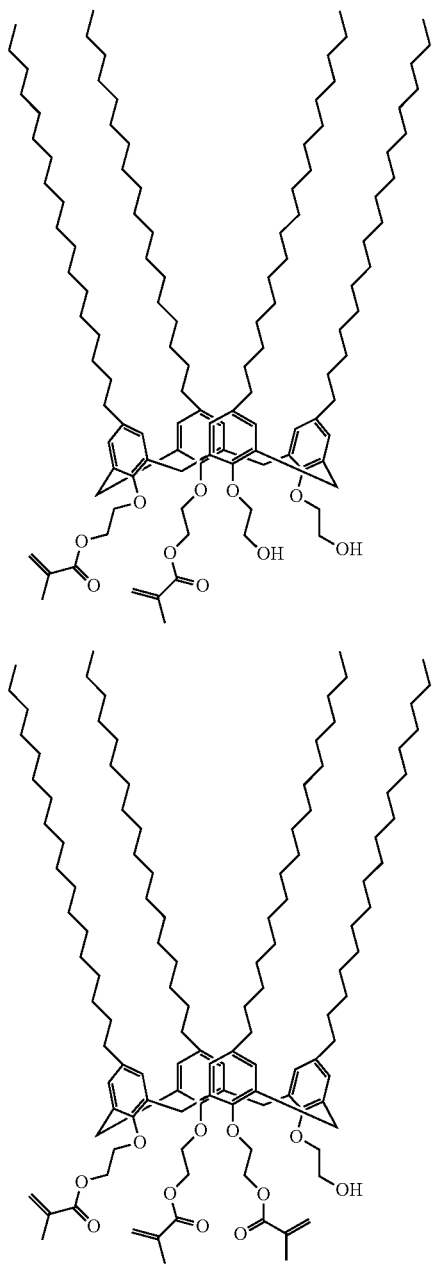
(26-4)
Example 27
This example was carried out as in Example 23 except that the compound obtained in Synthesis Example 24 was used instead of the compound obtained in Synthesis Example 20. Thus, compounds (27-1) to (27-4), represented by the structural formulae below, were obtained. The compounds were in respective amounts of 0.227 g (10.3% yield), 0.317 g (13.1% yield), 0.291 g (12.1% yield), and 0.289 g (14.8% yield).
[Chem. 70]
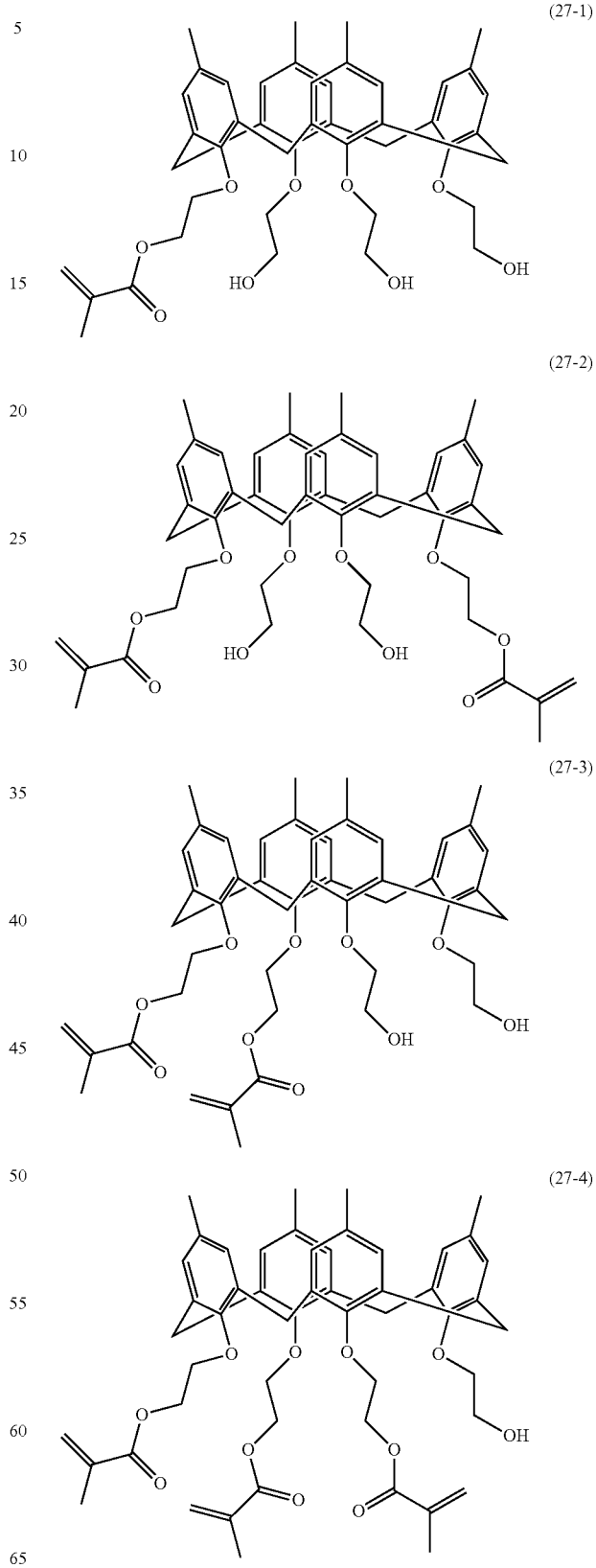

Example 28

This example was carried out as in Example 7 except that acrylic acid was used instead of methacrylic acid. Thus, compounds (28-1) to (28-4), represented by the structural formulae below, were obtained. The compounds were in respective amounts of 0.287 g (13.6% yield), 0.614 g (27.5%), 0.51 g (22.9%, yield), and 0.198 g (8.44%).

[Chem. 71]

(28-1)

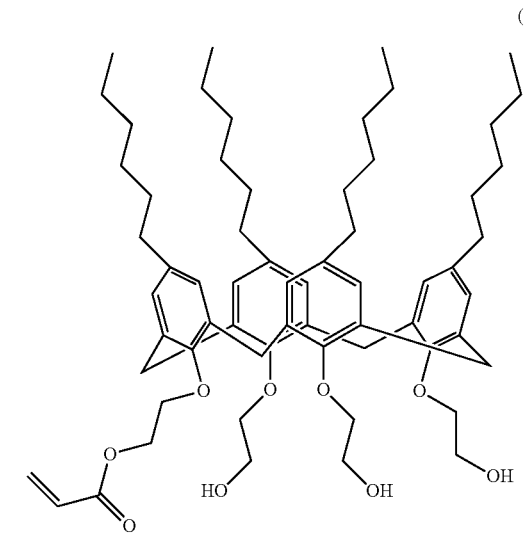

(28-2)

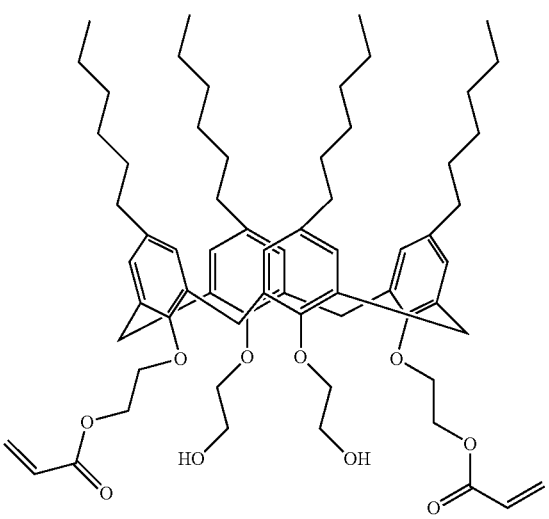

(28-3)

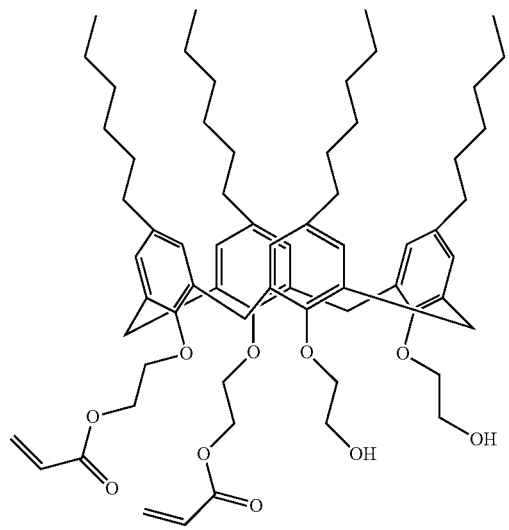

(28-4)

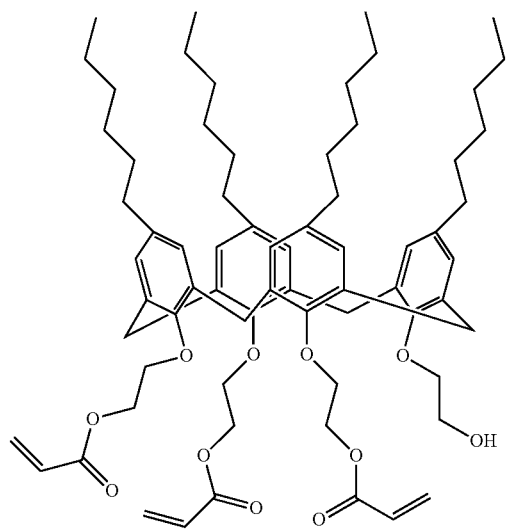

Synthesis Example 25

This example was carried out as in Synthesis Example 15 except that methyl bromopropionate was used instead of methyl bromoacetate. Thus, a compound represented by the formula below was obtained. The compound was in an amount of 4.89 g (67.3% yield).

[Chem. 72]

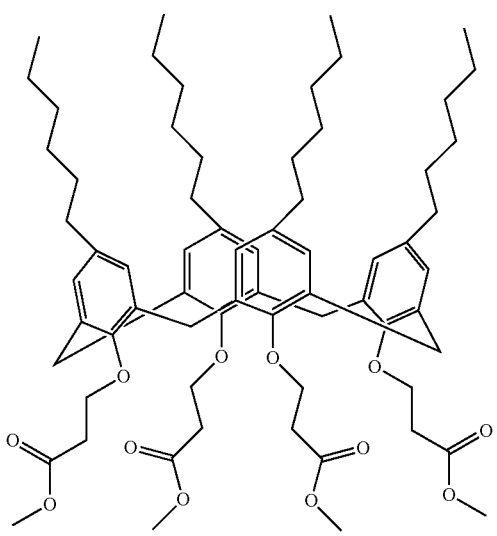

Synthesis Example 26

This example was carried out as in Synthesis Example 7 except that the compound obtained in Synthesis Example 25 was used instead of the compound obtained in Synthesis Example 6. Thus, a compound represented by the formula below was obtained. The compound was in an amount of 3.88 g (88.3% yield).

[Chem. 73]

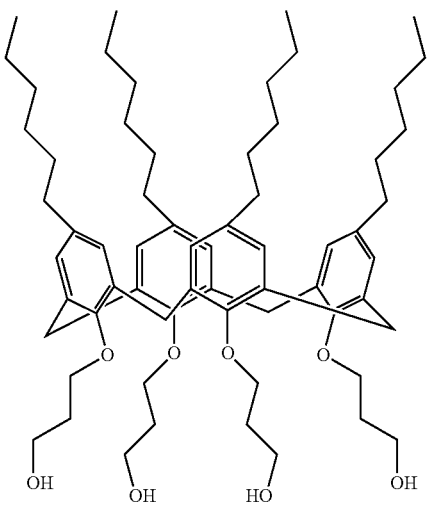

Example 29

This example was carried out as in Example 7 except that the compound obtained in Synthesis Example 26 was used instead of the compound obtained in Synthesis Example 13. Thus, compounds (29-1) to (29-4), represented by the structural formulae below, were obtained. The compounds were in respective amounts of 0.214 g (10.0% yield), 0.543 g (23.9% yield), 0.498 g (21.9% yield), and 0.211 g (8.75% yield).

[Chem. 74]

(29-1)

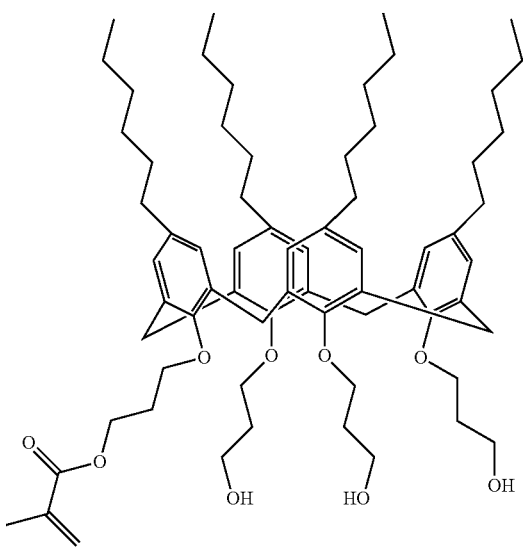

(29-2)

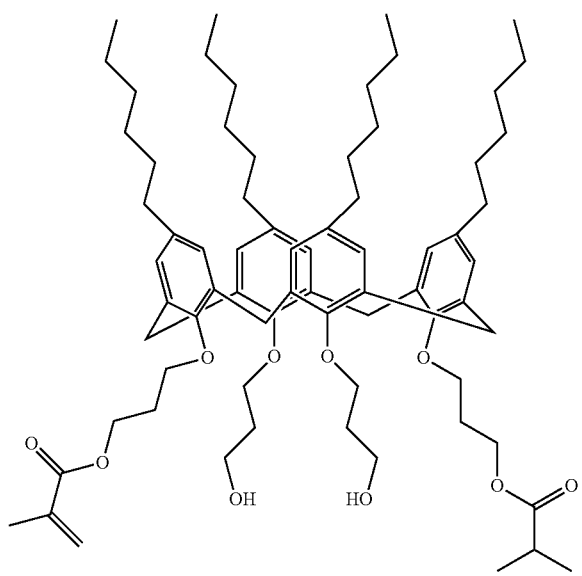

(29-3)
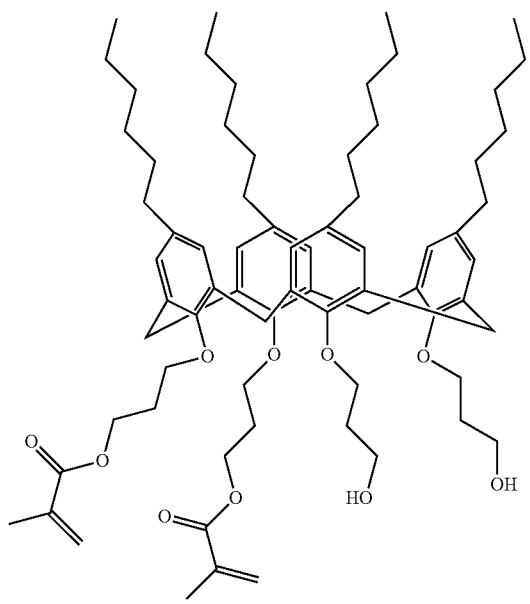
Example 30
This example was carried out as in Example 29 except that acrylic acid was used instead of methacrylic acid. Thus, compounds (30-1) to (30-4), represented by the structural formulae below, were obtained. The compounds were in respective amounts of 0.289 g (13.7% yield), 0.561 g (25.3% yield), 0.503 g (22.7% yield), and 0.298 g (12.8% yield).
[Chem. 75]
(30-1)
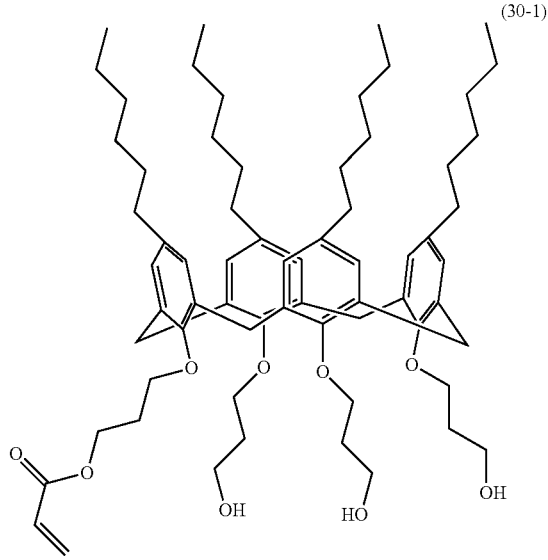
(29-4)
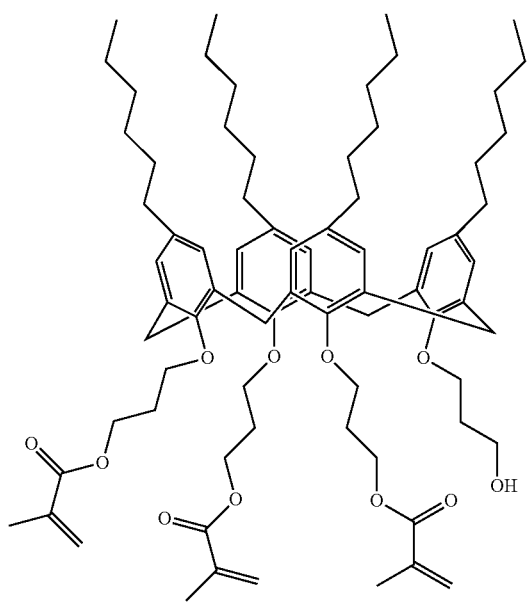
(30-2)

-continued

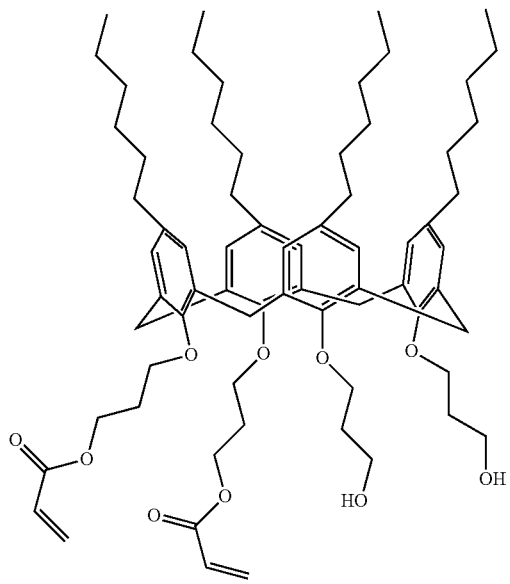

(30-3)

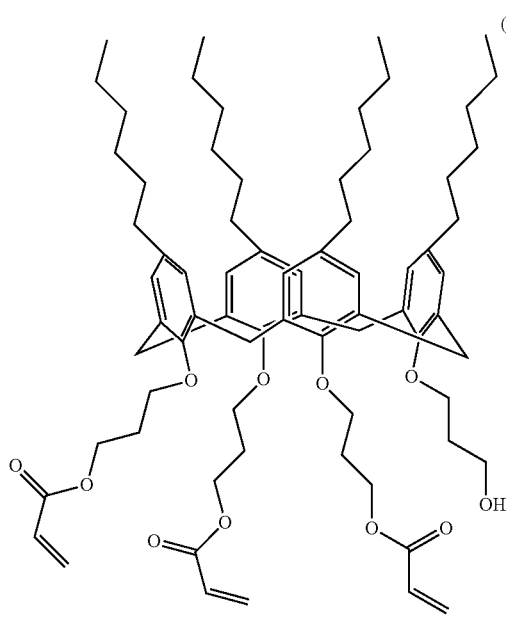

(30-4)

Synthesis Example 27

In a 50-mL four-neck flask equipped with a stirrer, a thermometer, and a reflux condenser, 1.00 g (1.015 mmol) of the compound (11-2) and 14.84 g of anhydrous N,N-dimethylformamide were added and stirred. Subsequently, in an ice bath, 0.162 g (4.059 mmol) of sodium hydride (60%, in paraffin oil) was slowly added. Furthermore, 0.91 g (4.059 mmol) of 1,3-dioxane-5-methanol-2,2-dimethyl-5-methanesulfonic acid was added, and stirring was performed at room temperature for 20 hours. Yellow oil was deposited on the wall. Ion exchanged water and acetic acid were added until a pH of 6 was reached. 30 g of chloroform was added. The reaction mixture was transferred to a separatory funnel to separate the organic layer. Next, the aqueous layer was extracted three times with 10 g of chloroform, and the organic layers were combined together. The organic layers were predried with anhydrous magnesium sulfate and then filtered. The solvent was evaporated using an evaporator. An orange viscous liquid was purified by column chromatography (developing solvent:n-hexane:acetone=95:5) Thus, a compound represented by the formula below was obtained. The compound was clear yellow and oily. The compound was dried under vacuum (at 60° C. for 6 hours or more). The compound was in an amount of 0.671 g, with the yield being 53.2%.

[Chem. 76]

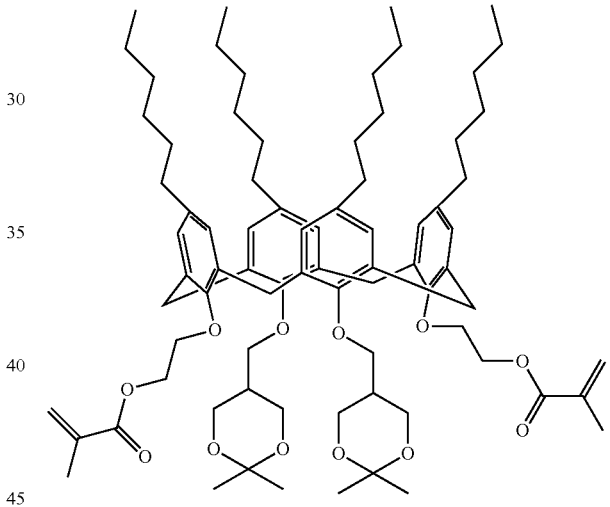

Example 31

In a 100-mL four-neck flask equipped with a stirrer, a thermometer, and a reflux condenser, 0.671 g (0.5404 mmol) of the compound obtained in Synthesis Example 27, 5.00 g of acetone, and 1.30 g (1.30 mmol) of 1N hydrochloric acid were added and stirred for 2 hours. The reaction solvent was evaporated using an evaporator. Subsequently, an orange viscous liquid that was obtained was purified by column chromatography (developing solvent:n-hexane:ethyl acetate=1:1). Thus, a compound (31-1), represented by the formula below, was obtained. The compound (31-1) was clear pale yellow and oily and was in an amount of 0.438 g. The yield was 69.8%.

[Chem. 77]

(31-1)

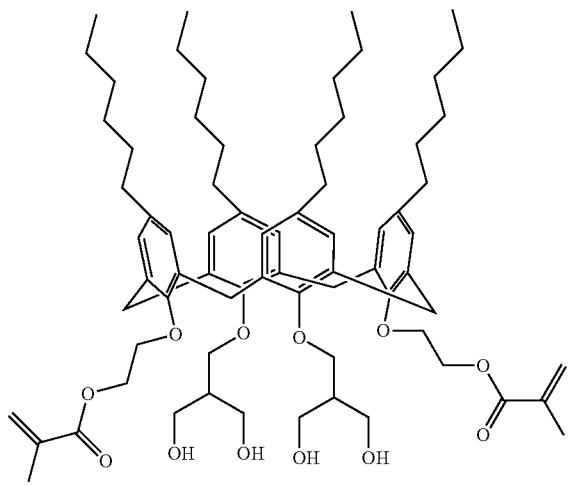

Example 32

In a 100-mL four-neck flask equipped with a stirrer, a thermometer, and a reflux condenser, 2.00 g (2.628 mmol) of the compound obtained in Synthesis Example 10, 9.474 g of tetrahydrofuran, 2.757 g (10.51 mmol) of triphenylphosphine, and 2.399 g (10.51 mmol) of glycerol dimethacrylate were added and stirred. Subsequently, in an ice bath, 2.361 g (10.51 mmol) of diisopropyl azodicarboxylate was added dropwise over 30 minutes. A clear red reaction solution was stirred at room temperature for 6 hours. Hexane was added to the reaction solution to remove by-products, such as triphenylphosphine, by precipitation, and thereafter chloroform extraction was carried out. The extracts were washed with water and saturated brine and subsequently dried with magnesium sulfate. The solvent was evaporated using an evaporator. A red viscous liquid that was obtained was purified by column chromatography (developing solvent:n-hexane:acetone=90:10). Thus, a compound (32-1), represented by the formula below, was obtained. The compound (32-1) was in an amount of 2.13 g. The yield was 68.6%.

[Chem. 78]

(32-1)

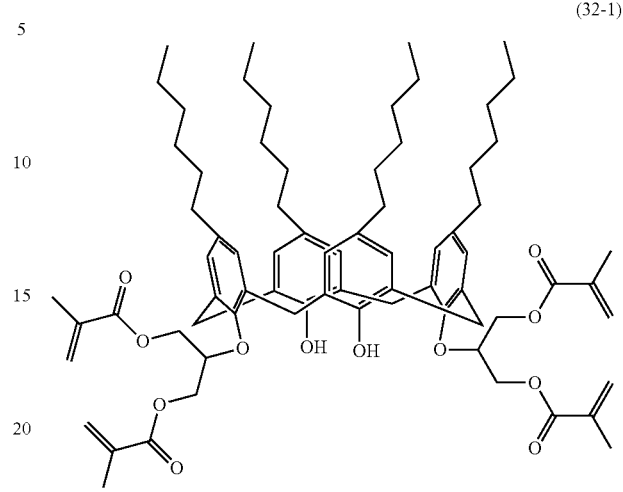

Synthesis Example 28

This example was carried out as in Synthesis Example 27 except that the compound (32-1) was used instead of the compound (11-2). Thus, a compound represented by the formula below was obtained. The compound was in an amount of 0.669 g. The yield was 55.0%.

[Chem. 79]

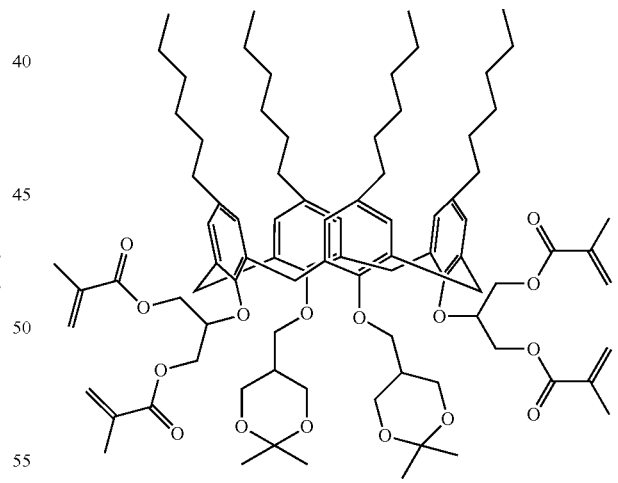

Example 33

This example was carried out as in Example 31 except that the compound obtained in Synthesis Example 28 was used instead of the compound obtained in Synthesis Example 27. Thus, a compound (33-1), represented by the formula below, was obtained. The compound (33-1) was in an amount of 0.436 g. The yield was 69.0%.

[Chem. 80]

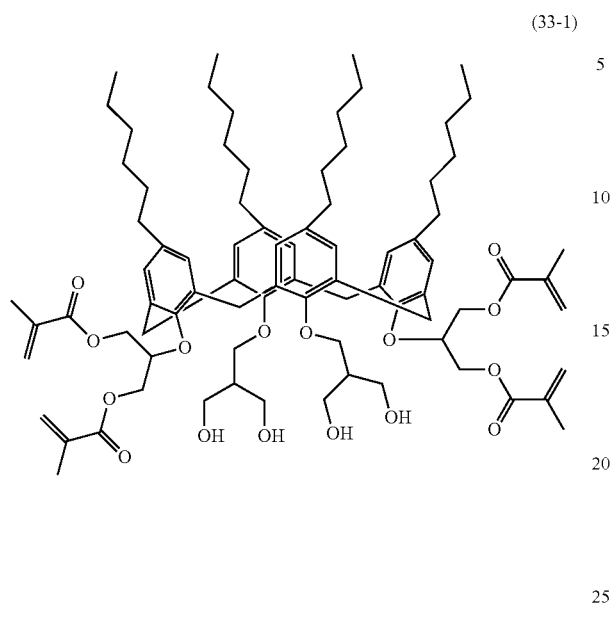

(33-1)

[Chem. 78]

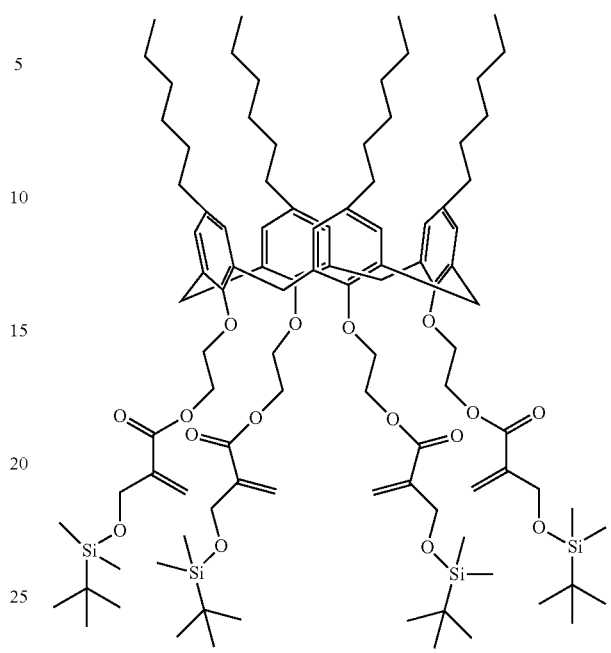

Synthesis Example 30

This example was carried out as in Synthesis Example 29 except that the compound obtained in Synthesis Example 21 was used instead of the compound obtained in Synthesis Example 20. Thus, a compound represented by the formula below was obtained. The compound was in an amount of 1.641 g. The yield was 57.3%.

[Chem. 82]

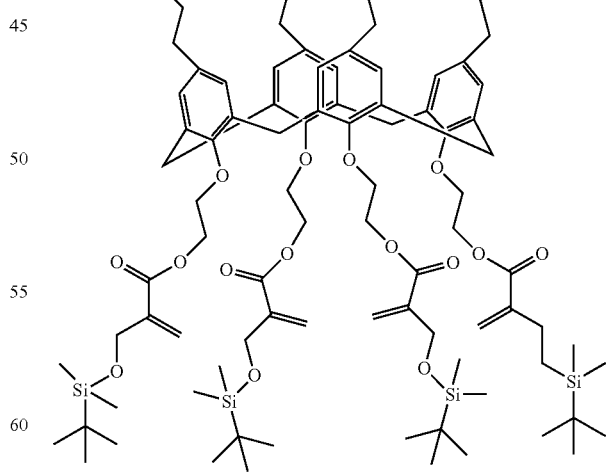

Synthesis Example 29

In a 50-mL four-neck flask equipped with a stirrer, a thermometer, and a reflux condenser, 2.00 g (2.424 mmol) of the compound obtained in Synthesis Example 20, 10.00 g of tetrahydrofuran, 1.2716 g (4.848 mmol) of triphenylphosphine, and 1.024 g (4.732 mmol) of 2-[[[1,1-imethylethyl)dimethylsilyl]oxy]-2-propenoic acid were added and stirred. Subsequently, the resulting reaction solution, which was a clear pale yellow solution, was cooled in an ice bath. 0.9803 g (4.848 mmol) of diisopropyl azodicarboxylate was added dropwise over 30 minutes. The resulting reaction solution, which was a clear pale yellow solution, was stirred at room temperature for 6 hours. Hexane was added to the reaction solution to remove by-products, such as triphenylphosphine, by precipitation, and thereafter chloroform extraction was carried out. The extracts were washed with water and saturated brine and subsequently dried with magnesium sulfate. The solvent was evaporated using an evaporator. A red viscous liquid that was obtained was purified by column chromatography (developing solvent:n-hexane:acetone=95:5). Thus, a compound represented by the formula below was obtained. The compound was in an amount of 1.891 g. The yield was 48.2%.

This example was carried out as in Synthesis Example 29 except that the compound obtained in Synthesis Example 22 was used instead of the compound obtained in Synthesis Example 20. Thus, a compound represented by the formula below was obtained. The compound was in an amount of 1.880 g. The yield was 79.0%.

[Chem. 83]

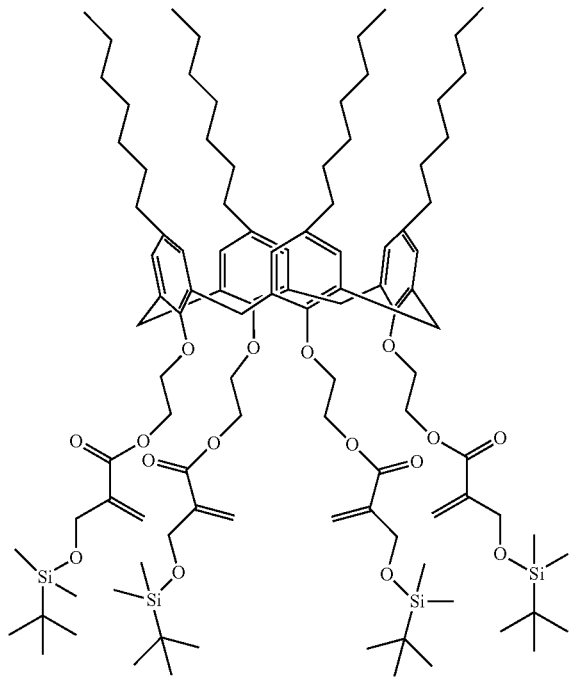

[Chem. 84]

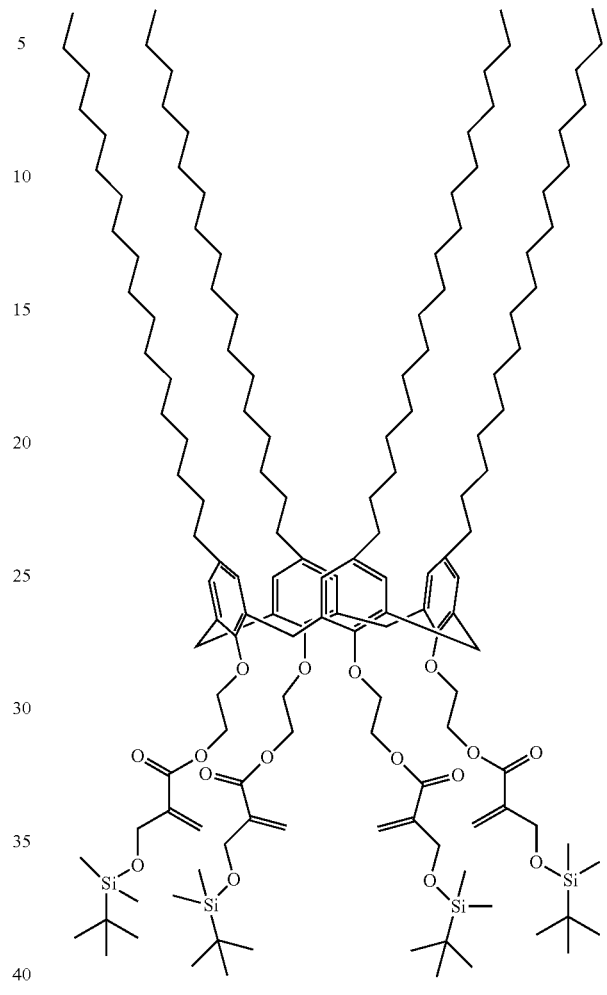

Synthesis Example 32

This example was carried out as in Synthesis Example 29 except that the compound obtained in Synthesis Example 23 was used instead of the compound obtained in Synthesis Example 20. Thus, a compound represented by the formula below was obtained. The compound was in an amount of 2.132 g. The yield was 71.4%.

Synthesis Example 33

This example was carried out as in Synthesis Example 29 except that the compound obtained in Synthesis Example 24 was used instead of the compound obtained in Synthesis Example 20. Thus, a compound represented by the formula below was obtained. The compound was in an amount of 1.762 g. The yield was 39.9%.

[Chem. 85]

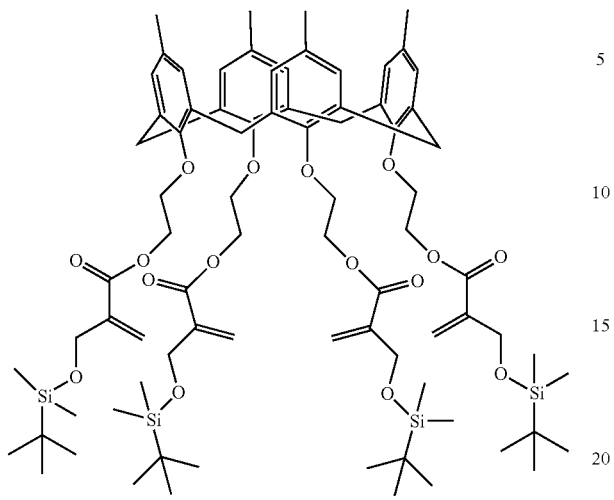

[Chem. 86]

(34-1)

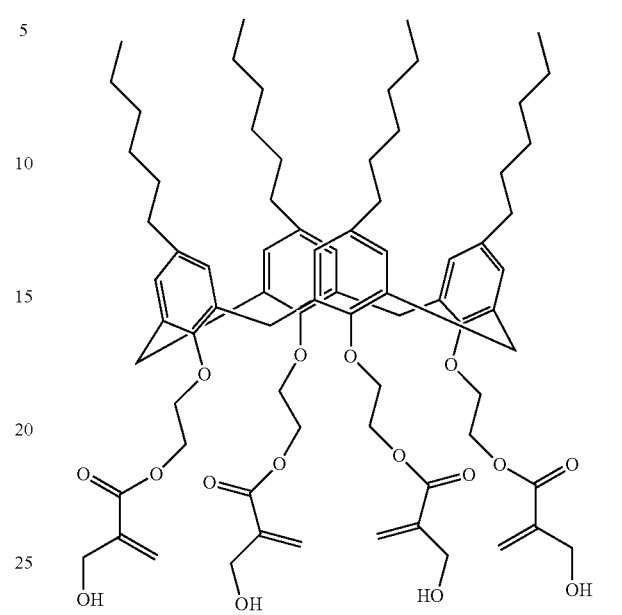

Example 34

In a 100-mL four-neck flask equipped with a stirrer, a thermometer, and a reflux condenser, 1.891 g (1.168 mmol) of the compound obtained in Synthesis Example 29, 50.00 g of tetrahydrofuran, and 0.3367 g (5.606 mmol) of acetic acid were added and stirred. Subsequently, the mixture solution, which was clear and colorless, was cooled in an ice bath. 5.61 ml (5.61 mmol) of tetrabutylammonium fluoride (ca. 1 mol/L in tetrahydrofuran) was slowly added dropwise with stirring. The resulting reaction solution, which was a clear pale yellow solution, was subsequently stirred at room temperature for 6 hours. In an ice bath, ion exchanged water was added to terminate the reaction. Subsequently, 30 g of chloroform was added. The reaction mixture was transferred to a separatory funnel to separate the organic layer. Next, the aqueous layer was extracted three times with 30 g of chloroform, and the organic layers were combined together. The organic layers were predried with anhydrous magnesium sulfate and then filtered. The solvent was evaporated using an evaporator, and thus a clear red liquid was obtained. The liquid was purified by column chromatography (developing solvent:n-hexane:acetone=95:5) Chloroform/methanol was added to a clear pale yellow oily product that was obtained, to cause reprecipitation. The crystals were filtered out with a Kiriyama funnel, and white crystals that were obtained were dried under vacuum (at 60° C. for 6 hours or more). Thus, a compound (34-1), represented by the formula below, was obtained. The compound (34-1) was in an amount of 0.8451 g. The yield was 62.3%.

Example 35

This example was carried out as in Example 34 except that the compound obtained in Synthesis Example 30 was used instead of the compound obtained in Synthesis Example 29. Thus, a compound (35-1), represented by the formula below, was obtained. The compound (35-1) was in an amount of 0.639 g. The yield was 54.3%.

[Chem. 87]

(35-1)

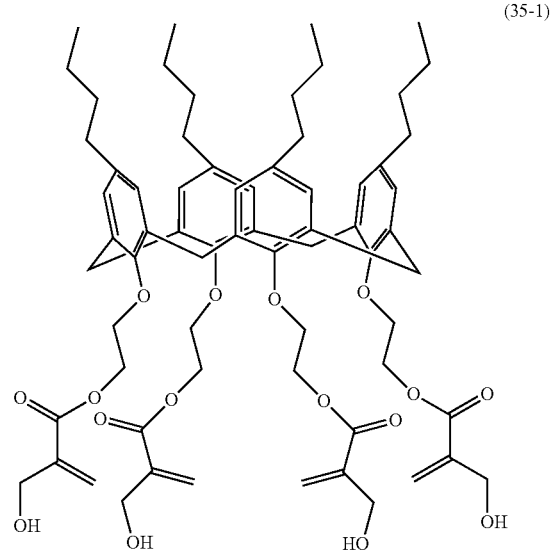

Example 36

This example was carried out as in Example 34 except that the compound obtained in Synthesis Example 31 was used instead of the compound obtained in Synthesis Example 29. Thus, a compound (36-1), represented by the formula below, was obtained. The compound (36-1) was in an amount of 0.873 g. The yield was 62.4%.

[Chem. 88]

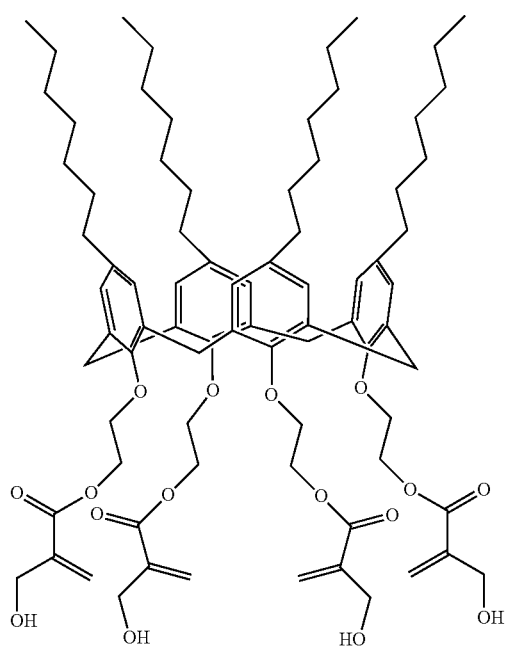

(36-1)

[Chem. 89]

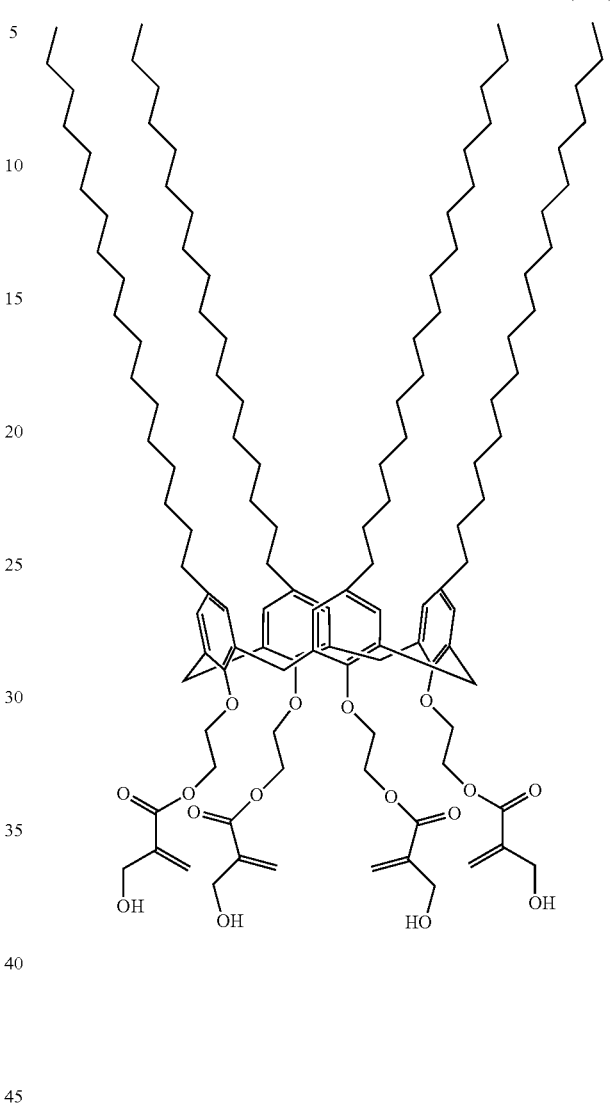

(37-1)

Example 37

This example was carried out as in Example 34 except that the compound obtained in Synthesis Example 32 was used instead of the compound obtained in Synthesis Example 29. Thus, a compound (37-1), represented by the formula below, was obtained. The compound (37-1) was in an amount of 1.092 g. The yield was 63.2%.

Example 38

This example was carried out as in Example 34 except that the compound obtained in Synthesis Example 33 was used instead of the compound obtained in Synthesis Example 29. Thus, a compound (38-1), represented by the formula below, was obtained. The compound (38-1) was in an amount of 0.654 g. The yield was 54.2%.

[Chem. 90]

(38-1)

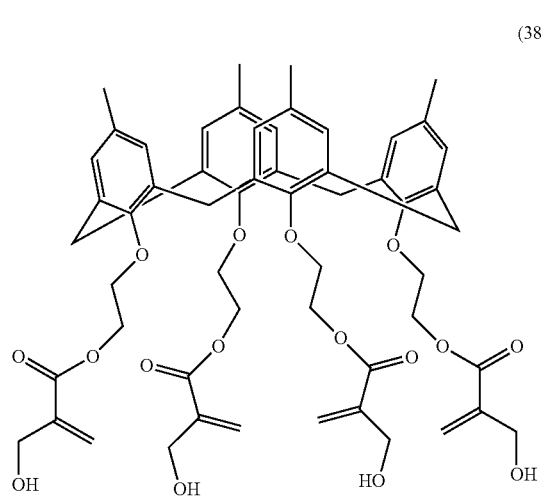

Synthesis Example 34

In a 100-mL four-neck flask equipped with a stirrer, a thermometer, and a reflux condenser, 2.00 g (1.570 mmol) of the compound obtained in Synthesis Example 20, 6.80 g (94.30 mmol) of tetrahydrofuran, 0.824 g (3.141 mmol) of triphenylphosphine, and 0.706 g (3.065 mmol) of 4-[[[1,1-dimethylethyl)dimethylsilyl]oxy]-2-methylene butanoic acid were added and stirred. A clear pale yellow solution. Subsequently, in an ice bath, 0.635 g (3.140 mmol) of diisopropyl azodicarboxylate was added dropwise over 30 minutes. A clear pale yellow solution. Stirring was performed at room temperature for 6 hours. Hexane was added to the reaction solution to remove by-products, such as triphenylphosphine, by precipitation, and thereafter chloroform extraction was carried out. The extracts were washed with water and saturated brine and subsequently dried with magnesium sulfate. The solvent was evaporated using an evaporator. A red viscous liquid was subjected to column chromatography (developing solvent:n-hexane:acetone=95: 5) Thus, a clear pale yellow liquid was obtained. The solvent was concentrated, and then chloroform/methanol was added to cause reprecipitation. White crystals were filtered out with a Kiriyama funnel, and white crystals that were obtained were dried under vacuum (at 60° C. for 6 hours or more). Thus, a compound represented by the formula below was obtained. The compound was in an amount of 2.420 g. The yield was 72.6%.

[Chem. 91]

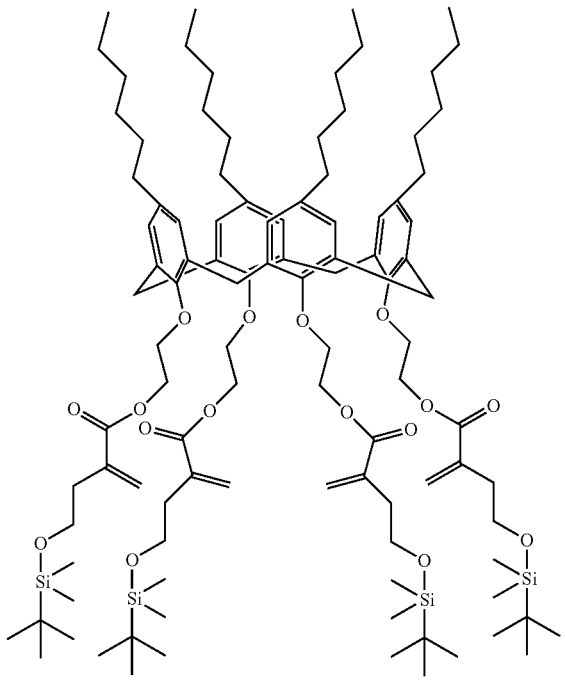

Synthesis Example 35

This example was carried out as in Synthesis Example 34 except that the compound obtained in Synthesis Example 21 was used instead of the compound obtained in Synthesis Example 20. Thus, a compound represented by the formula below was obtained. The compound was in an amount of 1.985 g. The yield was 48.9%.

[Chem. 92]

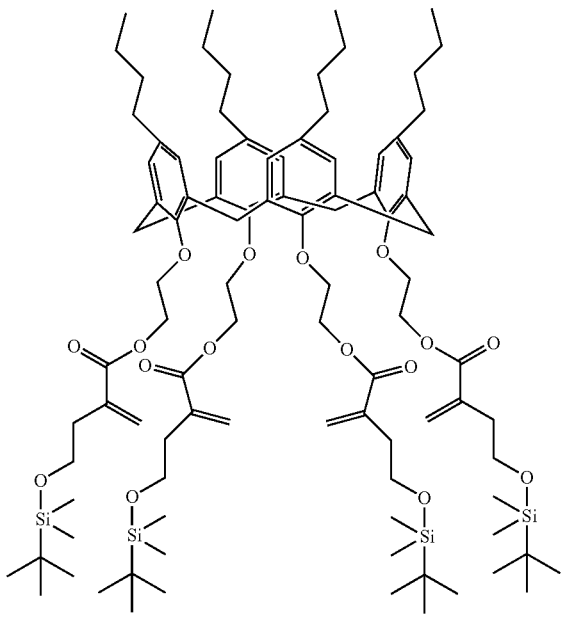

Synthesis Example 36

This example was carried out as in Synthesis Example 34 except that the compound obtained in Synthesis Example 22 was used instead of the compound obtained in Synthesis Example 20. Thus, a compound represented by the formula below was obtained. The compound was in an amount of 2.012 g. The yield was 54.2%.

[Chem. 93]

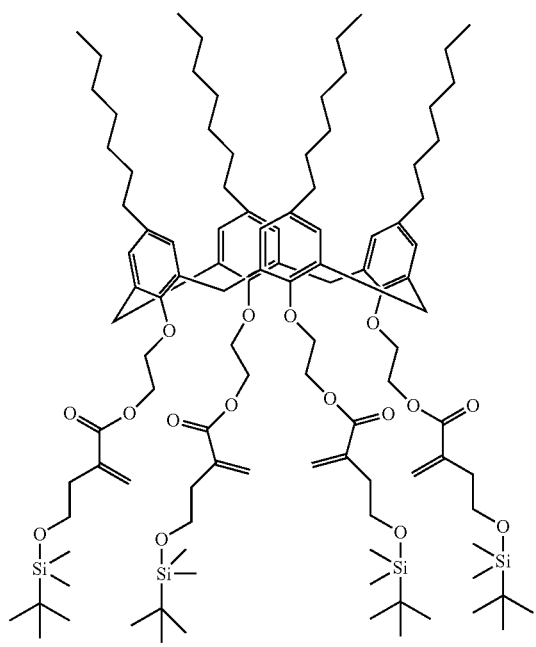

Synthesis Example 37

This example was carried out as in Synthesis Example 34 except that the compound obtained in Synthesis Example 23 was used instead of the compound obtained in Synthesis Example 20. Thus, a compound represented by the formula below was obtained. The compound was in an amount of 1.892 g. The yield was 61.9%.

[Chem. 94]

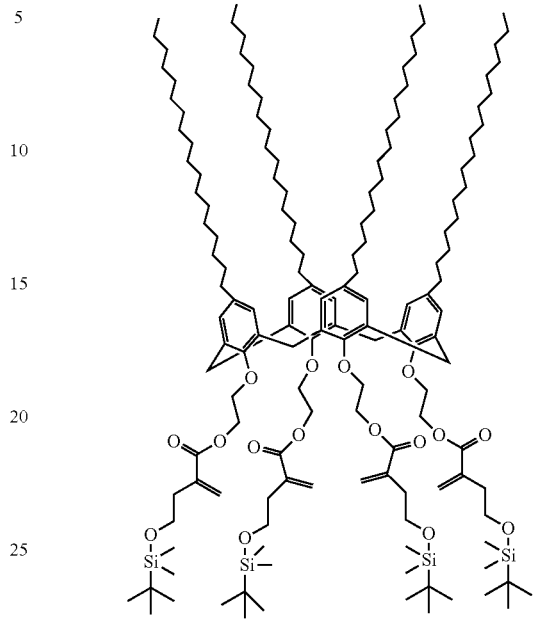

Synthesis Example 38

This example was carried out as in Synthesis Example 34 except that the compound obtained in Synthesis Example 24 was used instead of the compound obtained in Synthesis Example 20. Thus, a compound represented by the formula below was obtained. The compound was in an amount of 2.341 g. The yield was 51.0%.

[Chem. 95]

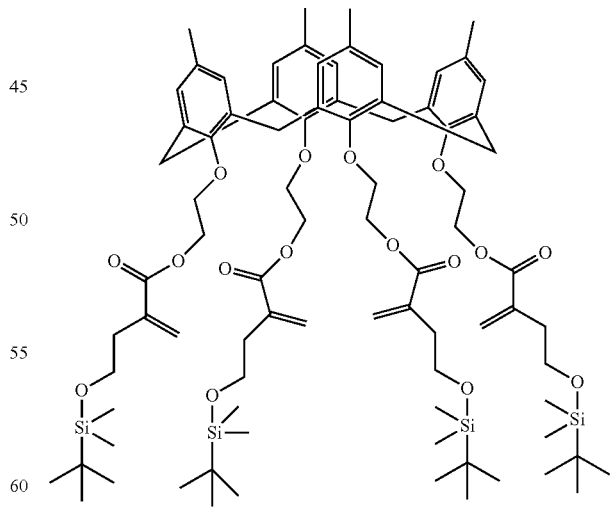

Example 39

This example was carried out as in Example 34 except that the compound obtained in Synthesis Example 34 was used instead of the compound obtained in Synthesis Example 29. Thus, a compound (39-1), represented by the formula below, was obtained. The compound (39-1) was in an amount of 0.452 g. The yield was 60.7%.

[Chem. 96]

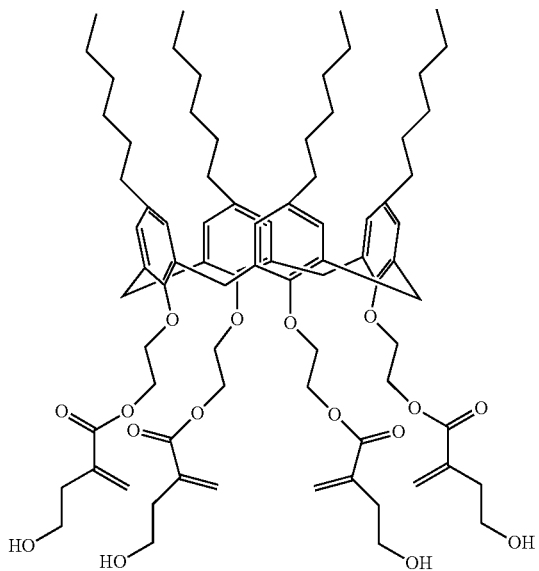

(39-1)

Example 40

This example was carried out as in Example 34 except that the compound obtained in Synthesis Example 35 was used instead of the compound obtained in Synthesis Example 29. Thus, a compound (40-1), represented by the formula below, was obtained. The compound (40-1) was in an amount of 1.103 g. The yield was 61.2%.

[Chem. 97]

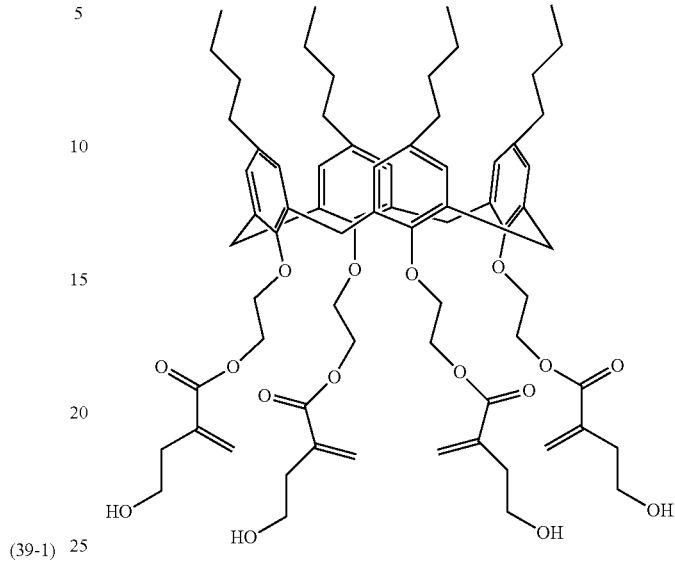

(40-1)

Example 41

This example was carried out as in Example 34 except that the compound obtained in Synthesis Example 36 was used instead of the compound obtained in Synthesis Example 29. Thus, a compound (41-1), represented by the formula below, was obtained. The compound (41-1) was in an amount of 1.013 g. The yield was 67.9%.

[Chem. 98]

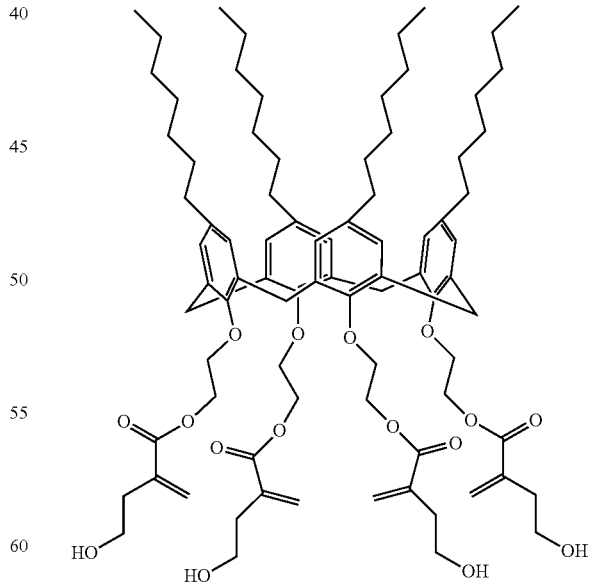

(41-1)

Example 42

This example was carried out as in Example 34 except that the compound obtained in Synthesis Example 37 was used instead of the compound obtained in Synthesis Example 29. Thus, a compound (42-1), represented by the formula below, was obtained. The compound (42-1) was in an amount of 1.004 g. The yield was 65.2%.

[Chem. 99]

(42-1)

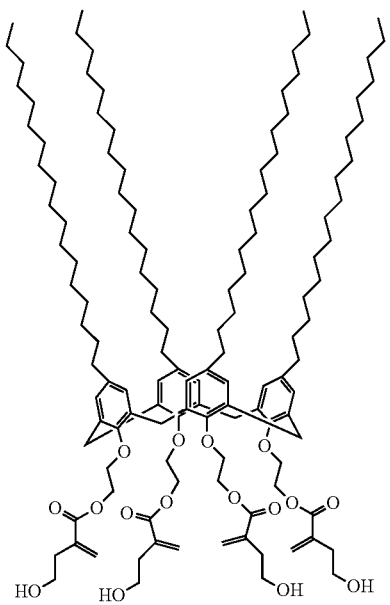

Example 43

This example was carried out as in Example 34 except that the compound obtained in Synthesis Example 38 was used instead of the compound obtained in Synthesis Example 29. Thus, a compound (43-1), represented by the formula below, was obtained. The compound (43-1) was in an amount of 0.871 g. The yield was 53.4%.

[Chem. 100]

(43-1)

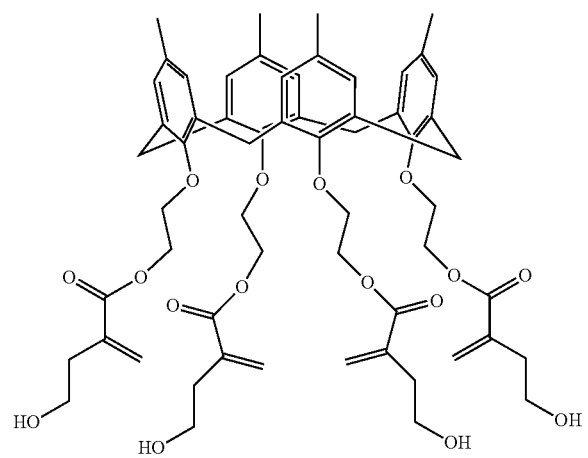

Example 44

In a 100-mL four-neck flask equipped with a stirrer, a thermometer, and a reflux condenser, 2.00 g (1.570 mmol) of G-6, 6.80 g of tetrahydrofuran, 0.905.9 g (3.454 mmol) of triphenylphosphine, and 0.398 g (3.454 mmol) of hydroxyethyl acrylamide were added and stirred. Subsequently, in an ice bath, 0.698 g (3.454 mmol) of diisopropyl azodicarboxylate was added dropwise over 30 minutes. Thereafter, stirring was performed at room temperature for 6 hours to complete the reaction. Hexane was added to the reaction solution to remove by-products, such as triphenylphosphine, by precipitation, and thereafter chloroform extraction was carried out. The extracts were washed with water and saturated brine and subsequently dried with magnesium sulfate. The solvent was evaporated using an evaporator. An orange viscous liquid that was obtained was purified by column chromatography (developing solvent:n-hexane:acetone=90:10). Thus, 54-6, which was a target compound, was obtained. 54-6 was in an amount of 1.014 g. The yield was 50.0%.

[Chem. 101]

(44-1)

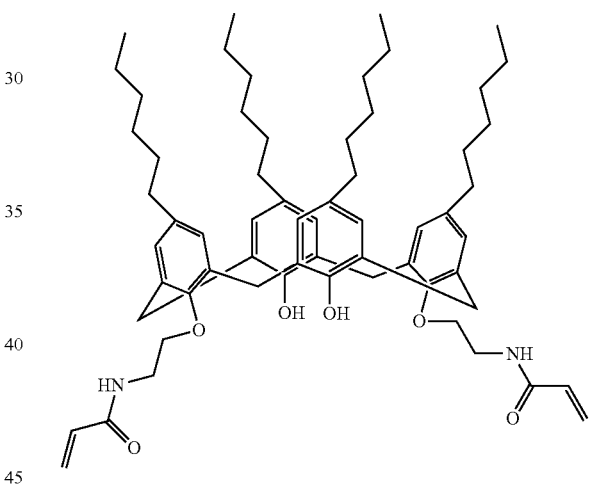

Example 45

In a 50-mL four-neck flask equipped with a stirrer, a thermometer, and a reflux condenser, 2.00 g (1.570 mmol) of the compound obtained in Synthesis Example 10, 6.80 g of tetrahydrofuran, 0.905.9 g (3.454 mmol) of triphenylphosphine, and 0.304 g (3.454 mmol) of hydroxyethyl vinyl ether were added and stirred. Subsequently, in an ice bath, 0.698 g (3.454 mmol) of diisopropyl azodicarboxylate was added dropwise over 30 minutes, and thereafter, stirring was performed at room temperature for 6 hours to complete the reaction. Hexane was added to the reaction solution to remove by-products, such as triphenylphosphine, by precipitation, and thereafter chloroform extraction was carried out. The extracts were washed with water and saturated brine and subsequently dried with magnesium sulfate. The solvent was evaporated using an evaporator. An orange viscous liquid that was obtained was purified by column chromatography (developing solvent:n-hexane:acetone=90:10). Thus, a compound (45-1), represented by the formula below, was obtained. The compound (45-1) was in an amount of 0.756 g. The yield was 38.9%.

[Chem. 102]

(45-1)

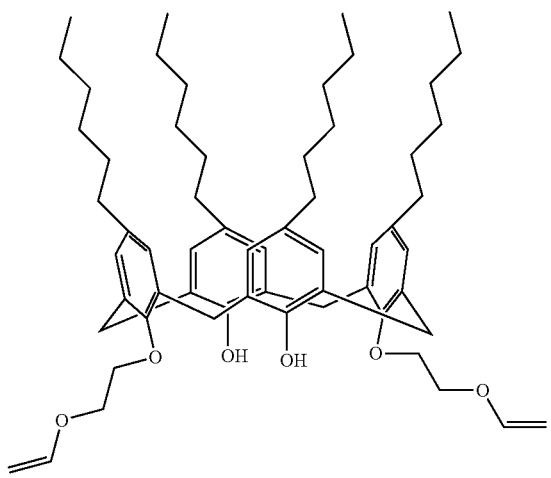

Synthesis Example 39

In a 200-mL four-neck flask equipped with a stirrer, a thermometer, and a reflux condenser, 31.07 g (102.6 mmol) of stearoyl chloride and 49.52 g of nitroethane were added and stirred. Subsequently, 16.96 g (127.2 mmol) of anhydrous aluminum (III) chloride was added in several portions while the flask was cooled in an ice bath. The solution turned to a clear pale orange solution. While stirring was performed at room temperature for 30 minutes, 7.00 g (16.49 mmol) of the intermediate (α-1) obtained in Synthesis Example 1 was added in several portions. The reaction proceeded with foaming, and the solution turned to a clear orange solution. The reaction was allowed to proceed at room temperature for 5 hours. Subsequently, the contents were slowly transferred to a 1-L beaker containing chloroform, ion exchanged water, and ice to terminate the reaction. Subsequently, 1N hydrochloric acid was added to the reaction mixture until a pH of 1 was reached, and thereafter the reaction mixture was transferred to a separatory funnel to separate the organic layer. Next, the aqueous layer was extracted three times with 30 g of chloroform, and the organic layers were combined together. The organic layers were predried with anhydrous magnesium sulfate and then filtered. The solvent was evaporated using an evaporator, and thus a clear yellow solution was obtained. In an ice bath, methanol was added to cause reprecipitation. White crystals that were formed were filtered out with a Kiriyama funnel. Furthermore, the obtained crystals were recrystallized in chloroform and methanol. Thus, a compound represented by the formula below was obtained. The compound was in an amount of 16.20 g. The yield was 65.9%.

[Chem. 103]

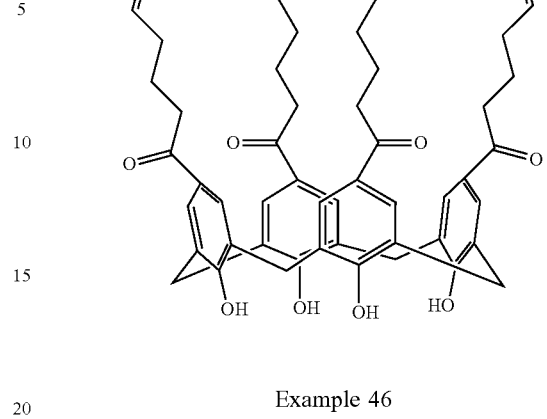

Example 46

This example was carried out as in Example 1 except that the compound obtained in Synthesis Example 39 was used instead of the compound obtained in Synthesis Example 2. Thus, a compound (46-1), represented by the formula below, was obtained. The compound (46-1) was in an amount of 0.2313 g. The yield was 20.5%.

[Chem. 104]

(46-1)

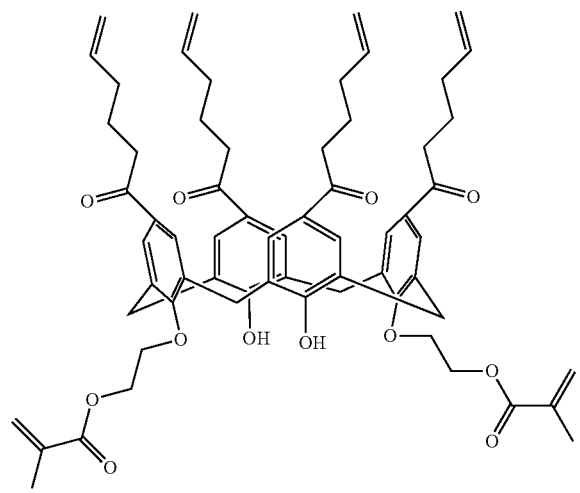

Synthesis Example 40

In a 1-L four-neck flask equipped with a stirrer, a dropping funnel, a thermometer, and a reflux condenser, in a nitrogen atmosphere, sodium hydride (7.54 g, 188.4 mmol) was loaded and washed with hexane to remove mineral oil. Next, dry DMF (160 mL) and hexyl bromide (37.2 g, 207.4 mmol) were added, and the contents were heated to 70° C. with stirring. A solution was added thereto through a dropping funnel. The solution was a solution in which the intermediate (α-1) (10 g, 23.6 mmol) obtained in Synthesis Example 1 was dissolved in dry DMF (80 mL). After completion of addition, stirring was continued for another 2 hours. After being cooled to room temperature, the reaction mixture was added to ice (300 g). Concentrated hydrochloric acid was added thereto to acidify the aqueous solution, which was subsequently extracted twice with chloroform (200 mL). The chloroform solution was washed with water until a pH of 5 or greater was reached. Furthermore, the solution was washed with saturated brine and subsequently dried with anhydrous magnesium sulfate. The solvent was removed using an evaporator, and thus a yellow liquid was obtained. Methanol was added to the mixture with stirring, to cause a solid to precipitate out. The solid was filtered out and recrystallized in isopropyl alcohol. White crystals that were obtained were dried under vacuum. Thus, a compound represented by the formula below was obtained (11.6 g, 65% yield).

[Chem. 105]

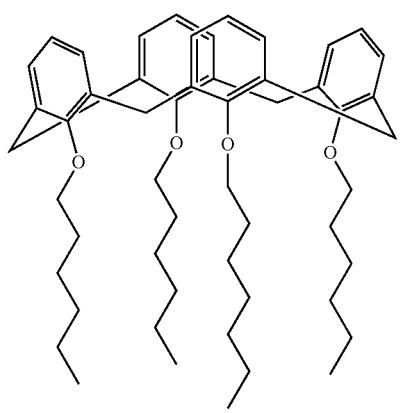

Synthesis Example 41

This example was carried out as in Synthesis Example 40 except that methyl iodide was used instead of hexyl bromide, and the reaction was carried out at room temperature for 24 hours. Thus, a compound represented by the formula below was obtained (6.8 g, 60% yield).

[Chem. 106]

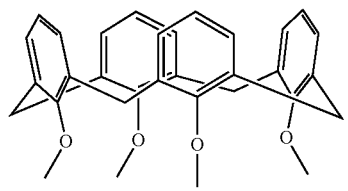

Synthesis Example 42

This example was carried out as in Synthesis Example 40 except that butyl bromide was used instead of hexyl bromide. Thus, a compound represented by the formula below was obtained (11.0 g, 72% yield).

[Chem. 107]

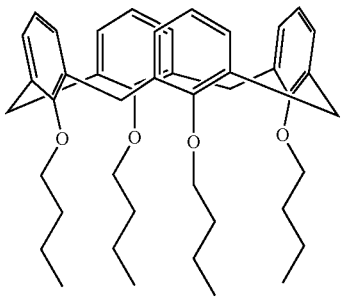

Synthesis Example 43

This example was carried out as in Synthesis Example 40 except that heptyl bromide was used instead of hexyl bromide. Thus, a compound represented by the formula below was obtained (14.4 g, 75% yield).

[Chem. 108]

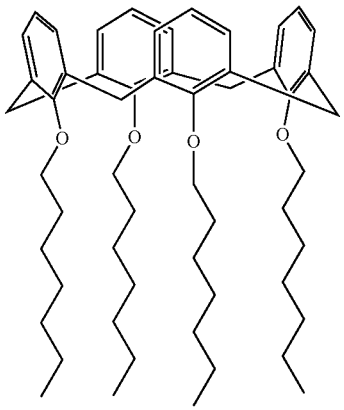

Synthesis Example 44

This example was carried out as in Synthesis Example 40 except that octadecyl bromide was used instead of hexyl bromide. Thus, a compound represented by the formula below was obtained (23.6 g, 70% yield).

[Chem. 109]

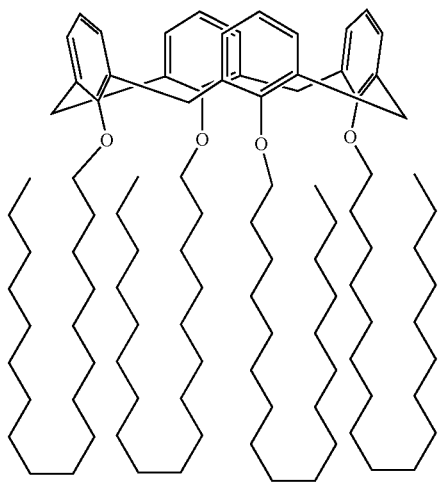

Synthesis Example 45

By referring to a publication (Organic & Biomolecular Chemistry, 13, 1708 to 1723; 2015), a compound represented by the formula below was synthesized in two steps (in an amount of 3.3 g, 67% yield) by using the compound obtained in Synthesis Example 40 (5.0 g, 6.57 mmol).

[Chem. 110]

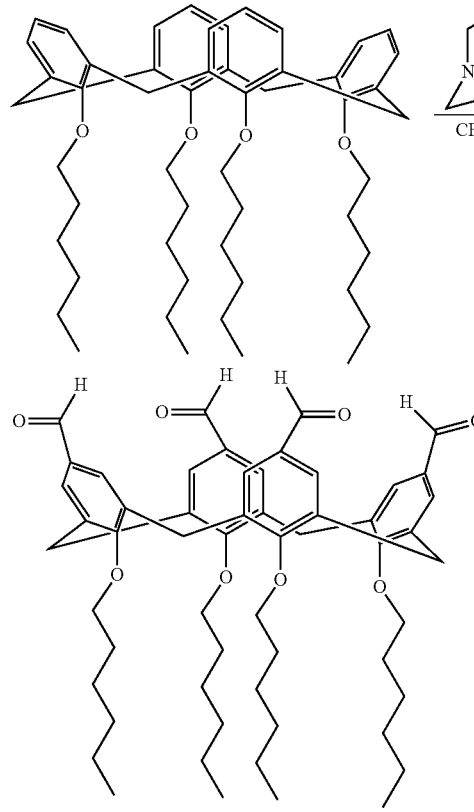

Synthesis Example 46

This example was carried out as in Synthesis Example 45 except that the compound obtained in Synthesis Example 41 (5.0 g, 10.4 mmol) was used instead of the compound obtained in Synthesis Example 40. Thus, a compound represented by the formula below was synthesized in two steps (3.75 g, 60% yield).

[Chem. 111]

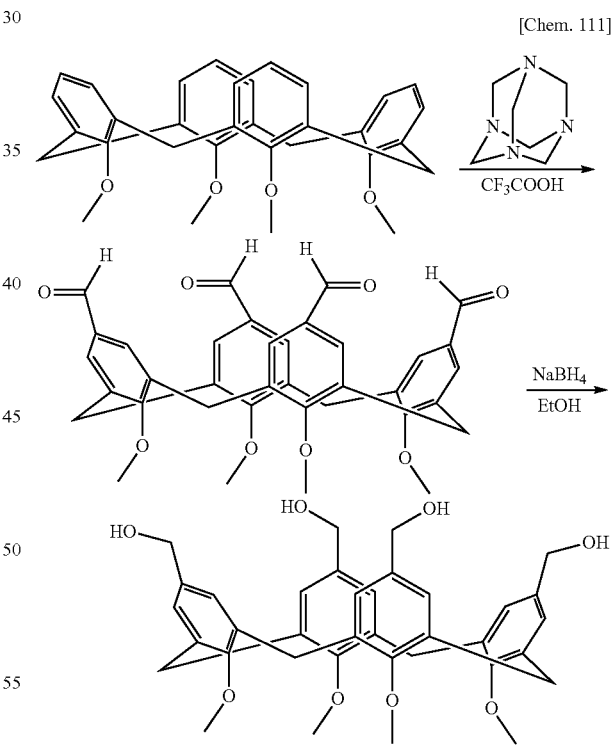

Synthesis Example 47

This example was carried out as in Synthesis Example 45 except that the compound obtained in Synthesis Example 42 (5.0 g, 7.7 mmol) was used instead of the compound obtained in Synthesis Example 40. Thus, a compound represented by the formula below was synthesized in two steps (3.73 g, 63% yield).

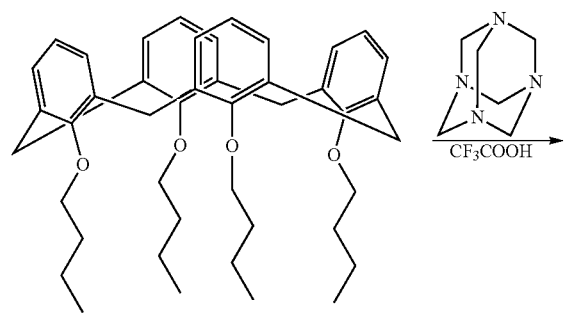
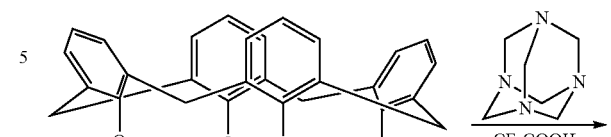
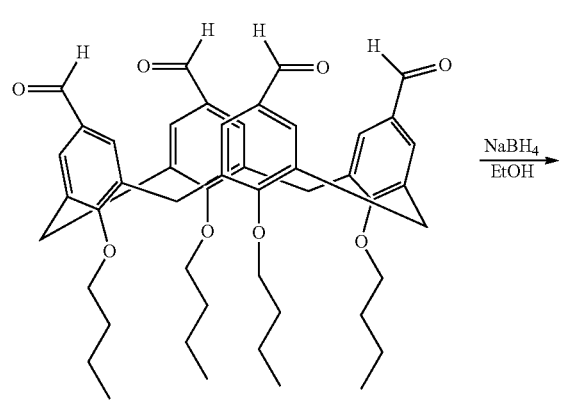
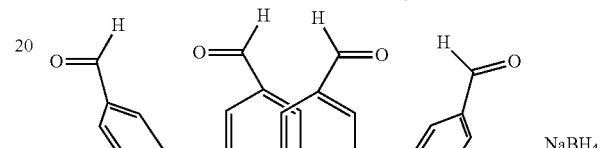
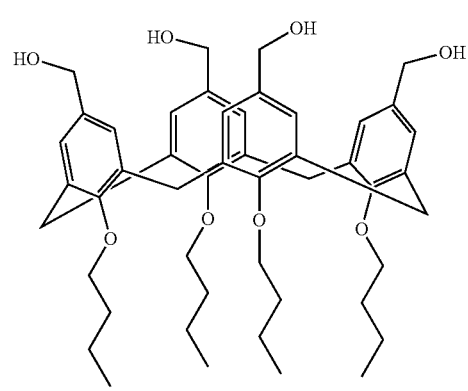
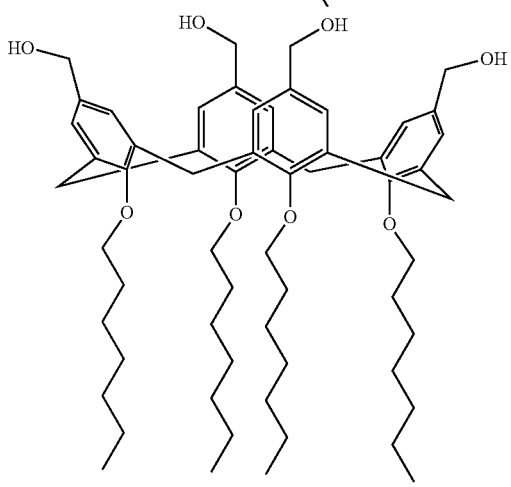

Synthesis Example 48

This example was carried out as in Synthesis Example 45 except that the compound obtained in Synthesis Example 43 (5.0 g, 6.1 mmol) was used instead of the compound obtained in Synthesis Example 40. Thus, a compound represented by the formula below was synthesized in two steps (4.01 g, 70% yield).

Synthesis Example 49

This example was carried out as in Synthesis Example 45 except that the compound obtained in Synthesis Example 44 (10.0 g, 7.0 mmol) was used instead of the compound obtained in Synthesis Example 40. Thus, a compound represented by the formula below was synthesized in two steps (5.96 g, 55% yield).

[Chem. 114]

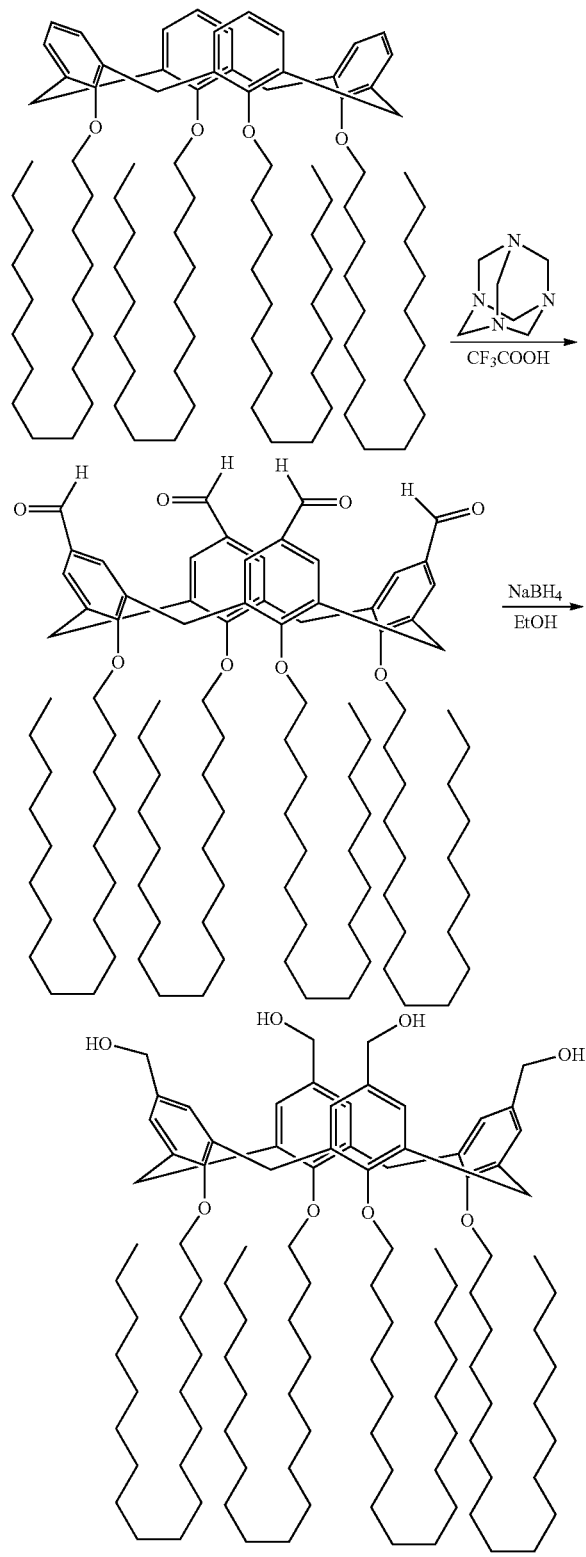

Synthesis Example 50

In a 500-mL four-neck flask equipped with a stirrer, a dropping funnel, a thermometer, and a reflux condenser, in a nitrogen atmosphere, sodium hydride (3.28 g, 82.1 mmol) was loaded and washed with hexane to remove mineral oil. Next, dry DMF (100 mL) and hexyl bromide (16.2 g, 90.3 mmol) were added, and the contents were heated to 70° C. with stirring. A solution was added thereto through a dropping funnel. The solution was a solution in which 5,11,17,23-tetraallyl-25,26,27,28-tetrahydroxycalix[4]arene (6.0 g, 10.3 mmol), which had been synthesized by using a method described in a publication (The Journal of Organic Chemistry 50, 5802 to 58061; 1985), was dissolved in dry DMF (40 mL). After completion of addition, stirring was continued for another 2 hours. After being cooled to room temperature, the reaction mixture was added to ice (200 g). Concentrated hydrochloric acid was added thereto to acidify the aqueous solution, which was subsequently extracted twice with chloroform (150 mL). The chloroform solution was washed with water until a pH of 5 or greater was reached. Furthermore, the solution was washed with saturated brine and subsequently dried with anhydrous magnesium sulfate. The solvent was removed using an evaporator, and thus a yellow liquid was obtained. The yellow liquid was purified by silica gel column chromatography, and thus a clear colorless liquid was obtained. Subsequently, recrystallization was carried out, and thus a compound represented by the formula below, which was a white solid, was obtained (6.6 g, 70% yield).

[Chem. 115]

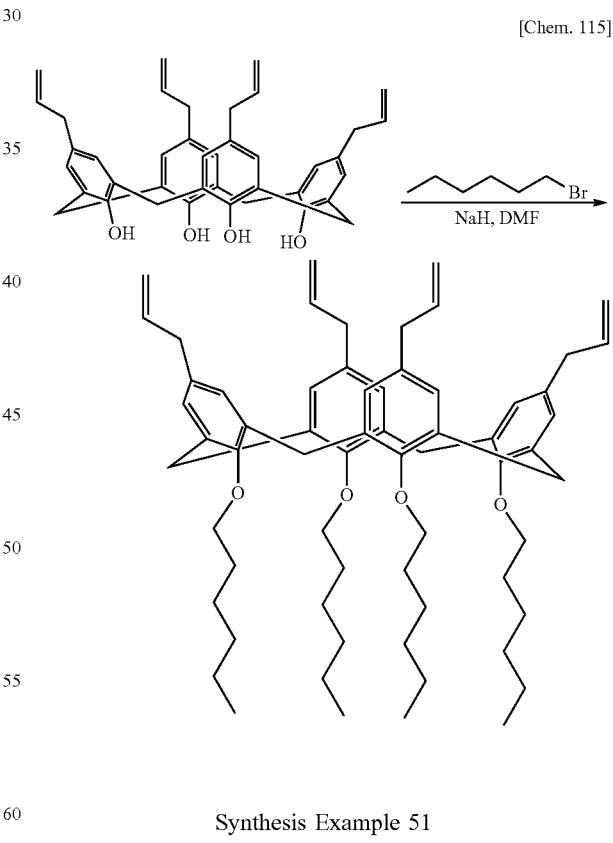

Synthesis Example 51

This example was carried out as in Synthesis Example 50 except that methyl iodide was used instead of hexyl bromide, and the reaction was carried out at room temperature for 24 hours. Thus, a compound represented by the formula below was obtained (4.27 g, 65% yield).

[Chem. 116]

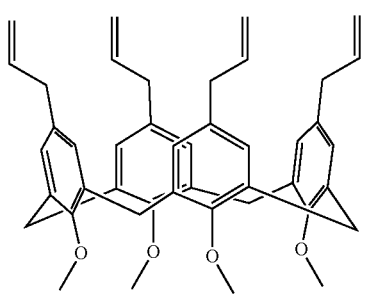

Synthesis Example 52

This example was carried out as in Synthesis Example 50 except that butyl bromide was used instead of hexyl bromide. Thus, a compound represented by the formula below was obtained (6.23 g, 75% yield).

[Chem. 117]

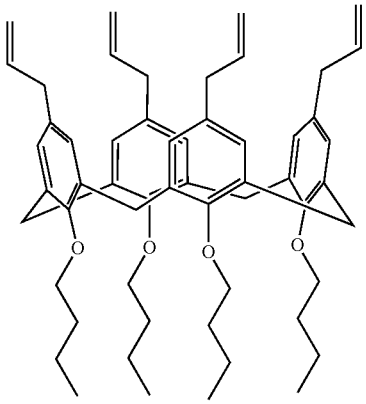

Synthesis Example 53

This example was carried out as in Synthesis Example 50 except that heptyl bromide was used instead of hexyl bromide. Thus, a compound represented by the formula below was obtained (8.02 g, 80% yield).

[Chem. 118]

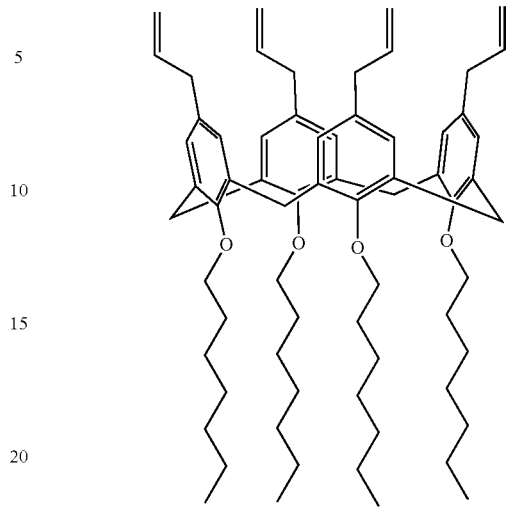

Synthesis Example 54

This example was carried out as in Synthesis Example 50 except that octadecyl bromide was used instead of hexyl bromide. Thus, a compound represented by the formula below was obtained (12.8 g, 75% yield).

[Chem. 119]

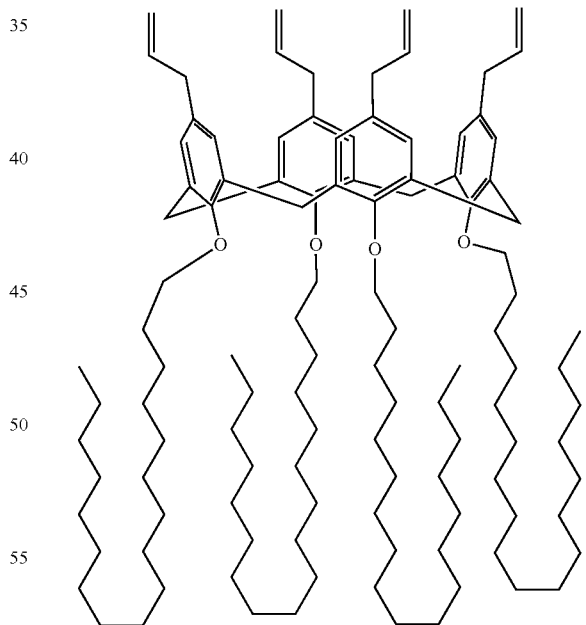

Synthesis Example 55

By referring to a publication (The Journal of Organic Chemistry, 67, 4722 to 4733; 2002), a compound represented by the formula below was synthesized (in an amount of 2.93 g, 68% yield) by using the compound obtained in Synthesis Example 50 (4 g, 4.34 mmol).

[Chem. 120]

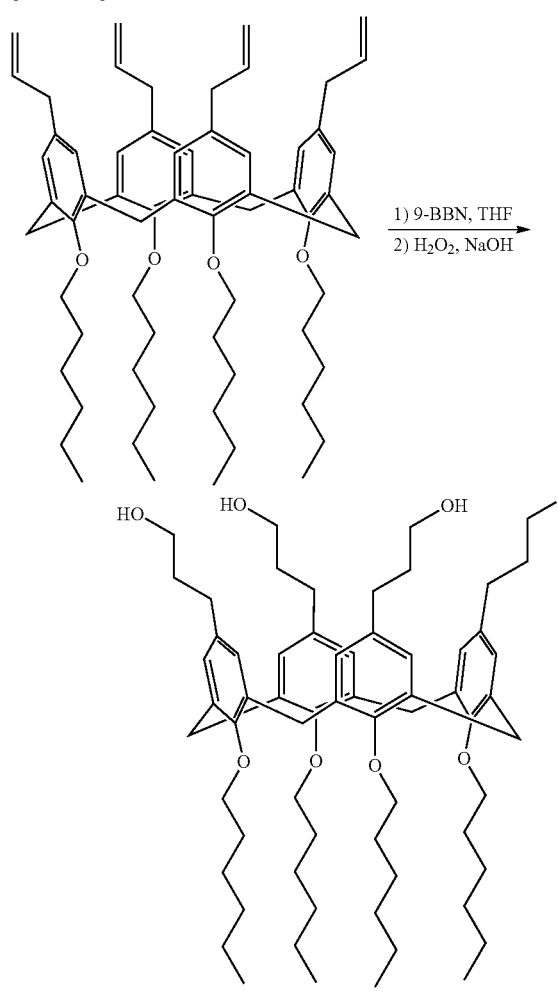

Synthesis Example 56

This example was carried out as in Synthesis Example 55 except that the compound obtained in Synthesis Example 51 (4.0 g, 6.24 mmol) was used instead of the compound obtained in Synthesis Example 50. Thus, a compound represented by the formula below was obtained (4.5 g, 72% yield).

[Chem. 121]

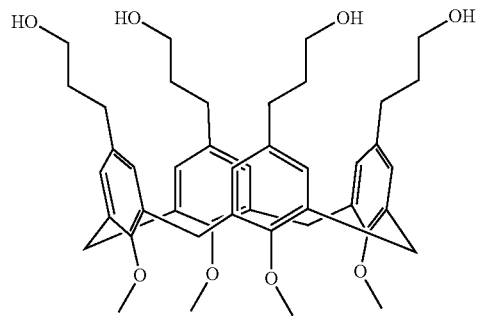

Synthesis Example 57

This example was carried out as in Synthesis Example 55 except that the compound obtained in Synthesis Example 52 (4.0 g, 4.94 mmol) was used instead of the compound obtained in Synthesis Example 50. Thus, a compound represented by the formula below was obtained (2.59 g, 65% yield).

[Chem. 122]

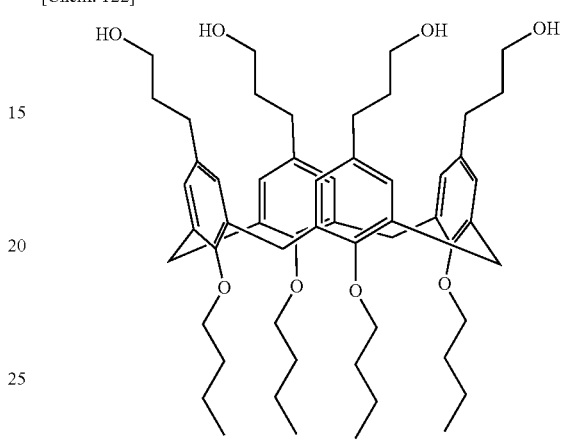

Synthesis Example 58

This example was carried out as in Synthesis Example 55 except that the compound obtained in Synthesis Example 53 (4.0 g, 4.11 mmol) was used instead of the compound obtained in Synthesis Example 50. Thus, a compound represented by the formula below was obtained (3.23 g, 75% yield).

[Chem. 123]

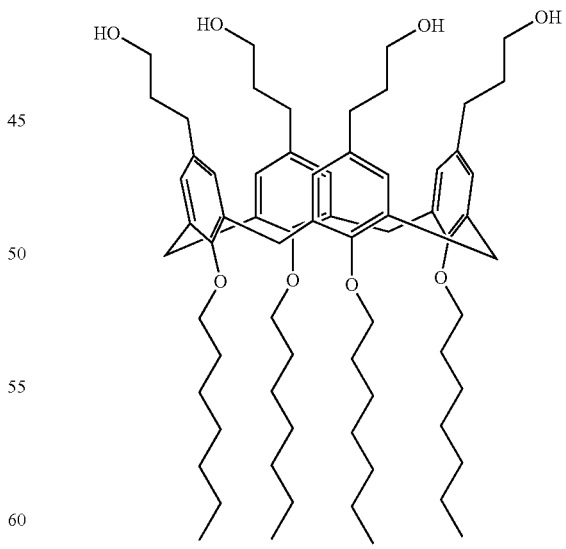

Synthesis Example 59

This example was carried out as in Synthesis Example 55 except that the compound obtained in Synthesis Example 54

(8.0 g, 5.02 mmol) was used instead of the compound obtained in Synthesis Example 50. Thus, a compound represented by the formula below was obtained (5.1 g, 61% yield).

[Chem. 124]

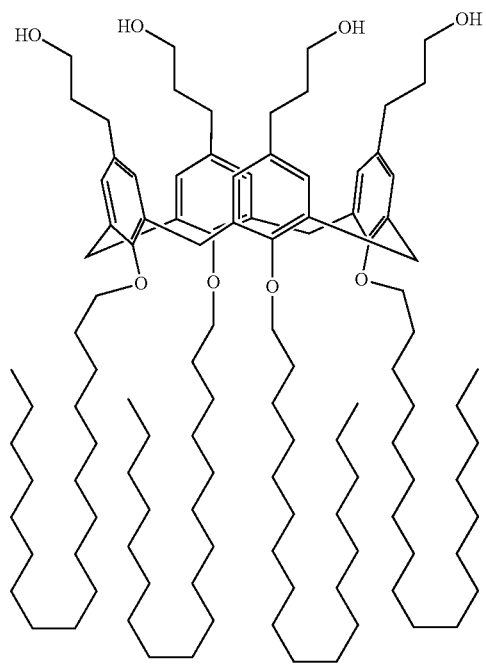

Example 47

In a 100-mL four-neck flask equipped with a stirrer, a dropping funnel, and a thermometer, in a nitrogen atmosphere, the compound obtained in Synthesis Example 45 (3 g, 3.94 mmol), triethylamine (2.39 g, 23.6 mmol), and methylene chloride (27 mL) were loaded and stirred under ice cooling. Acryloyl chloride (0.89 g, 9.85 mmol) was slowly added dropwise by syringe. After completion of dropwise addition, stirring was performed at room temperature for 8 hours. Water was added to the reaction mixture, which was then extracted twice with chloroform (50 mL). The chloroform solution was washed with dilute hydrochloric acid, a saturated aqueous sodium bicarbonate solution, and saturated brine and was subsequently dried with anhydrous magnesium sulfate. The solvent was removed using an evaporator, and thus a yellow liquid was obtained. The yellow liquid was purified by silica gel column chromatography. Thus, compounds represented by the formulae below were obtained: a compound (47-1) in an amount of 0.376 g (10.2% yield); a mixture of compounds (47-2) and (47-3) in an amount of 2.14 g (55% yield); and a compound (47-4) in an amount of 0.547 g (13.3% yield).

[Chem. 125]

(47-1)

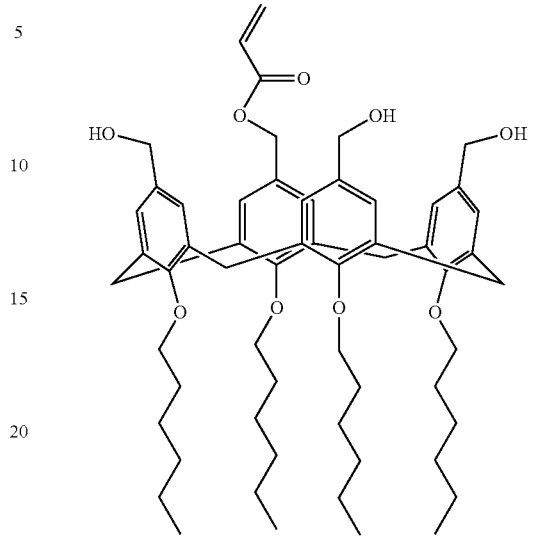

(47-2)

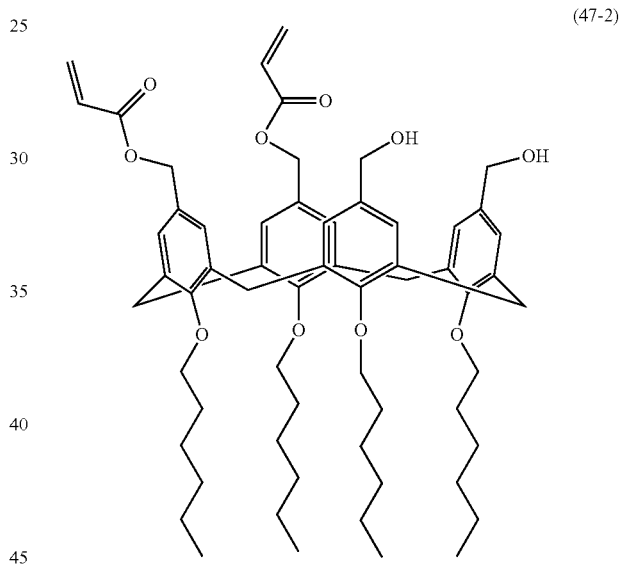

(47-3)

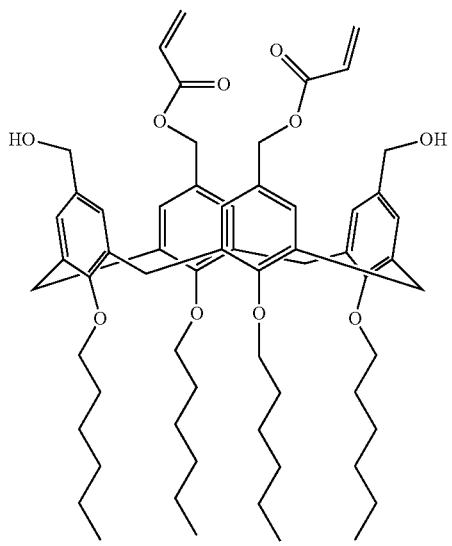

(47-4)

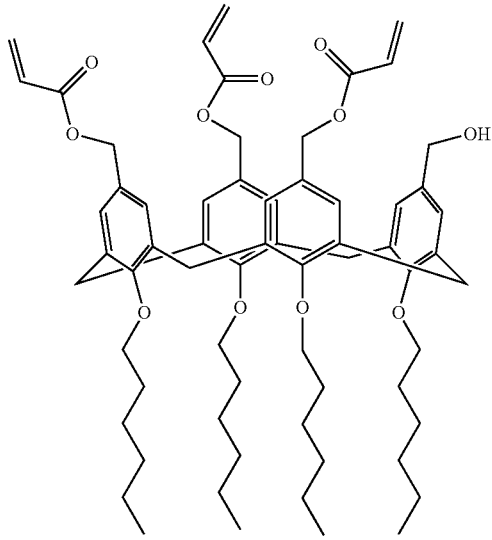

Example 48

This example was carried out as in Example 47 except that the compound obtained in Synthesis Example 46 (3 g, 4.99 mmol) was used instead of the compound obtained in Synthesis Example 45. Thus, compounds represented by the formulae below were obtained: a compound (48-1) in an amount of 0.376 g (11.5% yield); a mixture of compounds (48-2) and (48-3) in an amount of 1.88 g (53.1% yield); and a compound (48-4) in an amount of 0.362 g (9.5% yield).

[Chem. 126]

(48-1)

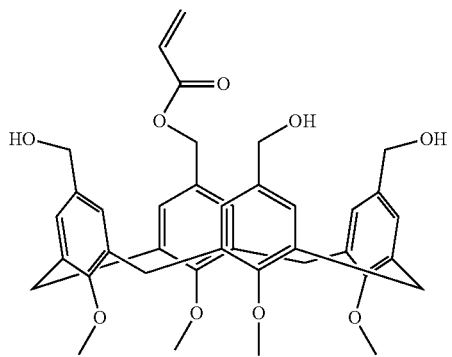

(48-2)

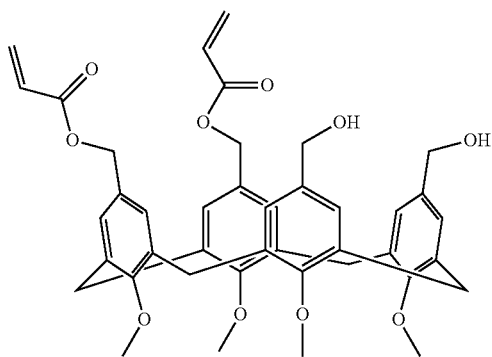

(48-3)

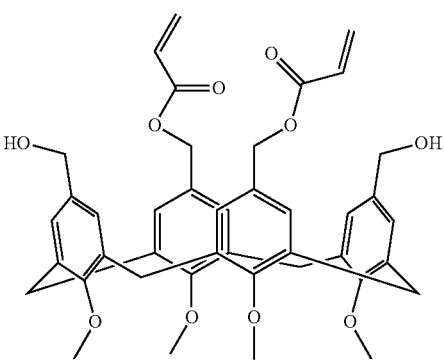

(48-4)

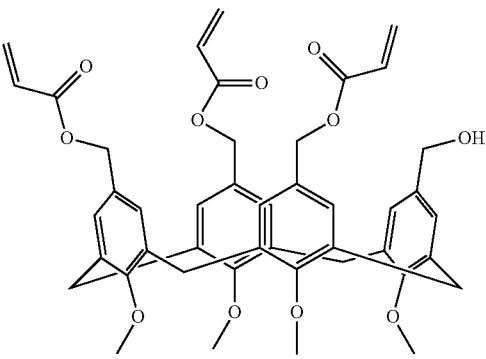

Example 49

This example was carried out as in Example 47 except that the compound obtained in Synthesis Example 47 (3.0 g, 3.9 mmol) was used instead of the compound obtained in Synthesis Example 45. Thus, compounds represented by the formulae below were obtained: a compound (49-1) in an amount of 0.453 g (14.1% yield); a mixture of compounds (49-2) and (49-3) in an amount of 1.77 g (51.8% yield); and a compound (49-4) in an amount of 0.418 g (11.5% yield).

[Chem. 127]

(49-1)

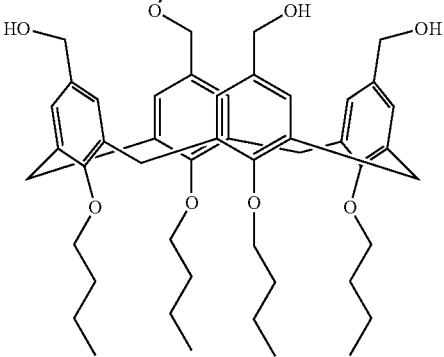

(49-2)

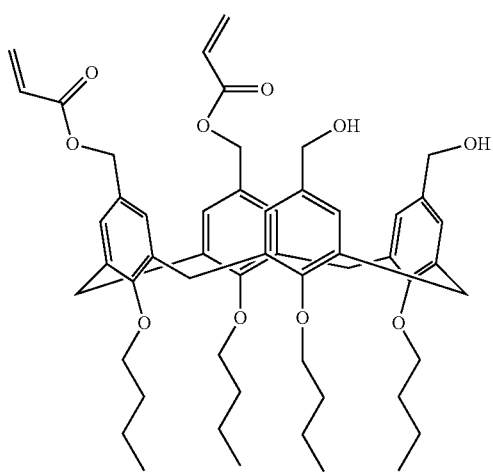

(49-3)

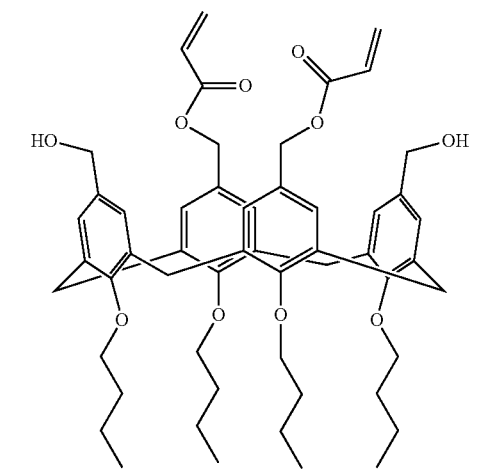

(49-4)

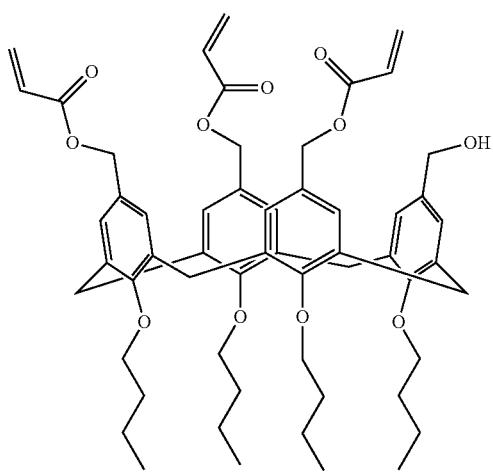

Example 50

This example was carried out as in Example 47 except that the compound obtained in Synthesis Example 48 (3.0 g, 3.2 mmol) was used instead of the compound obtained in Synthesis Example 45. Thus, compounds represented by the formulae below were obtained: a compound (50-1) in an amount of 0.41 g (12.8% yield); a mixture of compounds (50-2) and (50-3) in an amount of 1.93 g (57.6% yield); and a compound (50-4) in an amount of 0.37 g (10.5% yield).

[Chem. 128]

(50-1)

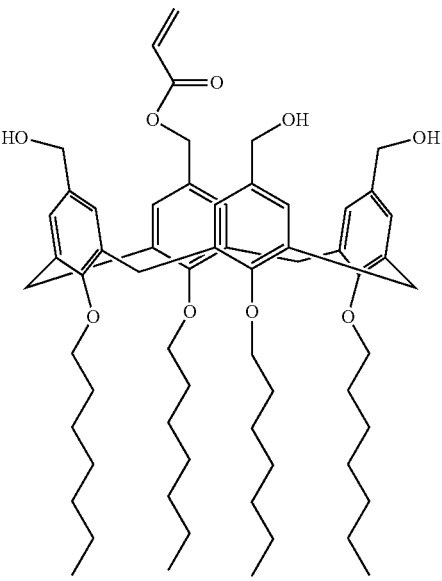

(50-2)

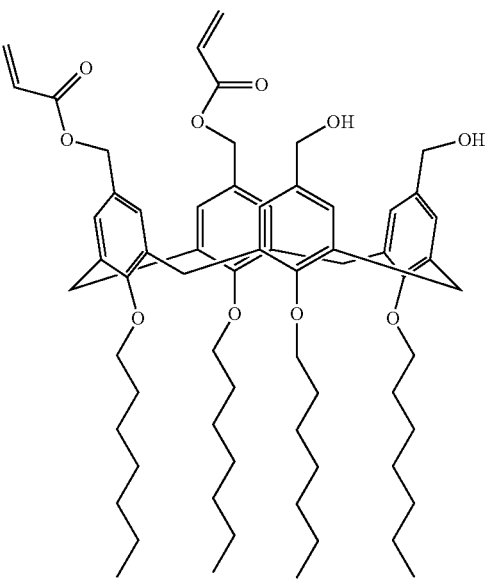

(50-3)

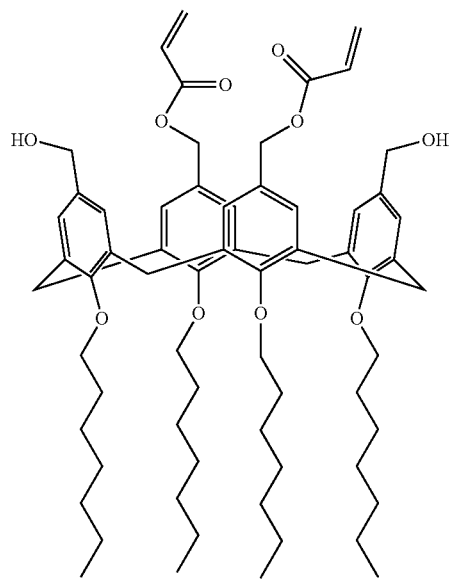

[Chem. 129]

(51-1)

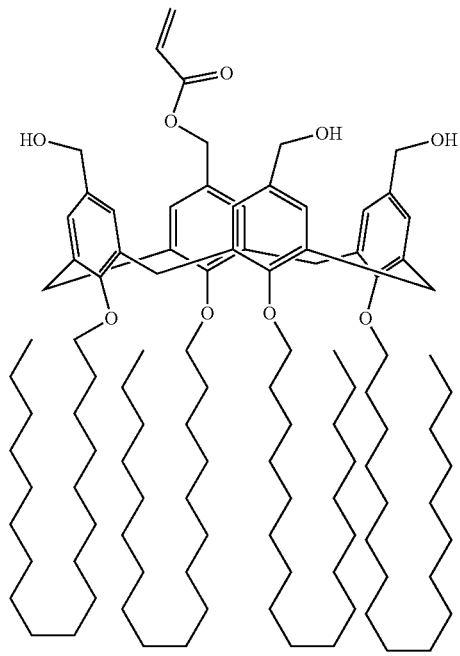

(50-4)

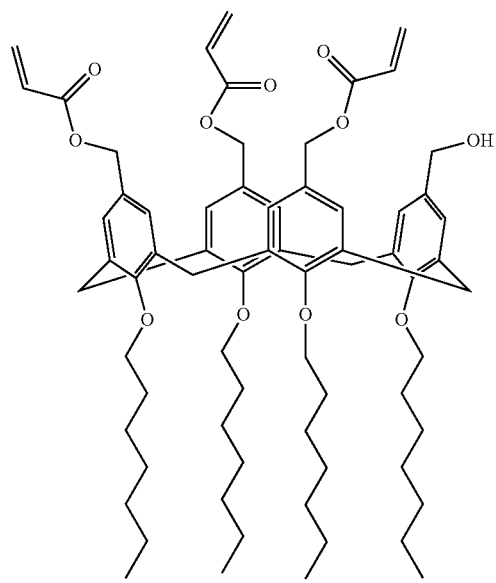

Example 51

This example was carried out as in Example 47 except that the compound obtained in Synthesis Example 49 (3.0 g, 1.93 mmol) was used instead of the compound obtained in Synthesis Example 45. Thus, compounds represented by the formulae below were obtained: a compound (51-1) in an amount of 0.35 g (11.3% yield); a mixture of compounds (51-2) and (51-3) in an amount of 1.81 g (56.3% yield); and a compound (51-4) in an amount of 0.41 g (12.5% yield).

(51-2)

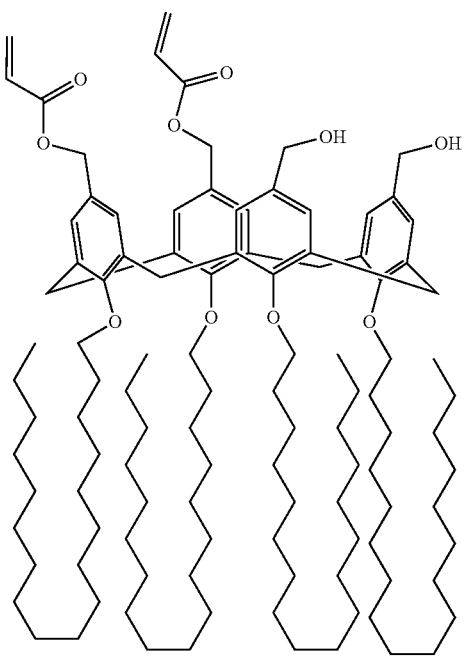

(51-3)

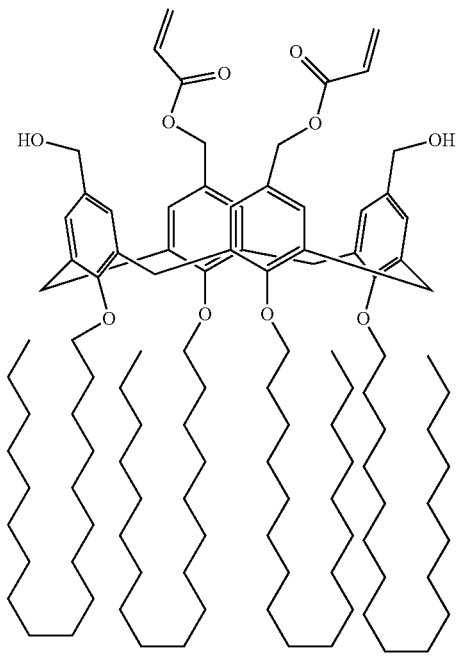

(51-4)

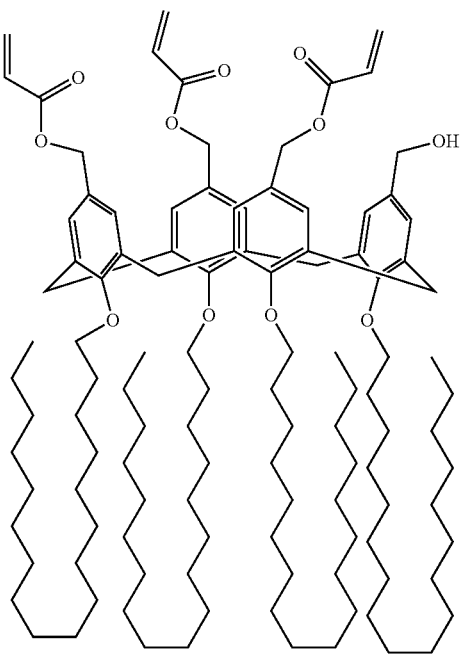

Synthesis Example 60

In a 100-mL four-neck flask equipped with a stirrer, a thermometer, and a reflux condenser, 2.00 g (2.27 mmol) of the compound obtained in Synthesis Example 45, 3.57 g (13.62 mmol) of triphenylphosphine, 2.95 g (13.62 mmol) of 2-[[[1,1-dimethylethyl)dimethylsilyl]oxy]-2-propenoic acid, and 38 mL of tetrahydrofuran were added and stirred. Next, in an ice bath, 2.75 g (13.62 mmol) of diisopropyl azodicarboxylate was added dropwise over 30 minutes, and stirring was performed at room temperature for another 12 hours. The reaction solution was concentrated using an evaporator. Hexane was added to remove by-products, such as triphenylphosphine, by precipitation. A yellow viscous liquid that was obtained was purified by silica gel column chromatography. Thus, a compound represented by the formula below, which was a pale yellow solid, was obtained (in an amount of 2.85 g, 75.0% yield).

[Chem. 130]

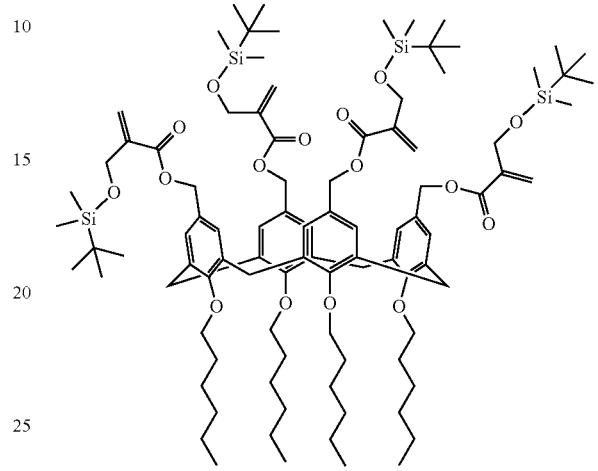

Synthesis Example 61

This example was carried out as in Synthesis Example 60 except that the compound obtained in Synthesis Example 46 (2.00 g, 3.33 mmol) was used instead of the compound obtained in Synthesis Example 45. Thus, a compound represented by the formula below was obtained (3.26 g, 70.2% yield).

[Chem. 131]

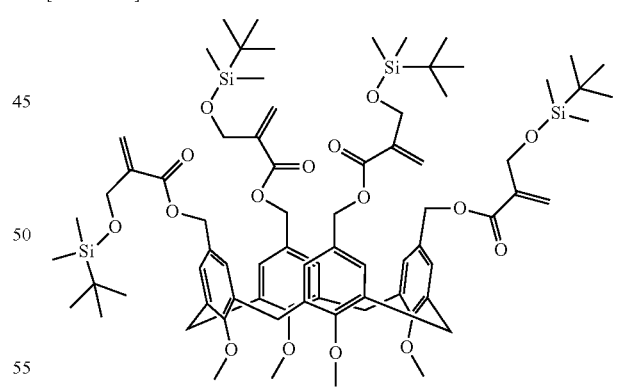

Synthesis Example 62

This example was carried out as in Synthesis Example 60 except that the compound obtained in Synthesis Example 47 (2.00 g, 2.60 mmol) was used instead of the compound obtained in Synthesis Example 45. Thus, a compound represented by the formula below was obtained (3.12 g, 76.8% yield).

[Chem. 132]

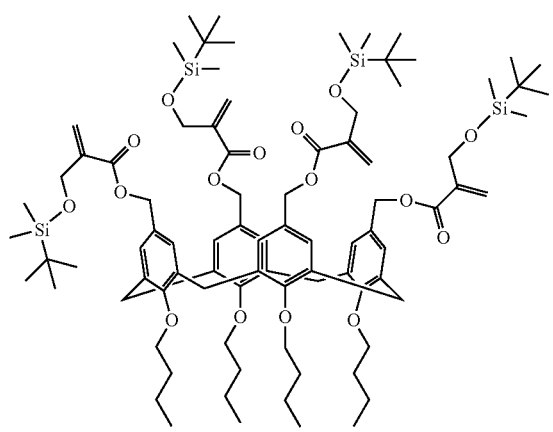

Synthesis Example 63

This example was carried out as in Synthesis Example 60 except that the compound obtained in Synthesis Example 48 (2.00 g, 2.13 mmol) was used instead of the compound obtained in Synthesis Example 45. Thus, a compound represented by the formula below was obtained (2.74 g, 74.2% yield).

[Chem. 133]

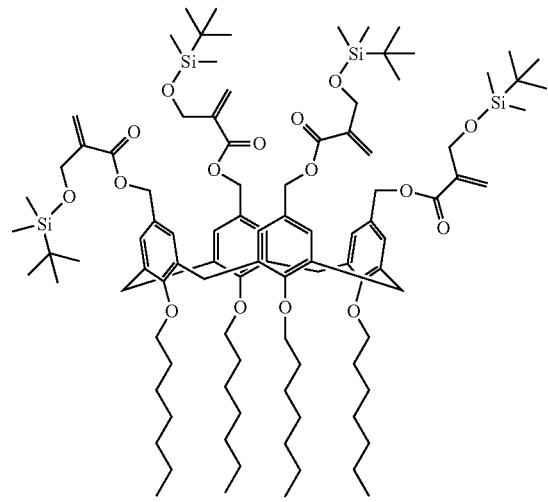

Synthesis Example 64

This example was carried out as in Synthesis Example 60 except that the compound obtained in Synthesis Example 49 (2.00 g, 1.29 mmol) was used instead of the compound obtained in Synthesis Example 45. Thus, a compound represented by the formula below was obtained (2.58 g, 85.3% yield).

[Chem. 134]

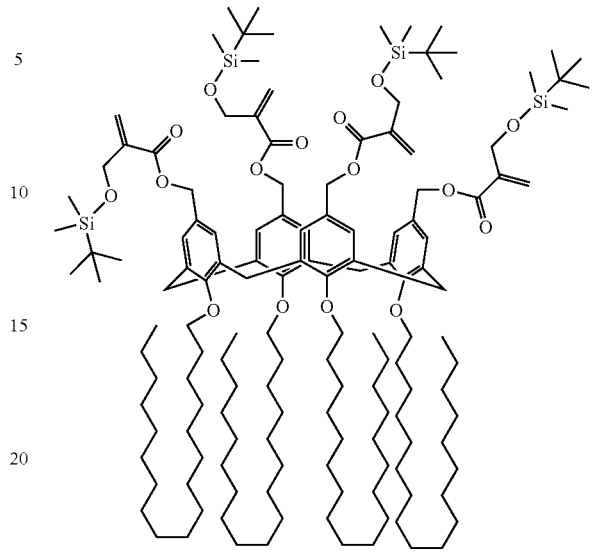

Example 52

In a 100-mL four-neck flask equipped with a stirrer, a thermometer, and a reflux condenser, 1.80 g (1.07 mmol) of the compound obtained in Synthesis Example 60, 0.387 g (6.45 mmol) of acetic acid, and 43 mL of tetrahydrofuran were added and stirred. A clear colorless solution. Subsequently, in an ice bath, 6.45 mL (6.45 mmol) of tetrabutylammonium fluoride (ca. 1 mol/L in tetrahydrofuran) was slowly added dropwise with stirring. Stirring was performed at room temperature for 12 hours. A saturated aqueous ammonium chloride solution was added to the reaction mixture, and then 30 mL of chloroform was added. The reaction mixture was transferred to a separatory funnel to separate the organic layer, and further, the aqueous layer was extracted twice with 30 mL of chloroform. The combined organic layers were washed with saturated brine and subsequently dried with anhydrous magnesium sulfate. The solvent was evaporated using an evaporator, and thus a clear yellow liquid was obtained. The liquid was purified by silica gel column column chromatography. Thus, a compound (52-1), represented by the formula below, which was a white solid, was obtained (1.21 g, 92.3% yield).

[Chem. 135]

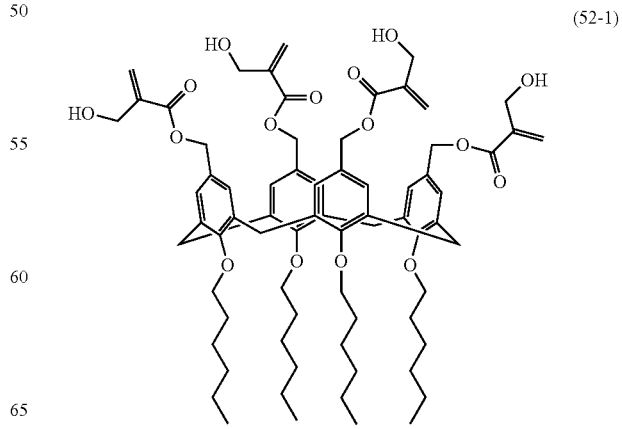

(52-1)

Example 53

This example was carried out as in Example 52 except that the compound obtained in Synthesis Example 61 (1.8 g, 1.29 mmol) was used instead of the compound obtained in Synthesis Example 60. Thus, a compound (53-1), represented by the formula below, was obtained (1.10 g, 90.5% yield).

[Chem. 136]

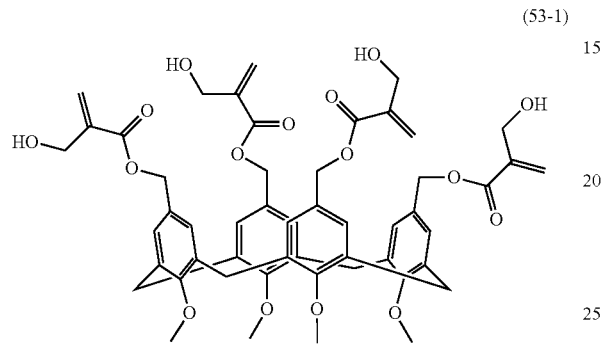

(53-1)

Example 54

This example was carried out as in Example 52 except that the compound obtained in Synthesis Example 62 (1.8 g, 1.15 mmol) was used instead of the compound obtained in Synthesis Example 60. Thus, a compound (54-1), represented by the formula below, was obtained (1.19 g, 93.4% yield).

[Chem. 137]

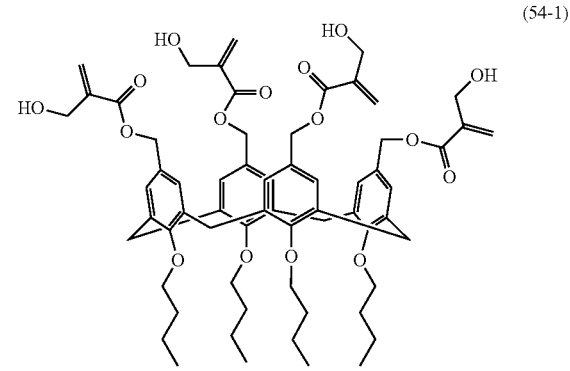

(54-1)

Example 55

This example was carried out as in Example 52 except that the compound obtained in Synthesis Example 63 (1.8 g, 1.04 mmol) was used instead of the compound obtained in Synthesis Example 60. Thus, a compound (55-1), represented by the formula below, was obtained (1.26 g, 95.2% yield).

[Chem. 138]

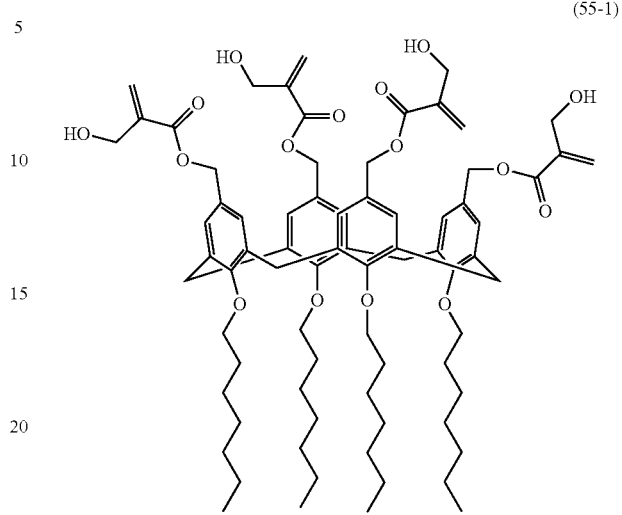

(55-1)

Example 56

This example was carried out as in Example 52 except that the compound obtained in Synthesis Example 64 (2.0 g, 0.85 mmol) was used instead of the compound obtained in Synthesis Example 60. Thus, a compound (56-1), represented by the formula below, was obtained (1.51 g, 93.5% yield).

[Chem. 139]

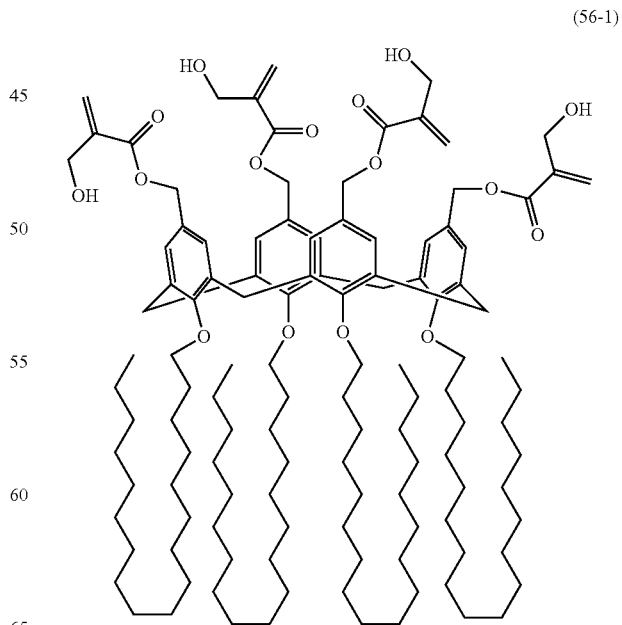

(56-1)

Example 57

In a 100-mL four-neck flask equipped with a stirrer, a dropping funnel, and a thermometer, in a nitrogen atmosphere, the compound obtained in Synthesis Example 55 (3.50 g, 3.52 mmol), triethylamine (2.14 g, 21.4 mmol), and methylene chloride (27.4 mL) were loaded and stirred under ice cooling. Acryloyl chloride (0.80 g, 8.81 mmol) was slowly added dropwise by syringe. After completion of dropwise addition, stirring was performed at room temperature for 8 hours. Water was added to the reaction mixture, which was then extracted twice with chloroform (50 mL). The chloroform solution was washed with dilute hydrochloric acid, a saturated aqueous sodium bicarbonate solution, and saturated brine and was subsequently dried with anhydrous magnesium sulfate. The solvent was removed using an evaporator, and thus a yellow liquid was obtained. The yellow liquid was purified by silica gel column chromatography. Thus, compounds represented by the formulae below were obtained: a compound (57-1) in an amount of 0.328 g (8.9% yield); a mixture of compounds (57-2) and (57-3) in an amount of 2.25 g (58.0% yield); and a compound (57-4) in an amount of 0.415 g (10.2% yield).

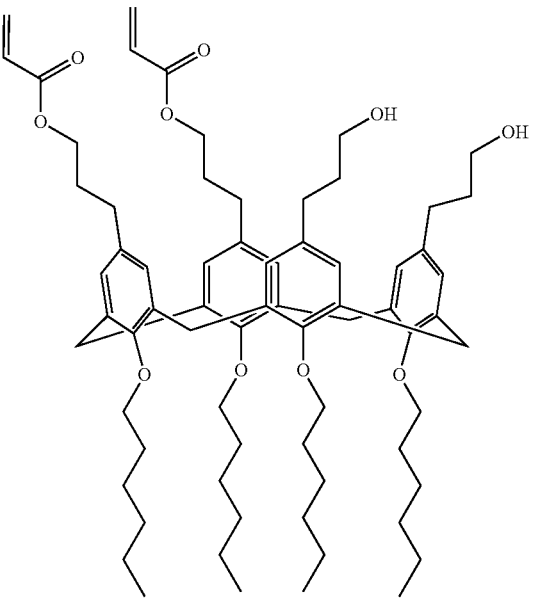

(57-2)

[Chem. 140]

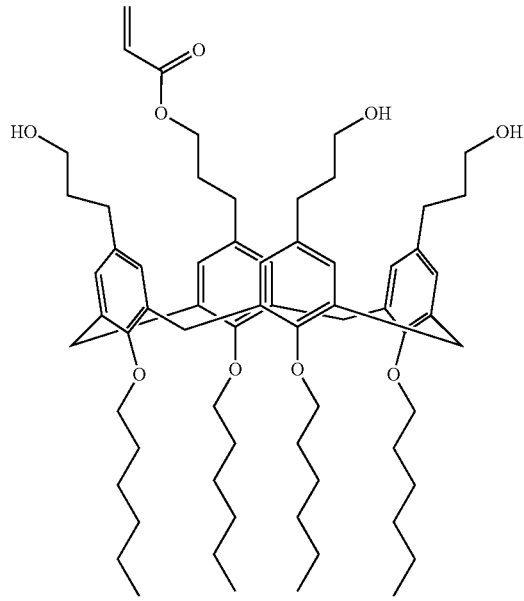

(57-1)

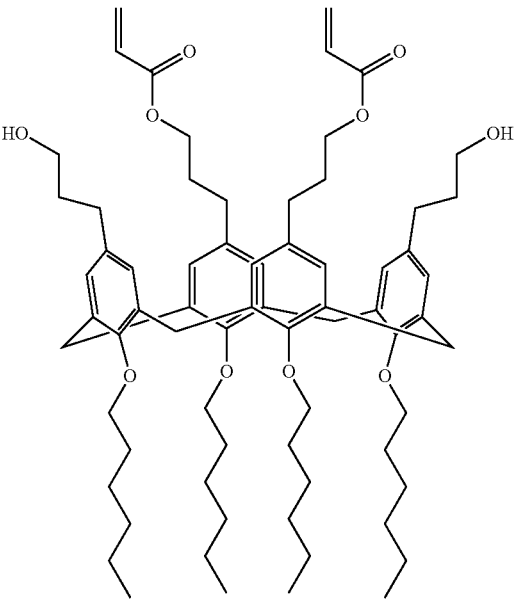

(57-3)

(57-4)

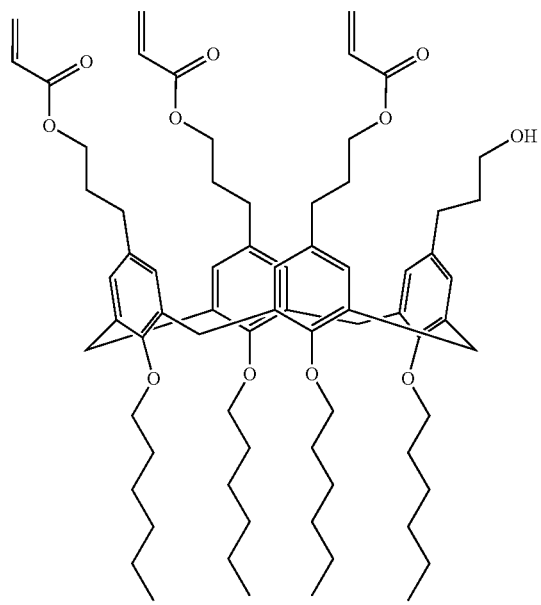

(58-2)

(58-3)

(58-4)

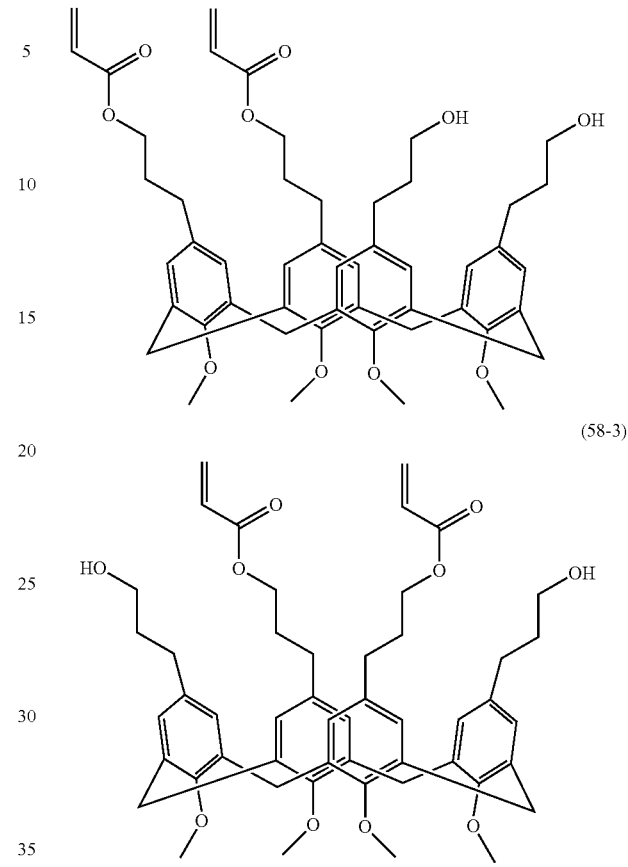

Example 58

This example was carried out as in Example 57 except that the compound obtained in Synthesis Example 56 (3.50 g, 4.91 mmol) was used instead of the compound obtained in Synthesis Example 55. Thus, compounds represented by the formulae below were obtained: a compound (58-1) in an amount of 0.508 g (13.5% yield); a mixture of compounds (58-2) and (58-3) in an amount of 2.10 g (53.1% yield); and a compound (58-4) in an amount of 0.429 g (9.4% yield).

[Chem. 141]

(58-1)

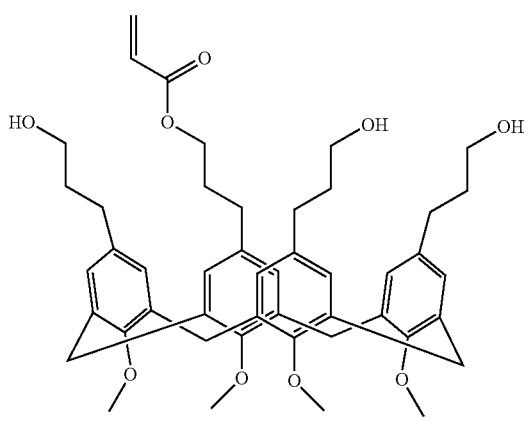

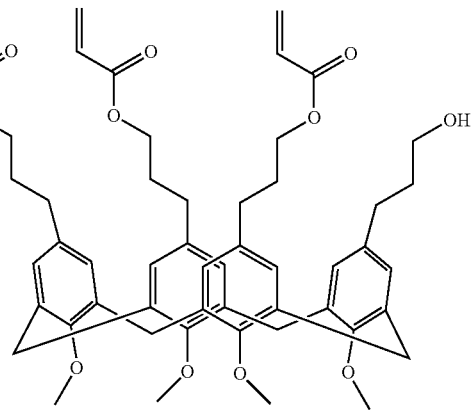

Example 59

This example was carried out as in Example 57 except that the compound obtained in Synthesis Example 57 (3.50 g, 3.97 mmol) was used instead of the compound obtained in Synthesis Example 55. Thus, compounds represented by the formulae below were obtained: a compound (59-1) in an amount of 0.423 g (11.4% yield); a mixture of compounds (59-2) and (59-3) in an amount of 2.153 g (54.8% yield); and a compound (59-4) in an amount of 0.462 g (10.6% yield).

[Chem. 142]

(59-1)
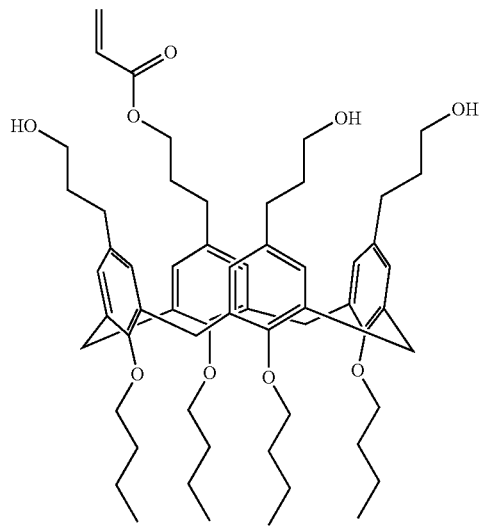

(59-3)
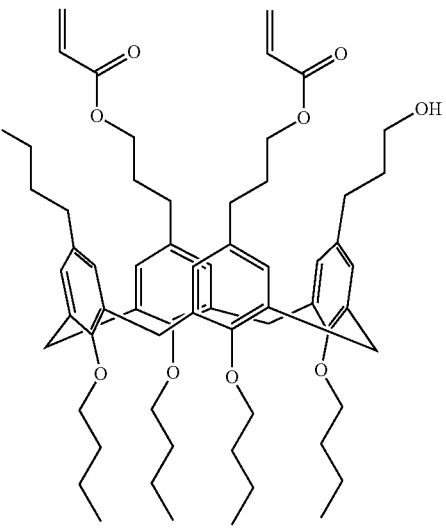

(59-2)
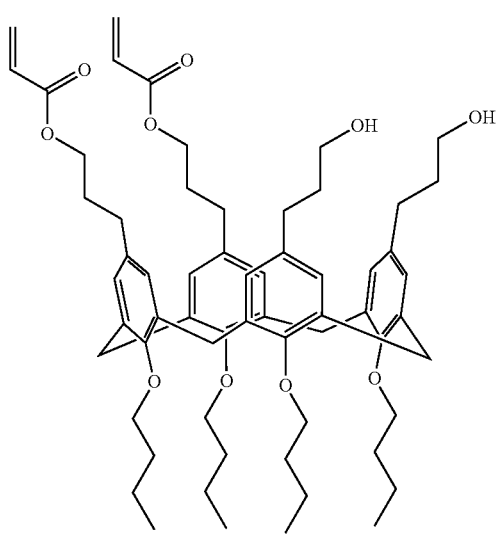

(59-4)
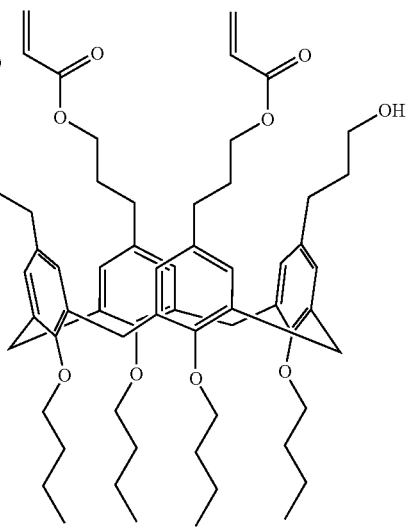

Example 60

This example was carried out as in Example 57 except that the compound obtained in Synthesis Example 58 (3.50 g, 3.33 mmol) was used instead of the compound obtained in Synthesis Example 55. Thus, compounds represented by the formulae below were obtained: a compound (60-1) in an amount of 0.350 g (9.5% yield); a mixture of compounds (60-2) and (60-3) in an amount of 2.197 g (56.9% yield); and a compound (60-4) in an amount of 0.533 g (13.2% yield).

[Chem. 143]

(60-1)

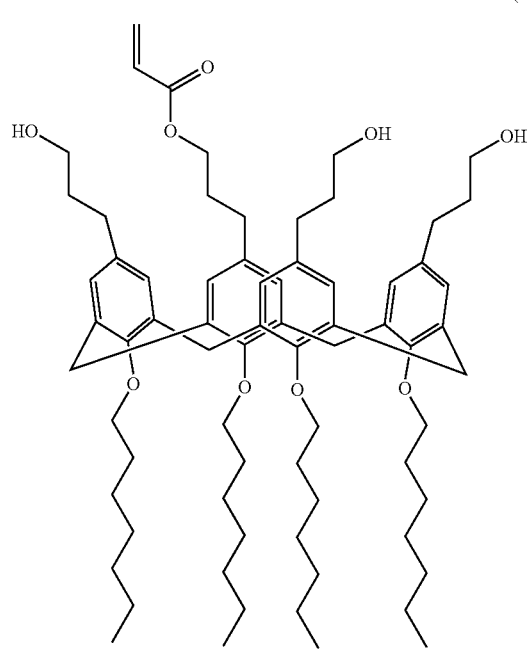

(60-3)

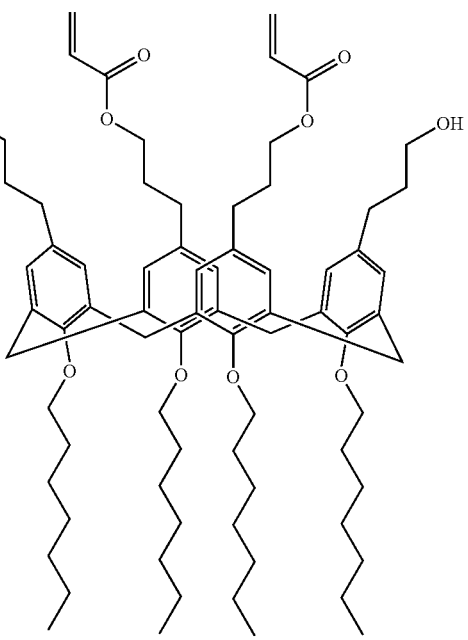

(60-2)

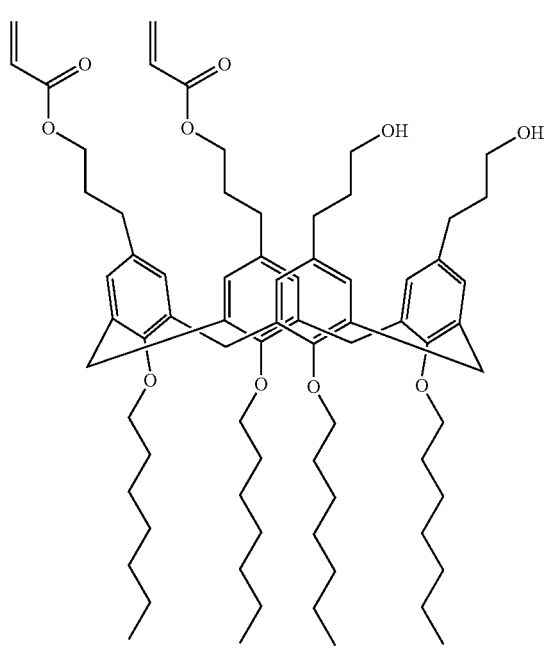

(60-4)

Example 61

This example was carried out as in Example 57 except that the compound obtained in Synthesis Example 59 (4.00 g, 2.40 mmol) was used instead of the compound obtained in Synthesis Example 55. Thus, compounds represented by the formulae below were obtained: a compound (61-1) in an amount of 0.425 g (10.3% yield); a mixture of compounds (61-2) and (61-3) in an amount of 2.445 g (55.7% yield); and a compound (61-4) in an amount of 0.565 g (12.5% yield).

[Chem. 144]
(61-1)
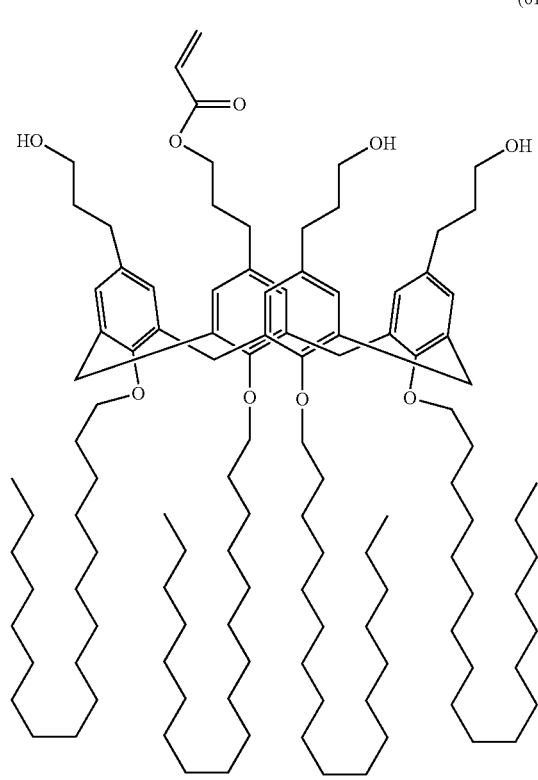
(61-3)
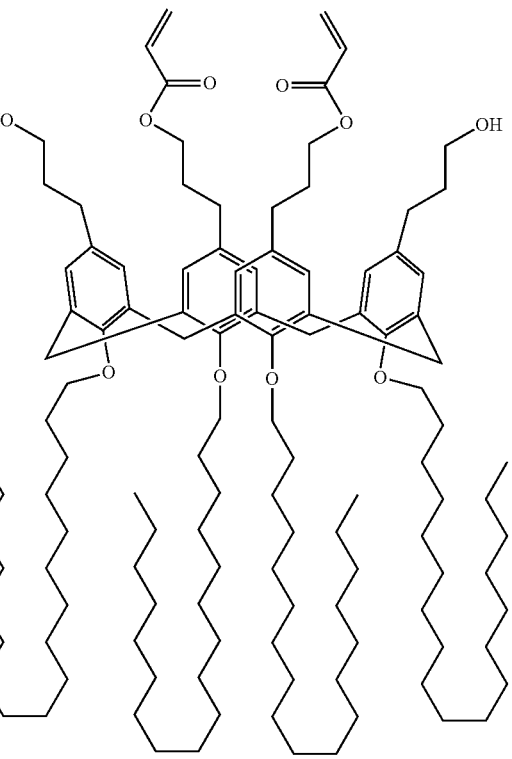
(61-2)
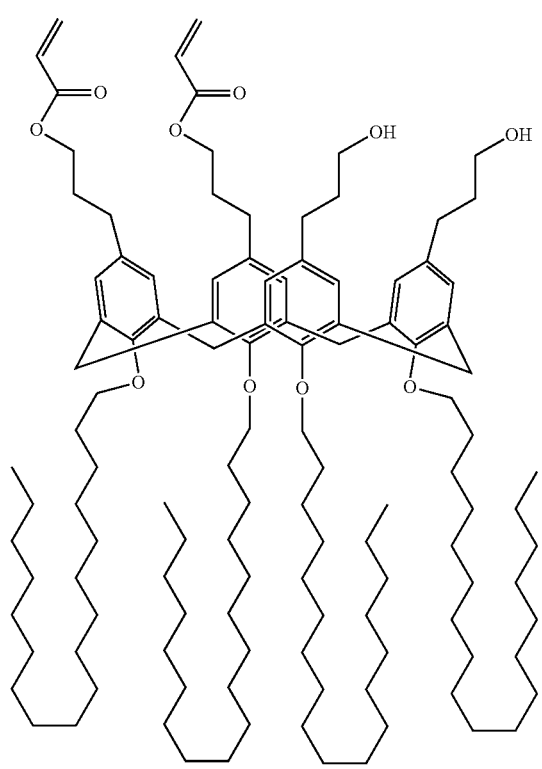
(61-4)

Synthesis Example 65

In a 100-mL four-neck flask equipped with a stirrer, a thermometer, and a reflux condenser, 2.50 g (2.52 mmol) of the compound obtained in Synthesis Example 55, 3.96 g (15.10 mmol) of triphenylphosphine, 3.267 g (15.10 mmol) of 2-[[[1,1-dimethylethyl)dimethylsilyl]oxy]-2-propenoic acid, and 43 mL of tetrahydrofuran were added and stirred. Next, in an ice bath, 3.053 g (15.10 mmol) of diisopropyl azodicarboxylate was added dropwise over 30 minutes, and stirring was performed at room temperature for another 12 hours. The reaction solution was concentrated using an evaporator. Hexane was added to remove by-products, such as triphenylphosphine, by precipitation. A yellow viscous liquid that was obtained was purified by silica gel column chromatography. Thus, a compound represented by the formula below, which was a pale yellow solid, was obtained (3.251 g, 72.3% yield).

[Chem. 145]

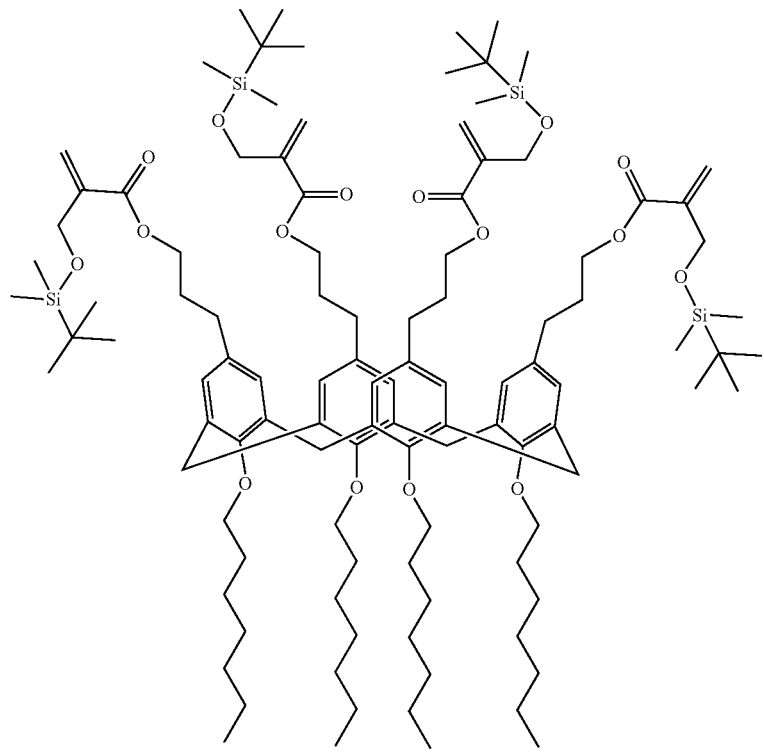

Synthesis Example 66

This example was carried out as in Synthesis Example 65 except that the compound obtained in Synthesis Example 56 (2.50 g, 3.33 mmol) was used instead of the compound obtained in Synthesis Example 55. Thus, a compound represented by the formula below was obtained (3.782 g, 71.6% yield).

[Chem. 146]

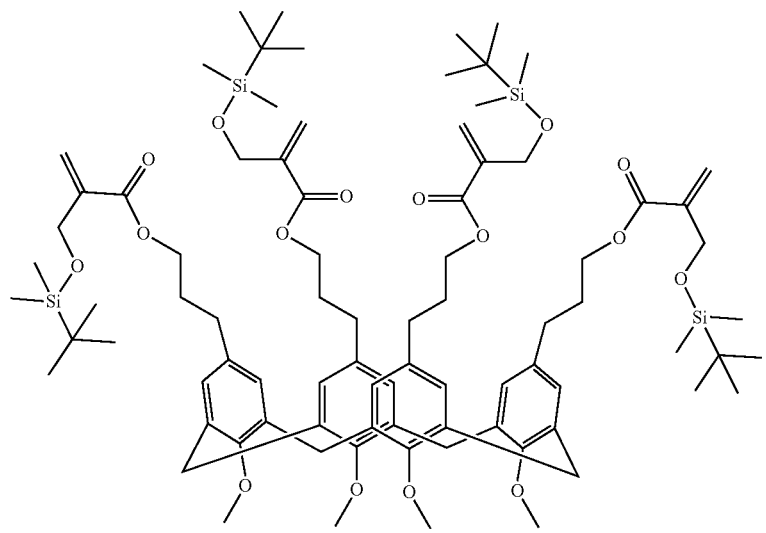

Synthesis Example 67

This example was carried out as in Synthesis Example 65 except that the compound obtained in Synthesis Example 57 (2.50 g, 2.84 mmol) was used instead of the compound obtained in Synthesis Example 55. Thus, a compound represented by the formula below was obtained (3.553 g, 74.8% yield).

[Chem. 147]

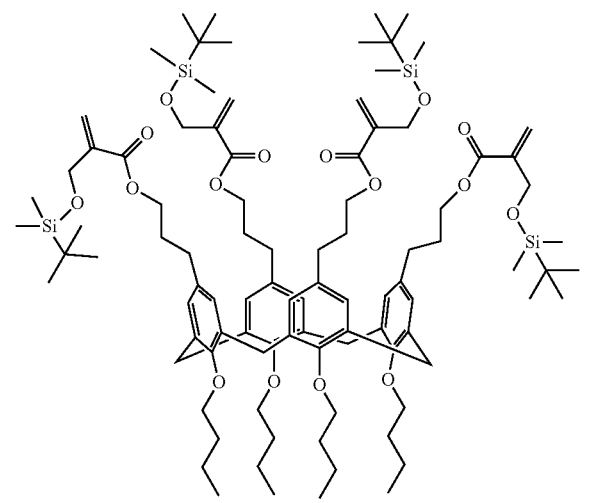

Synthesis Example 68

This example was carried out as in Synthesis Example 65 except that the compound obtained in Synthesis Example 58 (2.50 g, 2.38 mmol) was used instead of the compound obtained in Synthesis Example 55. Thus, a compound represented by the formula below was obtained (3.305 g, 75.3% yield).

[Chem. 148]

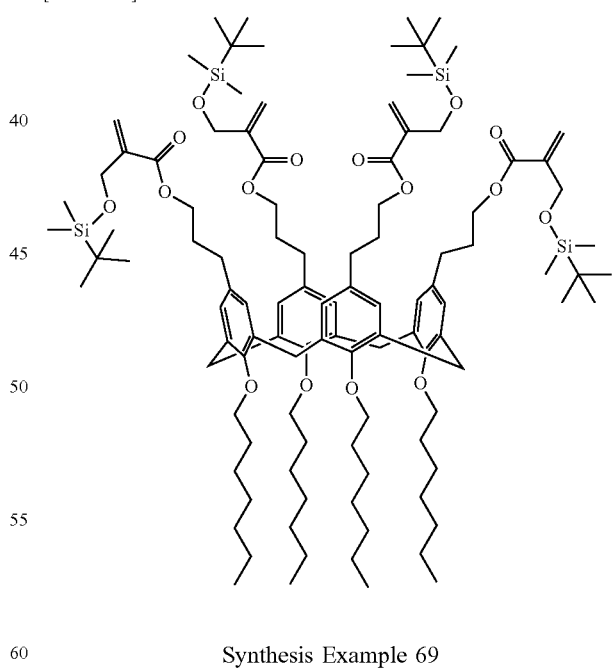

Synthesis Example 69

This example was carried out as in Synthesis Example 65 except that the compound obtained in Synthesis Example 59 (2.50 g, 1.50 mmol) was used instead of the compound obtained in Synthesis Example 55. Thus, a compound represented by the formula below was obtained (3.011 g, 81.6% yield).

[Chem. 149]

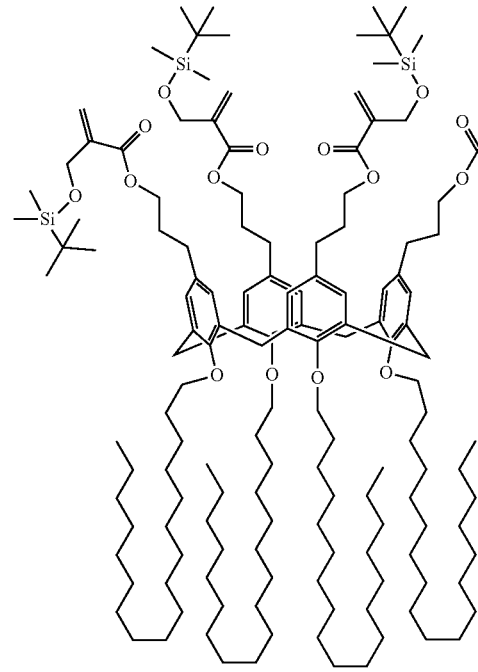

Example 62

In a 100-mL four-neck flask equipped with a stirrer, a thermometer, and a reflux condenser, 2.00 g (1.12 mmol) of the compound obtained in Synthesis Example 65, 0.403 g (6.72 mmol) of acetic acid, and 45 mL of tetrahydrofuran were added and stirred. A clear colorless solution. Subsequently, in an ice bath, 6.72 mL (6.72 mmol) of tetrabutylammonium fluoride (ca. 1 mol/L in tetrahydrofuran) was slowly added dropwise with stirring. Stirring was performed at room temperature for 12 hours. A saturated aqueous ammonium chloride solution was added to the reaction mixture, and then 40 mL of chloroform was added. The reaction mixture was transferred to a separatory funnel to separate the organic layer, and further, the aqueous layer was extracted twice with 40 mL of chloroform. The combined organic layers were washed with saturated brine and subsequently dried with anhydrous magnesium sulfate. The solvent was evaporated using an evaporator, and thus a clear yellow liquid was obtained. The liquid was purified by silica gel column column chromatography. Thus, a compound (62-1), represented by the formula below, which was a white solid, was obtained (1.377 g, 92.5% yield).

[Chem. 150]

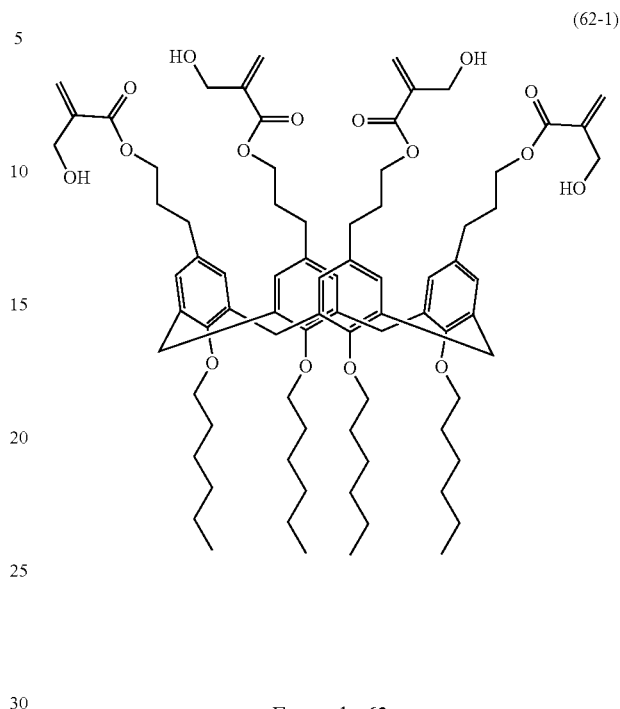

Example 63

This example was carried out as in Example 63 except that the compound obtained in Synthesis Example 66 (2.0 g, 1.33 mmol) was used instead of the compound obtained in Synthesis Example 65. Thus, a compound represented by the formula below was obtained (1.276 g, 91.6% yield).

[Chem. 151]

(63-1)

Example 64

This example was carried out as in Example 63 except that the compound obtained in Synthesis Example 67 (2.0 g, 1.19 mmol) was used instead of the compound obtained in Synthesis Example 65. Thus, a compound represented by the formula below was obtained (1.276 g, 91.6% yield).

[Chem. 152]

(64-1)

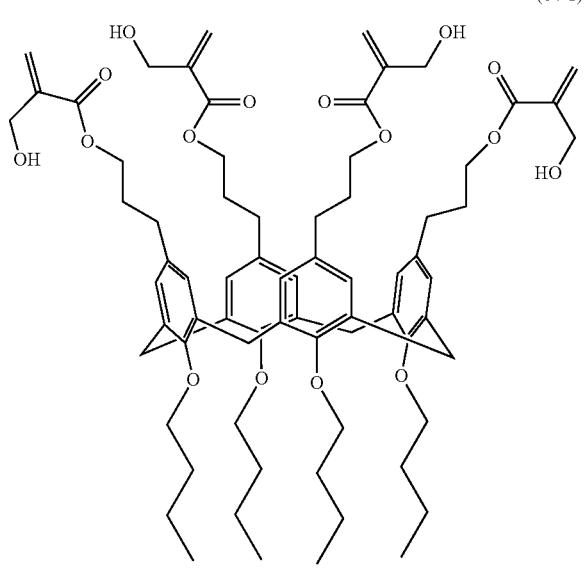

Example 65

This example was carried out as in Example 63 except that the compound obtained in Synthesis Example 68 (2.0 g, 1.09 mmol) was used instead of the compound obtained in Synthesis Example 65. Thus, a compound represented by the formula below was obtained (1.405 g, 94.3% yield).

[Chem. 153]

(65-1)

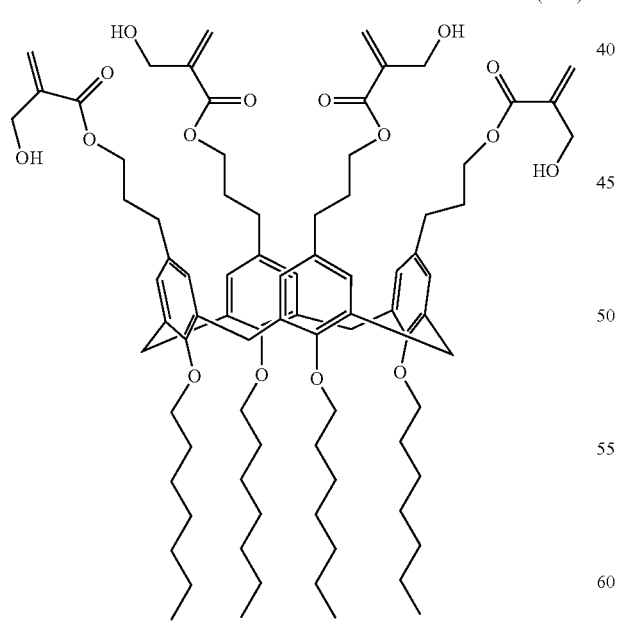

Example 66

This example was carried out as in Example 63 except that the compound obtained in Synthesis Example 69 (2.5 g, 1.02 mmol) was used instead of the compound obtained in Synthesis Example 65. Thus, a compound represented by the formula below was obtained (1.887 g, 92.7% yield).

[Chem. 154]

(69-1)

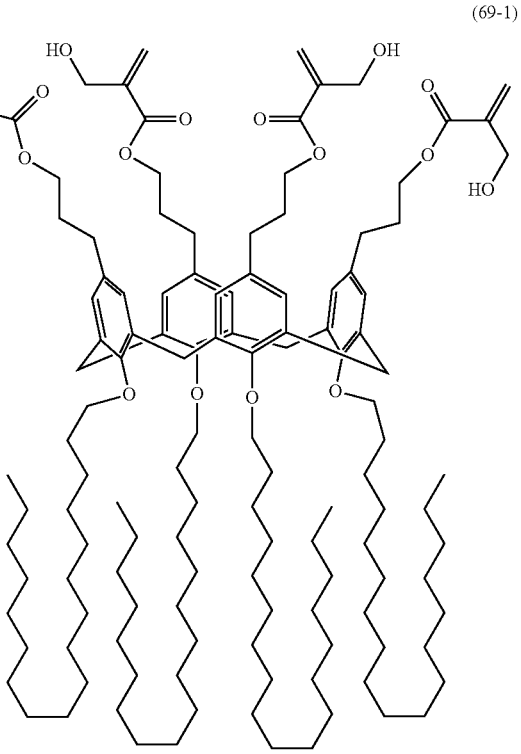

Comparative Example

In a 100-mL four-neck flask equipped with a stirrer, a thermometer, and a reflux condenser, 1.00 g (1.212 mmol) of the compound obtained in Synthesis Example 20, 10.00 g (138.7 mmol) of tetrahydrofuran, 1.907 g (7.271 mmol) of triphenylphosphine, and 0.6260 g (7.271 mmol) of methacrylic acid were added and stirred. A clear pale yellow solution. Subsequently, in an ice bath, 1.470 g (7.271 mmol) of diisopropyl azodicarboxylate was added dropwise over 30 minutes. A clear pale yellow solution. Stirring was performed at room temperature for 6 hours. Hexane was added to the reaction solution to remove by-products, such as triphenylphosphine, by precipitation, and thereafter chloroform extraction was carried out. The extracts were washed with water and saturated brine and subsequently dried with magnesium sulfate. The solvent was evaporated using an evaporator. An orange viscous liquid was subjected to column chromatography (developing solvent:n-hexane:acetone=90:10). Thus, a compound (1'), represented by the formula below, was obtained. The compound was dried under vacuum (at 60° C. for 6 hours or more). The compound was in an amount of 0.9058 g, with the yield being 68.1%.

[Chem. 155]

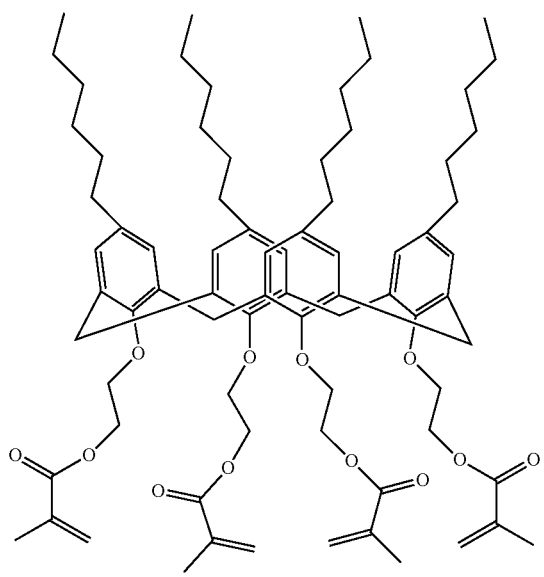

<Production of Curable Composition>

0.25 g of a calixarene compound that was obtained, 0.25 g of dipentaerythritol hexaacrylate (A-DPH, manufactured by Shin Nakamura Chemical Co., Ltd.), 0.005 g of a polymerization initiator (Irgacure 369, manufactured by BASF), and 9.5 g of propylene glycol monomethyl ether acetate were combined and mixed together. Thus, a curable composition was obtained.

<Preparation of Layered Structures>

The curable composition was applied onto substrates 1 to 4, listed below, by spin coating, in a manner such that the film thickness after curing was approximately 0.5 μm. The resultant was dried on a 100° C. hot plate for 2 minutes. In a nitrogen atmosphere, the curable composition was cured by being irradiated with UV light at an intensity of 500 mJ/cm², which was applied using a high-pressure mercury lamp. Thus, layered structures were obtained.
Substrate 1: a polymethylmethacrylate resin sheet
Substrate 2: an aluminum sheet
Substrate 3: a polyethylene terephthalate film including a SiO₂ thin film (a thickness of 100 nm) layer (the curable composition was applied on the SiO₂ thin film)

<Evaluation of Adhesion>

The layered structures were stored for 24 hours in an environment at 23° C. and 50% RH and thereafter evaluated for adhesion in accordance with JIS K 6500-5-6 (adhesion properties: a cross-cut method). The cellophane tape used was CT-24, manufactured by Nichiban Co., Ltd. The evaluation criteria are as follows.

A: 80 or greater of the 100 squares remained unpeeled
B: 50 to 79 of the 100 squares remained unpeeled
C: 49 or less of the 100 squares remained unpeeled <Evaluation of Resistance to Moist Heat>

The curable composition was applied onto a 5-inch SiO substrate by using an applicator, in a manner such that the film thickness was approximately 50 μm. The resultant was dried on a 100° C. hot plate for 2 minutes. A mask having an L/S pattern of L/S=50 μm/50 μm was brought into close contact with the obtained coating. In a nitrogen atmosphere, the composition was cured by being irradiated with UV light at an intensity of 1000 mJ/cm², which was applied using a high-pressure mercury lamp. The exposed substrate that was obtained was developed with ethyl acetate. Thus, substrates to be evaluated were obtained. The substrates that were obtained were stored in a chamber at constant temperature and humidity, at 85° C. and 85% RH, for 100 hours. The state after 100 hours was examined with a laser microscope (a VK-X200, manufactured by Keyence Corporation) to determine the state of the pattern. The evaluation criteria are as follows.

A: All the patterns were favorably modified or maintained

B: Cracking or chipping was observed in some of the patterns

C: Cracking or chipping was observed in patterns, and pattern delamination was observed

TABLE 1

| Calixarene compound | | 1-1 | 1-2 | 2-1 | 2-2 | 3-1 | 3-2 |
|---|---|---|---|---|---|---|---|
| Adhesion | Substrate 1 | A | A | A | A | A | A |
| | Substrate 2 | A | A | A | A | A | A |
| | Substrate 3 | A | A | A | A | A | A |
| Resistance to Moist Heat | | A | A | A | A | A | A |
| Calixarene compound | | 4-1 | 4-2 | 5-1 | 5-2 | 6-1 | 6-2 |
| Adhesion | Substrate 1 | A | A | A | A | A | A |
| | Substrate 2 | A | A | A | A | A | A |
| | Substrate 3 | A | A | A | A | A | A |
| Resistance to Moist Heat | | A | A | A | A | A | A |
| Calixarene compound | | 7-1 | 7-2 | 7-3 | 7-4 | 8-1 | 8-2 |
| Adhesion | Substrate 1 | A | A | A | B | A | A |
| | Substrate 2 | A | A | A | A | A | A |
| | Substrate 3 | A | A | A | A | A | A |
| Resistance to Moist Heat | | A | A | A | A | A | A |

TABLE 2

| Calixarene compound | | 8-3 | 8-4 | 9-1 | 9-2 | 9-3 | 9-4 |
|---|---|---|---|---|---|---|---|
| Adhesion | Substrate 1 | A | B | A | A | A | B |
| | Substrate 2 | A | A | A | A | A | A |
| | Substrate 3 | A | A | A | A | A | A |
| Resistance to Moist Heat | | A | A | A | A | A | A |
| Calixarene compound | | 10-1 | 10-2 | 10-3 | 10-4 | 11-1 | 11-2 |
| Adhesion | Substrate 1 | A | A | A | B | A | A |
| | Substrate 2 | A | A | A | A | A | A |
| | Substrate 3 | A | A | A | A | A | A |
| Resistance to Moist Heat | | A | A | A | A | A | A |
| Calixarene compound | | 12-1 | 12-2 | 13-1 | 13-2 | 14-1 | 14-2 |
| Adhesion | Substrate 1 | A | A | A | A | A | A |
| | Substrate 2 | A | A | A | A | A | A |
| | Substrate 3 | A | A | A | A | A | A |
| Resistance to Moist Heat | | A | A | A | A | A | A |

TABLE 3

| Calixarene compound | | 15-1 | 15-2 | 16-1 | 16-2 | 17-1 | 17-2 |
|---|---|---|---|---|---|---|---|
| Adhesion | Substrate 1 | A | A | A | A | A | A |
| | Substrate 2 | A | A | A | A | A | A |
| | Substrate 3 | A | A | A | A | A | A |
| Resistance to Moist Heat | | A | A | A | A | A | A |

TABLE 3-continued

| Calixarene compound | | 18-1 | 18-2 | 19-1 | 19-2 | 20-1 | 20-2 |
|---|---|---|---|---|---|---|---|
| Adhesion | Substrate 1 | A | A | A | A | A | A |
|  | Substrate 2 | A | A | A | A | A | A |
|  | Substrate 3 | A | A | A | A | A | A |
| Resistance to Moist Heat | | A | A | A | A | A | A |
| Calixarene compound | | 21-1 | 21-2 | 22-1 | 22-2 | 23-1 | 23-2 |
| Adhesion | Substrate 1 | A | A | A | A | A | A |
|  | Substrate 2 | A | B | A | B | A | A |
|  | Substrate 3 | A | A | A | A | A | A |
| Resistance to Moist Heat | | A | A | A | A | A | A |

TABLE 4

| Calixarene compound | | 23-3 | 23-4 | 24-1 | 24-2 | 24-3 | 24-4 |
|---|---|---|---|---|---|---|---|
| Adhesion | Substrate 1 | A | B | A | A | A | A |
|  | Substrate 2 | A | A | A | A | A | A |
|  | Substrate 3 | A | A | A | A | A | A |
| Resistance to Moist Heat | | A | A | A | A | A | A |
| Calixarene compound | | 25-1 | 25-2 | 25-3 | 25-4 | 26-1 | 26-2 |
| Adhesion | Substrate 1 | A | A | A | B | A | A |
|  | Substrate 2 | A | A | A | A | A | A |
|  | Substrate 3 | A | A | A | A | A | A |
| Resistance to Moist Heat | | A | A | A | A | A | A |
| Calixarene compound | | 26-3 | 26-4 | 27-1 | 27-2 | 27-3 | 27-4 |
| Adhesion | Substrate 1 | A | B | A | A | A | A |
|  | Substrate 2 | A | A | A | A | A | B |
|  | Substrate 3 | A | A | A | A | A | B |
| Resistance to Moist Heat | | A | A | A | A | A | A |

TABLE 5

| Calixarene compound | | 28-1 | 28-2 | 28-3 | 28-4 | 29-1 | 29-2 |
|---|---|---|---|---|---|---|---|
| Adhesion | Substrate 1 | A | A | A | B | A | A |
|  | Substrate 2 | A | A | A | A | A | A |
|  | Substrate 3 | A | A | A | A | A | A |
| Resistance to Moist Heat | | A | A | A | A | A | A |

TABLE 5-continued

| Calixarene compound | | 29-3 | 29-4 | 30-1 | 30-2 | 30-3 | 30-4 |
|---|---|---|---|---|---|---|---|
| Adhesion | Substrate 1 | A | B | A | A | A | B |
|  | Substrate 2 | A | A | A | A | A | A |
|  | Substrate 3 | A | A | A | A | A | A |
| Resistance to Moist Heat | | A | A | A | A | A | A |
| Calixarene compound | | 31-1 | 32-1 | 33-1 | 34-1 | 35-1 | 36-1 |
| Adhesion | Substrate 1 | A | B | A | A | A | A |
|  | Substrate 2 | A | A | A | A | A | A |
|  | Substrate 3 | A | A | A | A | A | A |
| Resistance to Moist Heat | | A | A | A | A | A | A |

TABLE 6

| Calixarene compound | | 37-1 | 38-1 | 39-1 | 40-1 | 41-1 | 42-1 |
|---|---|---|---|---|---|---|---|
| Adhesion | Substrate 1 | A | A | A | B | A | A |
|  | Substrate 2 | A | A | A | A | A | A |
|  | Substrate 3 | A | A | A | A | A | A |
| Resistance to Moist Heat | | A | A | A | A | A | A |
| Calixarene compound | | 43-1 | 44-1 | 45-1 | 46-1 | 47-1 | 47-1&2 |
| Adhesion | Substrate 1 | A | A | A | A | A | A |
|  | Substrate 2 | A | B | B | A | A | A |
|  | Substrate 3 | A | B | B | A | A | A |
| Resistance to Moist Heat | | A | B | B | A | A | A |
| Calixarene compound | | 47-4 | 48-1 | 48-2&3 | 48-4 | 49-1 | 49-2&3 |
| Adhesion | Substrate 1 | B | A | A | B | A | A |
|  | Substrate 2 | A | A | A | A | A | A |
|  | Substrate 3 | A | A | A | A | A | A |
| Resistance to Moist Heat | | A | A | A | A | A | A |

TABLE 7

| Calixarene compound | | 49-4 | 50-1 | 50-2&3 | 50-4 | 51-1 | 51-2&3 |
|---|---|---|---|---|---|---|---|
| Adhesion | Substrate 1 | B | A | A | B | A | A |
|  | Substrate 2 | A | A | A | A | A | A |
|  | Substrate 3 | A | A | A | A | A | A |
| Resistance to Moist Heat | | A | A | A | A | A | A |
| Calixarene compound | | 51-4 | 52-1 | 53-1 | 54-1 | 55-1 | 56-1 |
| Adhesion | Substrate 1 | B | A | A | A | A | A |
|  | Substrate 2 | A | A | A | A | A | A |
|  | Substrate 3 | A | A | A | A | A | A |
| Resistance to Moist Heat | | A | A | A | A | A | A |
| Calixarene compound | | 57-1 | 57-2&3 | 57-4 | 58-1 | 58-2&3 | 58-4 |
| Adhesion | Substrate 1 | A | A | B | A | A | B |
|  | Substrate 2 | A | A | A | A | A | A |
|  | Substrate 3 | A | A | A | A | A | A |
| Resistance to Moist Heat | | A | A | A | A | A | A |

TABLE 8

| Calixarene compound | | 59-1 | 59-2&3 | 59-4 | 60-1 | 60-2&3 | 60-4 |
|---|---|---|---|---|---|---|---|
| Adhesion | Substrate 1 | A | A | B | A | A | B |
|  | Substrate 2 | A | A | A | A | A | A |
|  | Substrate 3 | A | A | A | A | A | A |
| Resistance to Moist Heat | | A | A | A | A | A | A |

TABLE 8-continued

| Calixarene compound | 61-1 | 61-2&3 | 61-4 | 62-1 | 63-1 | 64-1 |
|---|---|---|---|---|---|---|
| Adhesion Substrate 1 | A | A | B | A | A | A |
| Substrate 2 | A | A | A | A | A | A |
| Substrate 3 | A | A | A | A | A | A |
| Resistance to Moist Heat | A | A | A | A | A | A |

| Calixarene compound | 65-1 | 66-1 | 1' |
|---|---|---|---|
| Adhesion Substrate 1 | A | A | C |
| Substrate 2 | A | A | C |
| Substrate 3 | A | A | C |
| Resistance to Moist Heat | A | A | B |

The invention claimed is:

1. A calixarene compound represented by structural formula (1-1) below,

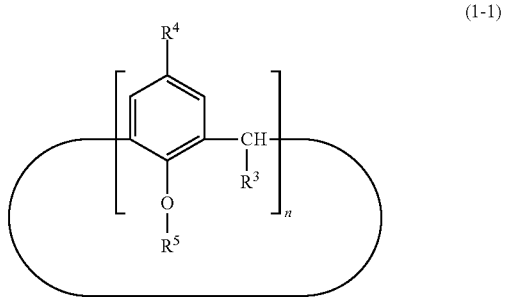

(1-1)

wherein
each $R^4$ is a monovalent organic group (d1), which is represented by -X-R where X is a direct bond or a carbonyl group, and R is a hydrogen atom or an aliphatic hydrocarbon group having 1 to 20 carbon atoms, wherein each $R^4$ may be identical to or different from one another,
each $R^5$ is independently:
  a structural moiety (A), which has a —CH$_2$OH group;
  a structural moiety (B), which has a carbon-carbon unsaturated bond; or
  a structural moiety (C), which has both a —CH$_2$OH group and a carbon-carbon unsaturated bond,
  wherein each $R^5$ may be identical to or different from one another,
  and wherein at least one $R^5$ in the calixarene compound has a —CH$_2$OH group and at least one $R^5$ in the calixarene compound has a carbon-carbon unsaturated bond,
each $R^3$ is independently a hydrogen atom or an optionally substituted aliphatic hydrocarbon group, wherein each $R^4$ may be identical to or different from one another, and
n is 4, 6, or 8.

2. The calixarene compound according to claim 1, wherein $R^4$'s in structural formula (1-1) are a group represented by -X-R where X is a direct bond or a carbonyl group, and R is a hydrogen atom or a linear alkyl group.

3. The calixarene compound according to claim 1, wherein $R^3$'s in structural formula (1-1) are a hydrogen atom.

4. The calixarene compound according to claim 1, wherein the structural moiety (B), which has a carbon-carbon unsaturated bond, is a vinyl group, a propargyl group, a (meth)acryloyl group, a (meth)acryloylamino group, or a structural moiety represented by structural formula (B-1) or (B-2) below,

[Chem. 3]

(B-1)

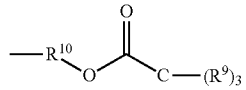

(B-2)

wherein
$R^8$ and $R^{10}$ are each independently an aliphatic hydrocarbon group or a direct bond, and
$R^9$'s are each independently one of a hydrogen atom, an alkyl group, a vinyl group, a vinyloxy group, a vinyloxyalkyl group, an allyl group, an allyloxy group, an allyloxyalkyl group, a propargyl group, a propargyloxy group, a propargyloxyalkyl group, a (meth)acryloyl group, a (meth)acryloyloxy group, a (meth)acryloyloxyalkyl group, a (meth)acryloylamino group, and a (meth)acryloylaminoalkyl group, and at least one of $R^9$'s is one of a vinyl group, a vinyloxy group, a vinyloxyalkyl group, an allyl group, an allyloxy group, an allyloxyalkyl group, a propargyl group, a propargyloxy group, a propargyloxyalkyl group, a (meth)acryloyl group, a (meth)acryloyloxy group, a (meth)acryloyloxyalkyl group, a (meth)acryloylamino group, and a (meth)acryloylaminoalkyl group.

5. The calixarene compound according to claim 1, wherein the structural moiety (C), which has both a —CH$_2$OH group and a carbon-carbon unsaturated bond, is a structural moiety represented by structural formula (C-1) or (C-2) below,

[Chem. 4]

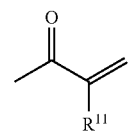

(C-1)

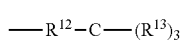

(C-2)

wherein
$R^{11}$ is an alkyl group having a —CH$_2$OH group,
$R^{12}$ is an aliphatic hydrocarbon group or a direct bond, and
$R^{13}$'s are each independently one of a hydrogen atom, an alkyl group, an alkyl group having a —CH$_2$OH group, a vinyl group, a vinyloxy group, a vinyloxyalkyl group, an allyl group, an allyloxy group, an allyloxyalkyl group, a propargyl group, a propargyloxy group, a propargyloxyalkyl group, a (meth)acryloyl group, a (meth)acryloyloxy group, a (meth)acryloyloxyalkyl group, a (meth)acryloylamino group, a (meth)acryloylaminoalkyl group, and a structural moiety represented by structural formula (C-2-1) below,

[Chem. 5]

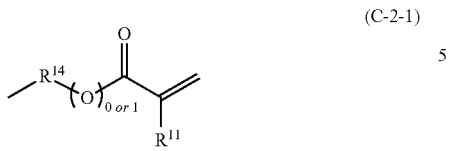

(C-2-1)

wherein $R^{14}$ is an aliphatic hydrocarbon group or a direct bond, and $R^{11}$ is an alkyl group having a —CH$_2$OH group,
provided that at least one of $R^{13}$'s is an alkyl group having a —CH$_2$OH group or a structural moiety represented by structural formula (C-2-1), and at least one of $R^{13}$'s is one of a vinyl group, a vinyloxy group, an allyl group, an allyloxy group, a propargyl group, a propargyloxy group, a (meth)acryloyl group, a (meth)acryloyloxy group, a (meth)acryloyloxyalkylene group, a (meth)acryloylamino group, a (meth)acryloylaminoalkylene group, and a structural moiety represented by structural formula (C-2-1).

6. The calixarene compound according to claim 1, wherein n is 4.

7. A curable composition comprising the calixarene compound according to claim 1.

8. A cured product of the curable composition according to claim 7.

\* \* \* \* \*